US006801828B2

United States Patent
Popp et al.

(10) Patent No.: US 6,801,828 B2
(45) Date of Patent: Oct. 5, 2004

(54) WEB GUIDING SYSTEM AND METHOD

(75) Inventors: Robert L. Popp, Hortonville, WI (US); Kyle S. Allen, Neenah, WI (US); Jamie L. Bell, Brillion, WI (US); Henry L. Carbone, II, St. Paul, MN (US); Scott G. Chapple, Neenah, WI (US); Tim G. Dollevoet, Kimberly, WI (US); John G. Hein, Appleton, WI (US); Archie Dodds Morgan, Neenah, WI (US); Brian Robert Vogt, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 28 days.

(21) Appl. No.: 10/299,097

(22) Filed: Nov. 18, 2002

(65) Prior Publication Data

US 2004/0030438 A1 Feb. 12, 2004

Related U.S. Application Data

(60) Provisional application No. 60/401,805, filed on Aug. 7, 2002.

(51) Int. Cl.$^7$ ............................................. G06F 19/00
(52) U.S. Cl. .................... 700/122; 127/131; 162/273; 356/430; 356/431
(58) Field of Search ................................ 700/131, 122, 700/127, 110; 162/263; 356/429, 430, 431; 33/706; 348/88

(56) References Cited

U.S. PATENT DOCUMENTS

| | | |
|---|---|---|
| 3,244,863 A | 4/1966 | Paterson |
| 3,781,531 A | 12/1973 | Baker |
| 3,835,332 A | 9/1974 | Bridges |
| 3,843,890 A | 10/1974 | Anthony, Jr. et al. |
| 3,991,663 A | 11/1976 | Glasby |
| 4,320,463 A | 3/1982 | Himmelstein |
| 4,361,260 A | 11/1982 | Hanlan |
| 4,663,220 A | 5/1987 | Wisneski et al. |
| 4,680,205 A | 7/1987 | Lerner et al. |
| 4,704,116 A | 11/1987 | Enloe |
| 4,736,680 A | 4/1988 | Wales et al. |
| 4,795,510 A | 1/1989 | Wittrock et al. |
| 4,837,715 A | 6/1989 | Ungpiyakul et al. |
| 4,940,464 A | 7/1990 | Van Gompel et al. |
| 4,945,252 A | 7/1990 | Lerner et al. |
| 5,018,213 A | 5/1991 | Sikes |
| 5,045,135 A | 9/1991 | Meissner et al. |
| 5,068,799 A | 11/1991 | Jarrett, Jr. |
| 5,094,708 A | 3/1992 | Bechtel et al. |
| 5,104,116 A | 4/1992 | Pohjola |

(List continued on next page.)

FOREIGN PATENT DOCUMENTS

| | | |
|---|---|---|
| DE | 1273214 B | 7/1968 |
| EP | 0217032 | 4/1987 |
| WO | WO01/87218 A2 | 11/2001 |

*Primary Examiner*—Albert W. Paladini
(74) *Attorney, Agent, or Firm*—Senniger, Powers, Leavitt & Roedel

(57) ABSTRACT

Systems and methods for guiding one or more web components in connection with a web converting manufacturing process such as that used for manufacturing disposable absorbent garments. Some of the disclosed embodiments include relating inspection data, such as product (or process) attribute data, to data from other manufacturing-related systems. Also disclosed are systems and methods for linking product (or process) attribute data obtained during the manufacturing process with one or more data sources including raw material data, process setting data, product quality data, and/or productivity data. Also disclosed are systems and methods for identifying manufacturing set point changes and automatically implementing such changes and automated web steering changes based on data from one or more inspection systems.

79 Claims, 27 Drawing Sheets

(7 of 27 Drawing Sheet(s) Filed in Color)

U.S. PATENT DOCUMENTS

| | | | |
|---|---|---|---|
| 5,119,981 A | 6/1992 | Gnuechtel et al. | |
| 5,212,647 A | 5/1993 | Raney et al. | |
| 5,212,656 A | 5/1993 | Clary et al. | |
| 5,221,058 A | 6/1993 | Fillis | |
| 5,226,992 A | 7/1993 | Morman | |
| 5,256,883 A * | 10/1993 | Weichmann et al. | 356/430 |
| 5,286,543 A | 2/1994 | Ungpiyakul et al. | |
| 5,319,550 A | 6/1994 | Griffith | |
| 5,339,257 A | 8/1994 | Layden et al. | |
| 5,359,525 A | 10/1994 | Weyenberg | |
| 5,386,642 A * | 2/1995 | Spies et al. | 33/706 |
| 5,563,809 A | 10/1996 | Williams et al. | |
| 5,659,538 A | 8/1997 | Stuebe et al. | |
| 5,745,365 A * | 4/1998 | Parker | 700/122 |
| 5,764,367 A | 6/1998 | Schaede et al. | |
| 5,766,389 A | 6/1998 | Brandon et al. | |
| 5,818,719 A | 10/1998 | Brandon et al. | |
| 5,858,515 A | 1/1999 | Stokes et al. | |
| 5,896,294 A | 4/1999 | Chow et al. | |
| 5,908,722 A | 6/1999 | Burke et al. | |
| 5,915,612 A | 6/1999 | Hinton | |
| 5,930,139 A | 7/1999 | Chapdelaine et al. | |
| 5,964,970 A | 10/1999 | Woolwine et al. | |
| 5,980,087 A | 11/1999 | Brandon et al. | |
| 6,027,820 A | 2/2000 | O'Hagan et al. | |
| 6,033,502 A | 3/2000 | Coenen et al. | |
| 6,035,243 A | 3/2000 | Galuga et al. | |
| 6,036,805 A | 3/2000 | McNichols | |
| 6,092,002 A | 7/2000 | Kastman et al. | |
| 6,097,427 A * | 8/2000 | Dey et al. | 348/130 |
| 6,165,306 A | 12/2000 | Rajala | |
| 6,224,699 B1 | 5/2001 | Bett et al. | |
| 6,245,168 B1 | 6/2001 | Coenen et al. | |
| 6,253,159 B1 | 6/2001 | Bett et al. | |
| 6,260,188 B1 | 7/2001 | Ungpiyakul et al. | |
| 6,266,436 B1 * | 7/2001 | Bett et al. | 700/110 |
| 6,268,920 B1 | 7/2001 | Ohlig | |
| 6,272,437 B1 | 8/2001 | Woods et al. | |
| 6,295,374 B1 | 9/2001 | Robinson et al. | |
| 6,317,513 B2 | 11/2001 | Michael et al. | |
| 6,323,948 B2 | 11/2001 | Haque et al. | |
| 6,337,217 B1 | 1/2002 | Hause et al. | |
| 6,352,497 B1 | 3/2002 | Hensley et al. | |
| 6,354,984 B1 | 3/2002 | Hensley et al. | |
| 6,535,776 B1 | 3/2003 | Tobin, Jr. et al. | |
| 6,578,583 B2 * | 6/2003 | Smith et al. | 131/84.1 |
| 2001/0038709 A1 | 11/2001 | Bett et al. | |
| 2002/0026879 A1 | 3/2002 | Goldstein | |
| 2002/0030749 A1 | 3/2002 | Nakamura et al. | |
| 2002/0070469 A1 | 6/2002 | Hiatt et al. | |

* cited by examiner

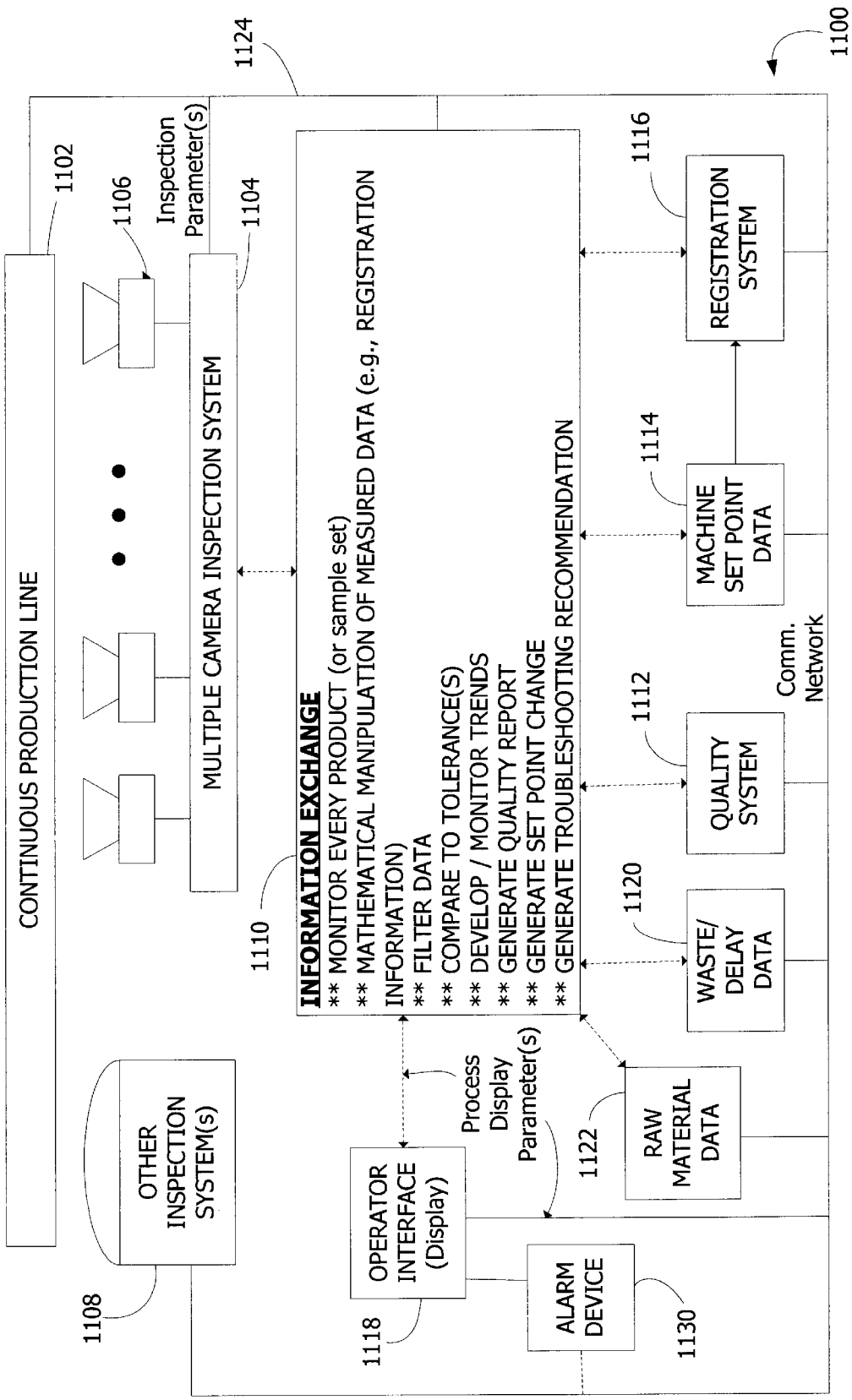

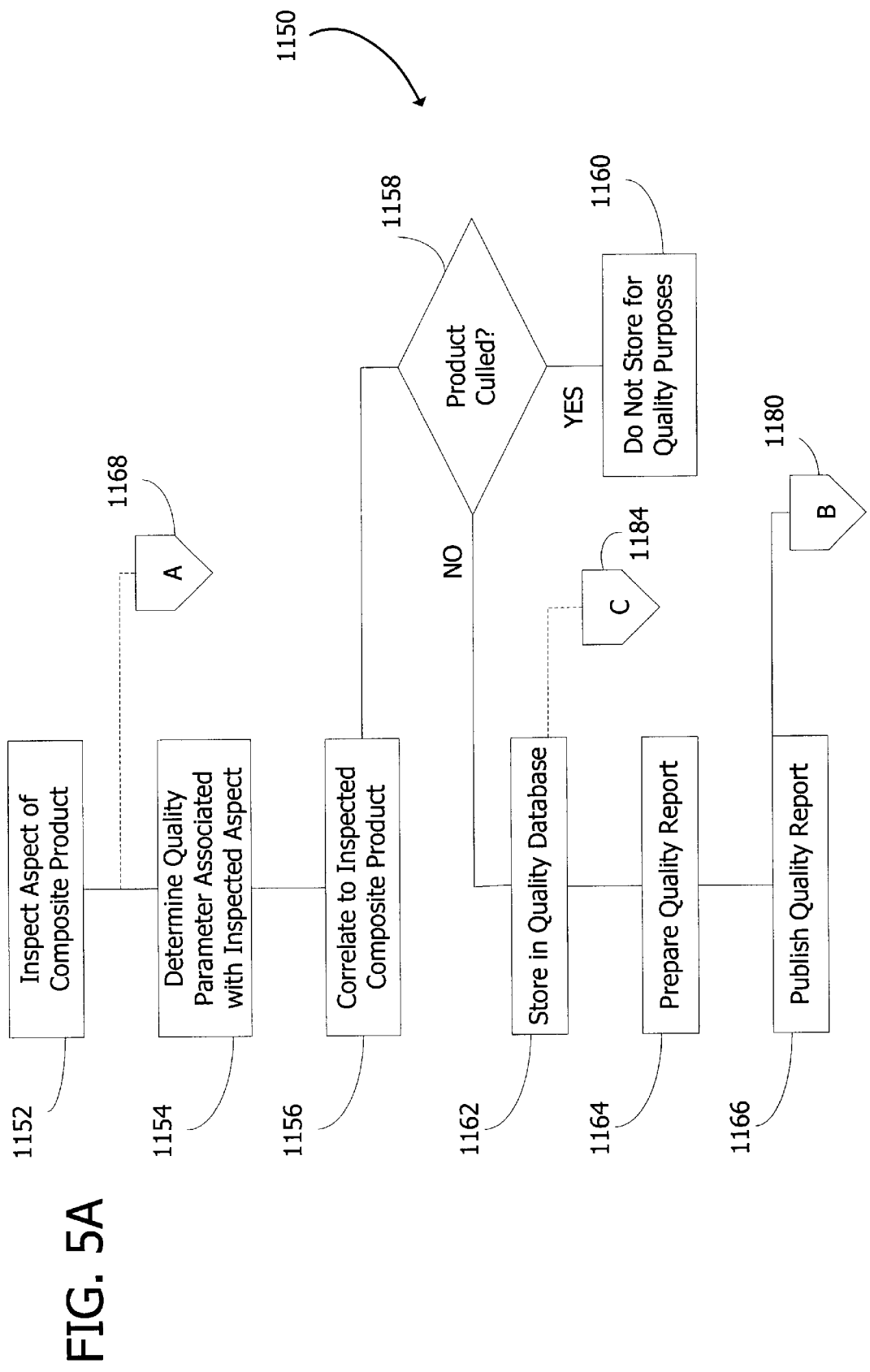

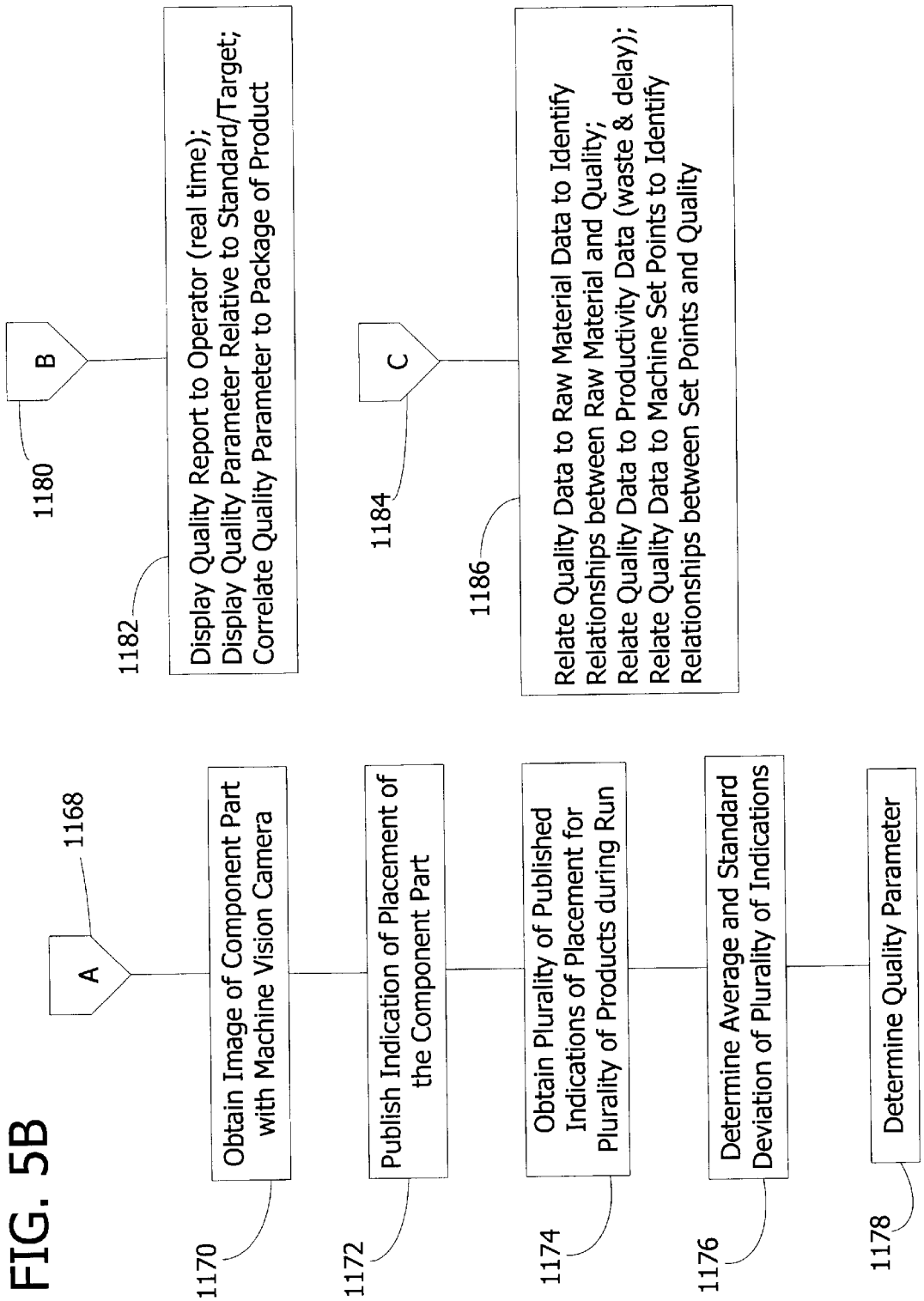

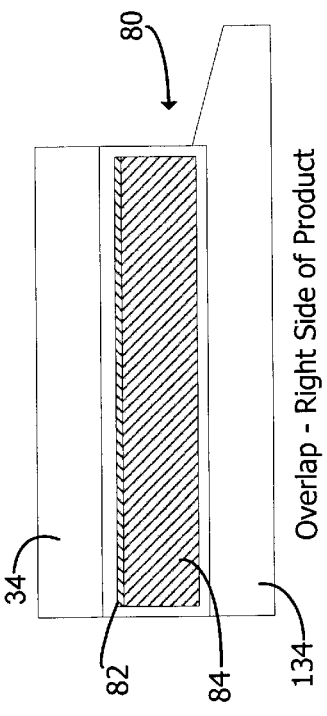
FIG. 10B
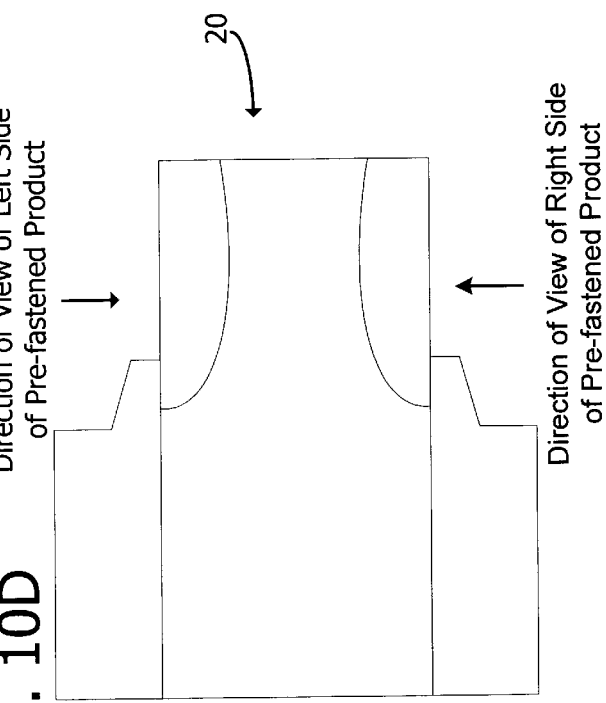
FIG. 10D
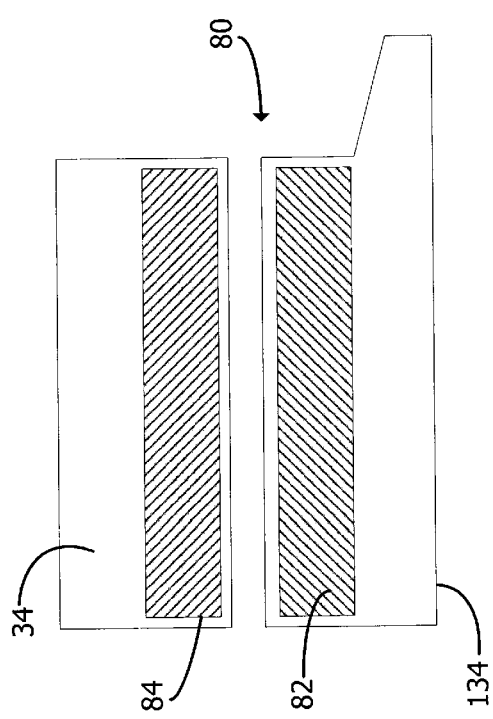
FIG. 10A
FIG. 10C

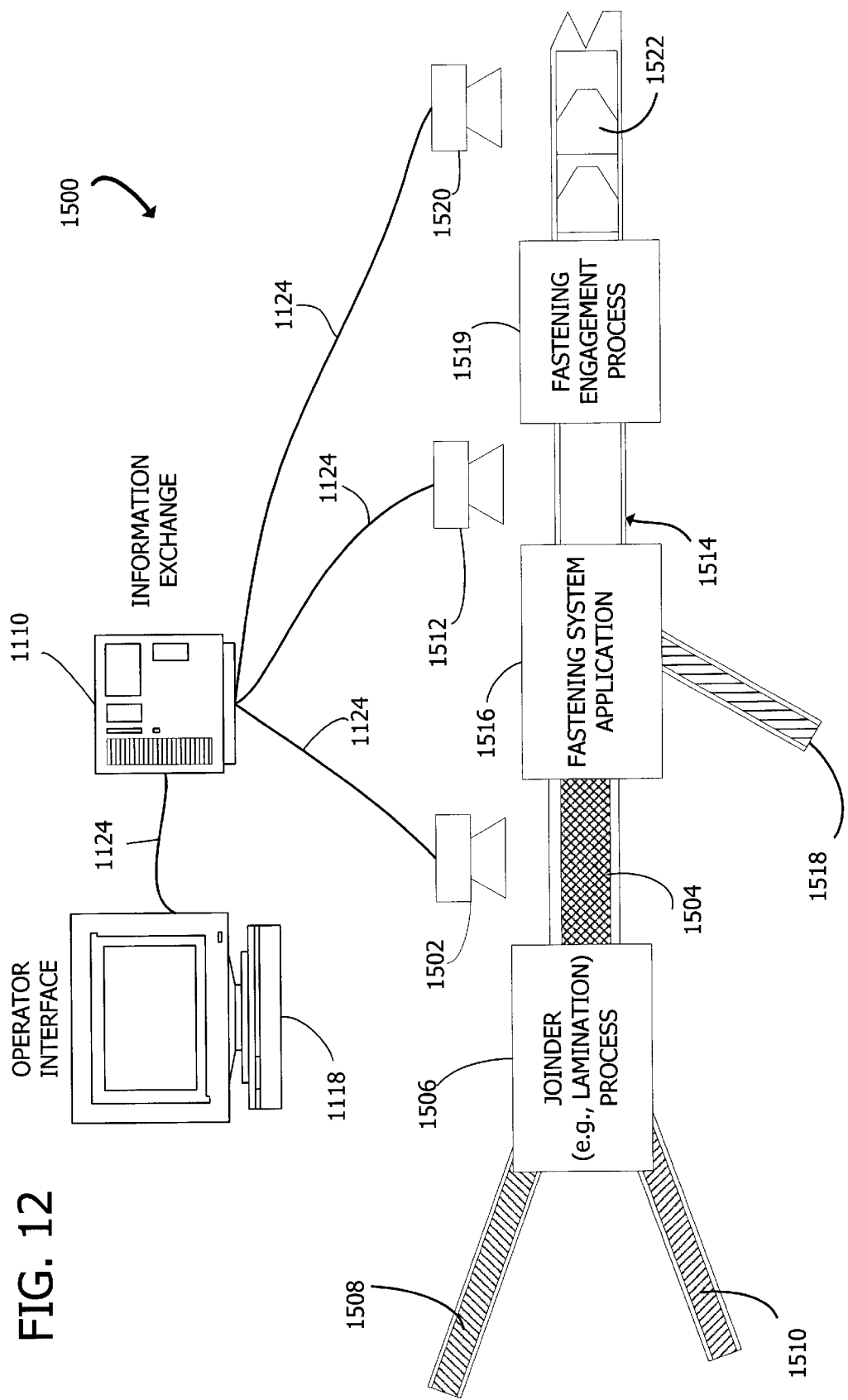

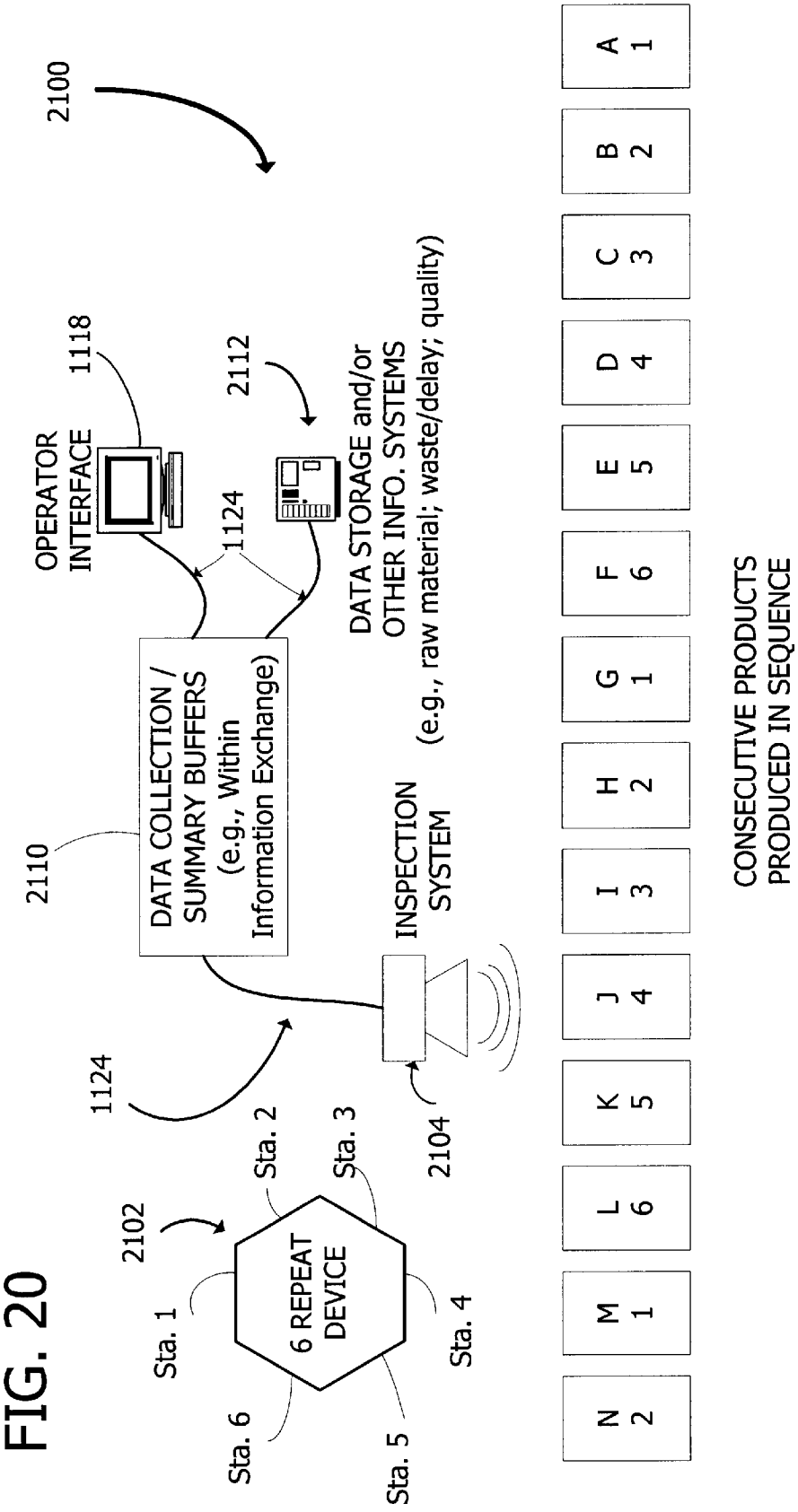

WEB GUIDING SYSTEM AND METHOD

CROSS-REFERENCE TO RELATED APPLICATION

The invention of the present application is related to and claims priority to provisional U.S. patent application Ser. No. 60/401,805, entitled INFORMATION EXCHANGE, filed on Aug. 7, 2002, the entire disclosure of which is incorporated herein by reference.

FIELD OF THE INVENTION

The present invention relates generally to systems and methods associated with inspecting composite products produced using one or more web converting manufacturing processes. More particularly, the invention relates to systems and methods for guiding one or more webs of component materials used in a web converting manufacturing process producing a composite product.

BACKGROUND OF THE INVENTION

Articles such as disposable absorbent garments have numerous applications including diapers, training pants, feminine care products, and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes. A number of such garments include fastening components which are intended to be connected together (e.g., pre-fastened) during manufacture of the garment so that the product is packaged in its fully assembled form.

For example, one such pre-fastened garment includes child's training pants, which have a central absorbent chassis and front and back side panels extending laterally out from the chassis adjacent longitudinally opposite ends thereof. A portion of each of the front and back side panels has a respective fastening component disposed thereon. During manufacture of the training pants, the central absorbent chassis is initially formed generally flat and then folded over so that the front and back side panels face each other. The respective fastening components of the front and back side panels are then aligned and connected together to define an engagement seam. Upon securing the front and back side panel fastening components together, the pre-fastened pair of training pants is in its fully assembled three-dimensional form having an interior space bounded in part by the engagement seam.

For a variety of purposes, including quality control, process control, material control, and so on, it is often desirable to monitor the presence of and/or interrelationships between one or more elements of a disposable absorbent garment. For instance, elements such as outer covers, liners, absorbent pads, side panels, elastic components, fastener components, etc. must be positioned or aligned with respect to each other and/or to other components as desired or otherwise intended in order to produce an acceptable product. Accordingly, inspection systems are commonly used to detect the presence and/or relative positions of such components during manufacturing. If an inspection system determines that one or more components are out of position and thus do not properly register with other components, the inspection system typically outputs one or more signals indicating that certain articles should be culled and discarded, that the process should be adjusted so as to bring out-of-position components into proper position, that the process should be adjusted so that subsequent components are brought into proper registration with one another, and so on.

One such registration inspection system is disclosed in U.S. Pat. No. 5,359,525, the disclosure of which is incorporated herein by reference. As described therein, registration inspection of a composite product during fabrication is accomplished by producing an image of the article and then analyzing the image to detect the relative positions of one or more components. The detected positions are then compared to desired positions to thereby determine whether one or more components are improperly positioned. Such registration inspection systems employ conventional video cameras for capturing visible, ultraviolet, x-ray, and infrared light reflected by and/or transmitted through components of the product in order to produce still video images of such components. Thus, after producing a video image of a composite article and its several components, the image can be analyzed to determine whether the components are properly positioned and registered with one another.

Although highly useful for many applications, there is a need for a higher order level of inspection and control that provides advantages with respect to the inspection, analysis and control of high speed web converting processes associated with manufacturing products having tight quality tolerances. Such products include, for example, certain products having engagement seams formed by connecting two elements together such that the engagement seam is essentially two layers. For example, engagement seams formed by connected side panels of the training pants described previously has heretofore entailed connecting the side panels in face-to-face relationships with outer edges of the side panels aligned with each other. To inspect such an engagement seam, it was necessary only to inspect the exposed outer edges of the side panels so that there was no need to actually capture an image of any underlying elements or edges of the training pants. More recent engagement seams, however, are formed by connecting the side panels in overlapping relationship so that the outer edge of one side panel underlies the other side panel at the engagement seam. Still referring to the engagement seam example, arriving at a finished state of properly engaged side seams requires a precise final positioning of the edges of the fastening system components on the side panels. Such a level of control can be accomplished through a cascaded process control of multiple (e.g., up to seven in one example) dependent product geometrical relationships that can be affected by material, process settings, process set points, transient conditions, and so on.

It is desirable to capture an image of the underlying panel at the engagement seam to determine the position and relative alignment of the outer edge of the underlying panel. Because the light emitting source and camera of the inspection system described in U.S. Pat. No. 5,359,525 are positioned exterior of the inspected component, it is difficult to inspect the outer edge of an underlying panel of the more recent engagement seams once the panels are connected. For example, it is difficult to lay the engagement seam flat over the light emitting source of the disclosed inspection system, thereby increasing the risk that the image captured by the camera will appear fuzzy. Moreover, it is difficult for the Moreover, prior art systems for inspecting composite articles, such as, for example, disposable absorbent garments, do not integrate and relate data from multiple inspection stations to prioritize necessary or desirable automatic control actions, trouble-shooting actions/recommendations, operator alarming, and so on.

Further, prior art systems for inspecting composite articles, such as disposable absorbent garments, did not integrate and relate information/data from multiple inspections systems with information from other information systems associated with a manufacturing process. For example, database systems have been employed for collecting waste/delay/productivity information, raw material information, manually entered quality information (e.g., from manual inspections of selected items), and machine process information. In fabricating articles such as diapers and training pants, such information includes productivity associated with a particular production run, various attributes of the raw materials used, process control settings (e.g., vacuum settings, machine set points, conveyor steering commands, and so on), and the like. Such prior art information, however, has not been correlated to inspection information so that improvements can be made, for example, to further reduce cost and waste, and to increase productivity and quality.

Improvements are also desired with respect to information systems associated with web converting processes. For example, web converting manufacturing processes often use multiple station devices, with each station performing a substantially similar function. Prior art information systems do not adequately isolate and exploit inspection data associated with a particular station of such multiple station devices. It has been known to use simple photoeye detectors to detect whether a side panel placed by a multiple station device was present on the absorbent article constructed using that device. Identifying and exploiting additional aspects of multiple station devices, however, is desirable.

SUMMARY OF THE INVENTION

In one form, the invention comprises a web guiding system suitable for use in connection with a continuous production line producing a composite web from two or more web components on a feed system. A vision inspection system captures an image of the composite web and detects in the captured image a relative placement of a first web component of the composite web to a second web component of the composite web. The vision inspection system provides to the communication network an inspection parameter indicative of the detected relative placement. An information exchange system obtains via a communication network a plurality of inspection parameters, each associated with one of a plurality of composite webs. The information exchange system determines a mathematical characteristic of the obtained plurality of inspection parameters and provides the mathematical characteristic via the communication network. A drive system adjusts a position of the feed system. The drive system obtains the provided mathematical characteristic and compares the mathematical characteristic to a target. The drive system selectively adjusts the position of the feed system as a function of a difference between the mathematical characteristic and the target.

In another form, the invention comprises a web guiding system suitable for use in connection with a continuous production line producing a composite web from two or more web components on a feed system. A vision inspection system captures an image of the composite web and detects in the captured image a relative placement of a first web component of the composite web to a second web component of the composite web. The vision inspection system provides to the communication network an inspection parameter indicative of the detected relative placement. An information exchange system obtains via a communication network a plurality of inspection parameters, each associated with one of a plurality of composite webs. The information exchange system determines a mathematical characteristic of the obtained plurality of inspection parameters and provides the mathematical characteristic via the communication network. A drive system adjusts a position of the feed system. The drive system obtains the provided mathematical characteristic and compares the mathematical characteristic to a target, the drive system selectively adjusting the position of the feed system as a function of a predictive information correlated to the mathematical characteristic and the target.

In another form, the invention comprises a system suitable for use in connection with a continuous production line producing a composite web from two or more web components on a feed system. A vision inspection system captures an image of the composite web and detects in the captured image a relative placement of a first web component of the composite web to a second web component of the composite web. The vision inspection system provides to the communication network an inspection parameter indicative of the detected relative placement. An information exchange system obtains via the communication network a plurality of inspection parameters, each associated with one of a plurality of composite webs. The information exchange system determines a mathematical characteristic of the obtained plurality of inspection parameters and provides the mathematical characteristic via the communication network. A drive system adjusts a position of the production line relative to the feed system. The drive system obtains the provided mathematical characteristic and compares the mathematical characteristic to a target. The drive system selectively adjusts the production line as a function of a difference between the mathematical characteristic and the target.

In another form, the invention comprises a web guiding system suitable for use in connection with a continuous production line producing a composite web formed from two or more web components on a feed system. A vision inspection system captures an image of the composite web formed from first and second web components and detects in the captured image a relative placement of the first web component to the second web component. The vision inspection system provides to the communication network an inspection parameter indicative of the detected relative placement. An information exchange system obtains via the communication network a plurality of inspection parameters, each associated with one of a plurality of composite webs. The information exchange system determines a mathematical characteristic of the obtained plurality of inspection parameters and determines an amount to adjust the feed system as a function of the determined mathematical characteristic. The information exchange system provides an adjustment parameter corresponding to the determined amount to adjust the feed system. A drive system responsive to the adjustment parameter selectively adjusts the feed system.

In another form, the invention comprises a system suitable for use in connection with a continuous production line producing a composite web formed from two or more web components on a feed system. A vision inspection system captures an image of the composite web formed from first and second web components and detects in the captured image a relative placement of the first web component to the second web component. The vision inspection system provides to a communication network an inspection parameter indicative of the detected relative placement. An information exchange system obtains via the communication network a plurality of inspection parameters, each associated with one of a plurality of composite webs. The information exchange system determines a mathematical characteristic of the obtained plurality of inspection parameters and determines an amount to adjust the feed system as a function of the determined mathematical characteristic. The information exchange system provides an adjustment parameter corresponding to the determined amount to adjust the feed system. A drive system responsive to the adjustment parameter selectively adjusts the production line relative to the feed system.

In another form, the invention comprises a web guiding method, suitable for use in connection with a production line producing a composite product from a first web component combined with a second web component. The method comprises:

capturing an image of the first and second components after combining the first and second web components;

detecting in the captured image a placement of the first web component relative to the second web component;

providing an inspection parameter indicative of the placement of the first web component relative to the second web component;

obtaining a plurality of inspection parameters, each associated with one of a plurality of composite products;

determining a mathematical characteristic of the obtained plurality of inspection parameters;

comparing the mathematical characteristic to a target; and selectively adjusting a drive set point associated with providing the first web component prior to combination with the second web component as a function of a difference between the mathematical characteristic and the target.

In another form, the invention comprises a web guiding method, suitable for use in connection with a production line producing a composite product from a first web component combined with a second web component. The method comprises:

capturing a first image of the first and second components after combining the first and second web components;

detecting in the first captured image a first placement of the first web component relative to the second web component;

capturing a second image of the first and second components after combining the first and second web components;

detecting in the second captured image a second placement of the first web component relative to the second web component;

comparing the first placement to the second placement to identify an amount indicative of a relative placement of the first and second web components;

providing an inspection parameter indicative of the indicative amount between the first and second web components;

obtaining a plurality of inspection parameters, each associated with one of a plurality of composite products;

determining a mathematical characteristic of the obtained plurality of inspection parameters;

comparing the mathematical characteristic to a target; and selectively adjusting a drive set point associated with providing the first web component prior to combination with the second web component as a function of a difference between the mathematical characteristic and the target.

In another form, the invention comprises a method, suitable for use in connection with a production line producing a composite product from a first web component combined with a second web component. The method comprises:

capturing an image of the first and second components after combining the first and second web components;

detecting in the captured image a placement of the first web component relative to the second web component;

providing an inspection parameter indicative of the placement of the first web component relative to the second web component;

obtaining a plurality of inspection parameters, each associated with one of a plurality of composite products;

determining a mathematical characteristic of the obtained plurality of inspection parameters;

comparing the mathematical characteristic to a target; and selectively adjusting a parameter of the production line prior to combination with the second web component as a function of a difference between the mathematical characteristic and the target.

In another form, the invention comprises a web guiding method suitable for use in connection with a continuous production line producing a composite web from two or more web components on a feed system. The method comprises:

capturing an image of the composite web;

detecting in the captured image a relative placement of a first web component of the composite web to a second web component of the composite web;

providing to a communication network an inspection parameter indicative of the detected relative placement;

obtaining via the communication network a plurality of inspection parameters, each associated with one of a plurality of composite webs;

determining a mathematical characteristic of the obtained plurality of inspection parameters;

providing the mathematical characteristic via the communication network;

adjusting a position of the feed system;

obtaining the provided mathematical characteristic;

comparing the mathematical characteristic to a target; and selectively adjusting the position of the feed system as a function of a predictive information correlated to the mathematical characteristic and the target.

DEFINITIONS

Within the context of this specification, each term or phrase below will include, but will not be considered necessarily limited to, the following meaning or meanings.

"Bonded" comprises the joining, adhering, connecting, attaching, or the like, of two elements. Two elements will be considered to be bonded together when they are bonded directly to one another or indirectly to one another, such as when each is directly bonded to intermediate elements.

"Connected" comprises the joining, adhering, bonding, attaching, or the like, of two elements. Two elements will be considered to be connected together when they are connected directly to one another or indirectly to one another, such as when each is directly connected to intermediate elements.

"Culled" articles includes articles that are discarded during the manufacturing process, prior to being packaged. For example, an article may be culled if an inspector identifies an unacceptable nonconforming characteristic. An article may be culled before its construction has been completed.

"Disposable" comprises articles which are designed to be discarded after a limited use rather than being laundered or otherwise restored for reuse.

"Disposed," "disposed on," and variations thereof are intended to include that one element can be integral with another element, or that one element can be a separate structure bonded to or placed with or placed near another element.

"Elastic," "elasticized" and "elasticity" include that property of a material or composite by virtue of which it tends to recover its original size and shape after removal of a force causing a deformation.

"Elastomeric" comprises a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Endseal" is an edge of two or more panels that are joined together by adhesive or other means. In the context of an absorbent article, a front end seal includes a front distal edge of an absorbent panel and a distal edge of a right front elastic side panel and/or a front distal edge of an absorbent panel and a distal edge of a left front elastic side panel. In the context of an absorbent article, a rear end seal includes a rear distal edge of an absorbent panel and a distal edge of a right rear elastic side panel and/or a rear distal edge of an absorbent panel and a distal edge of a left rear elastic side panel.

"Fabrics" is used to include all of the woven, knitted and nonwoven fibrous webs.

"Flexible" comprises materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" comprises any design, pattern, or the like that is visible on an absorbent article.

"Hydrophilic" comprises fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" comprises various portions of a single unitary element rather than separate structures bonded to or placed with or placed near one another.

"Inward" and "outward" comprise positions relative to the center of an absorbent article, and particularly transversely and/or longitudinally closer to or away from the longitudinal and transverse center of the absorbent article.

"Layer" when used in the singular can have the dual meaning of a single element or a plurality of elements. "Liquid impermeable", when used in describing a layer or multi-layer laminate, includes that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" comprise their customary meaning. The longitudinal axis lies in the plane of the garment and is generally parallel to a vertical plane that bisects a standing wearer into left and right body halves when the article is worn. The transverse axis lies in the plane of the article generally perpendicular to the longitudinal axis. The garment as illustrated is longer in the longitudinal direction than in the transverse direction.

"Mathematical characteristic" includes determinations made by mathematical manipulation, as well as statistical determinations, manipulations and assessments of variability of data sets such as, for example, a range or indication of a range of values within a data set, a variance, or a coefficient of variance.

"Member" when used in the singular can comprise the dual meaning of a single element or a plurality of elements.

"Nonwoven" and "nonwoven web" comprise materials and webs of material which are formed without the aid of a textile weaving or knitting process. "Operatively joined," with reference to the attachment of an elastic member to another element, includes that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" comprises a graphic that is directly visible upon inspection of the exterior surface of a garment, and for a refastenable garment is in reference to inspection of the exterior surface of the garment when the fastening system is engaged as it would be during use.

"Permanently bonded" comprises the joining, adhering, connecting, attaching, or the like, of two elements of an absorbent garment such that the elements tend to be and remain bonded during normal use conditions of the absorbent garment.

"Refastenable" comprises the property of two elements being capable of releasable attachment, separation, and subsequent releasable reattachment without substantial permanent deformation or rupture.

"Releasably attached," "releasably engaged" and variations thereof comprise two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" includes the breaking or tearing apart of a material; in tensile testing, the term comprises the total separation of a material into two parts either all at once or in stages, or the development of a hole in some materials.

"Stretch bonded" comprises an elastic member being bonded to another member while the elastic member is extended at least about 25 percent of its relaxed length. Desirably, the term "stretch bonded" comprises the situation wherein the elastic member is extended at least about 100 percent, and more desirably at least about 300 percent, of its relaxed length when it is bonded to the other member.

"Stretch bonded laminate" comprises a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language or by additional examples in the remaining portions of the specification, and also encompass their ordinary and customary meaning(s).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 4A is a block diagram of an inspection system having an information exchange;

FIGS. 5A and 5B are logic flow diagrams illustrating one method of providing real time quality, suitable for use in connection with an inspection system such as that illustrated in FIG. 4A;

FIGS. 10A–10D illustrate schematically a fastening system associated with the refastenable child's training pants illustrated in FIGS. 1–3;

FIG. 12 is a schematic representation of an exemplary automated trouble-shooting system, suitable for use in connection with an information system such as that illustrated in FIG. 4A;

FIG. 20 illustrates in schematic form a system for tracking per station information from a multiple station manufacturing device;

DETAILED DESCRIPTION OF THE DRAWINGS

The methods and apparatus of the present invention can be used to make a variety of articles such as disposable absorbent garments including diapers, training pants, feminine hygiene products, incontinence products, other personal care or health care garments, swim pants, athletic clothing, pants and shorts, and the like. As an example, the methods and apparatus of the present invention can be used to make articles in which at least two elements of the article are connected together during the making thereof to assemble or "pre-fasten" the article. For ease of explanation, the methods and apparatus of the present invention are hereafter described in connection with making pre-fastened child's training pants, generally indicated as 20 in FIG. 1. In particular, the methods and apparatus will be described in terms of those for making pre-fastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Training pants 20 can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

Figure 1:
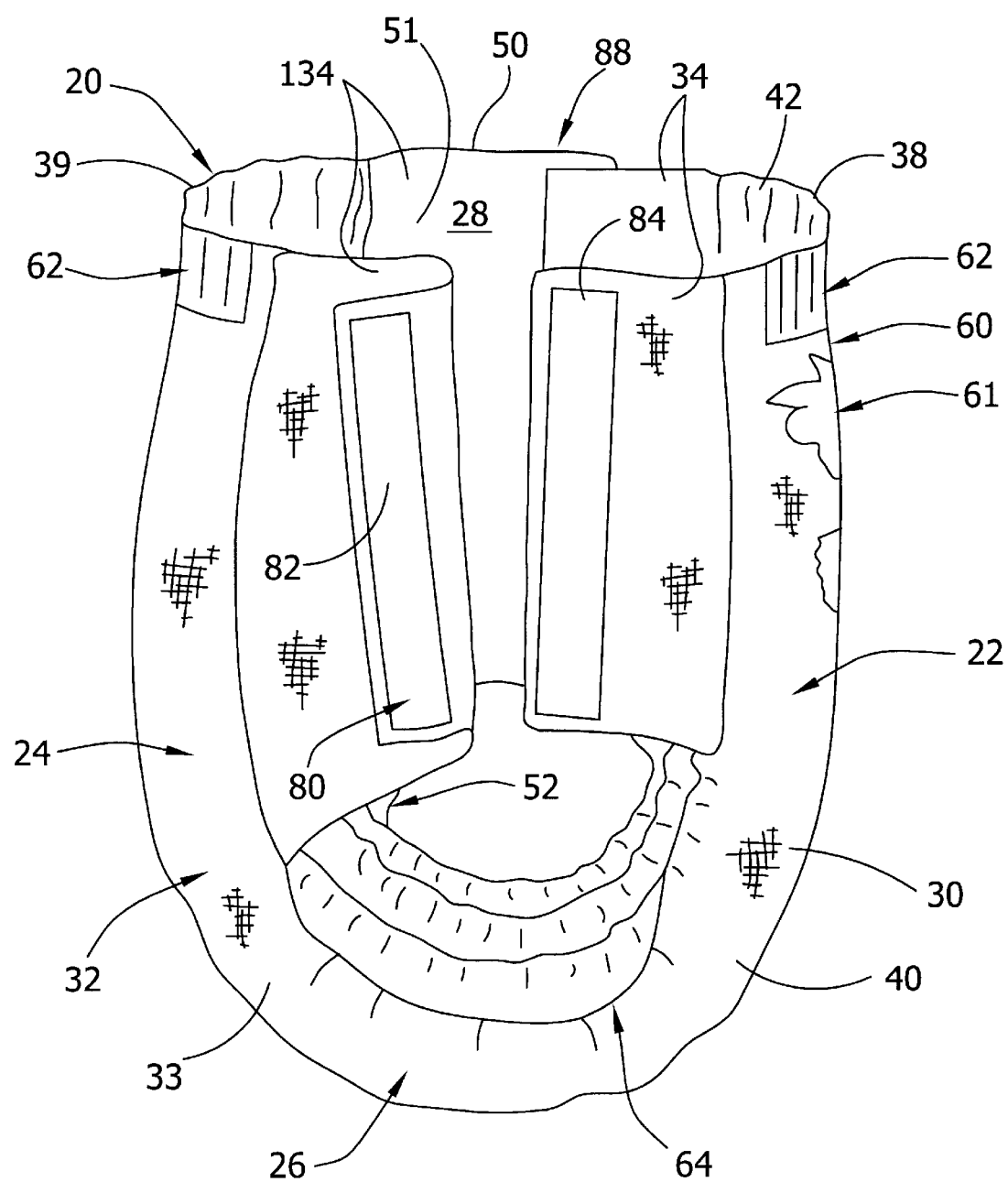
FIG. 1 is a side elevation of a child's training pants with a fastening system of the training pants shown connected on one side of the training pants and disconnected on the other side of the training pants.

With reference now to the drawings, and in particular to FIG. 1, the training pants 20 are illustrated in a partially fastened condition and comprise an absorbent chassis 32 having a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
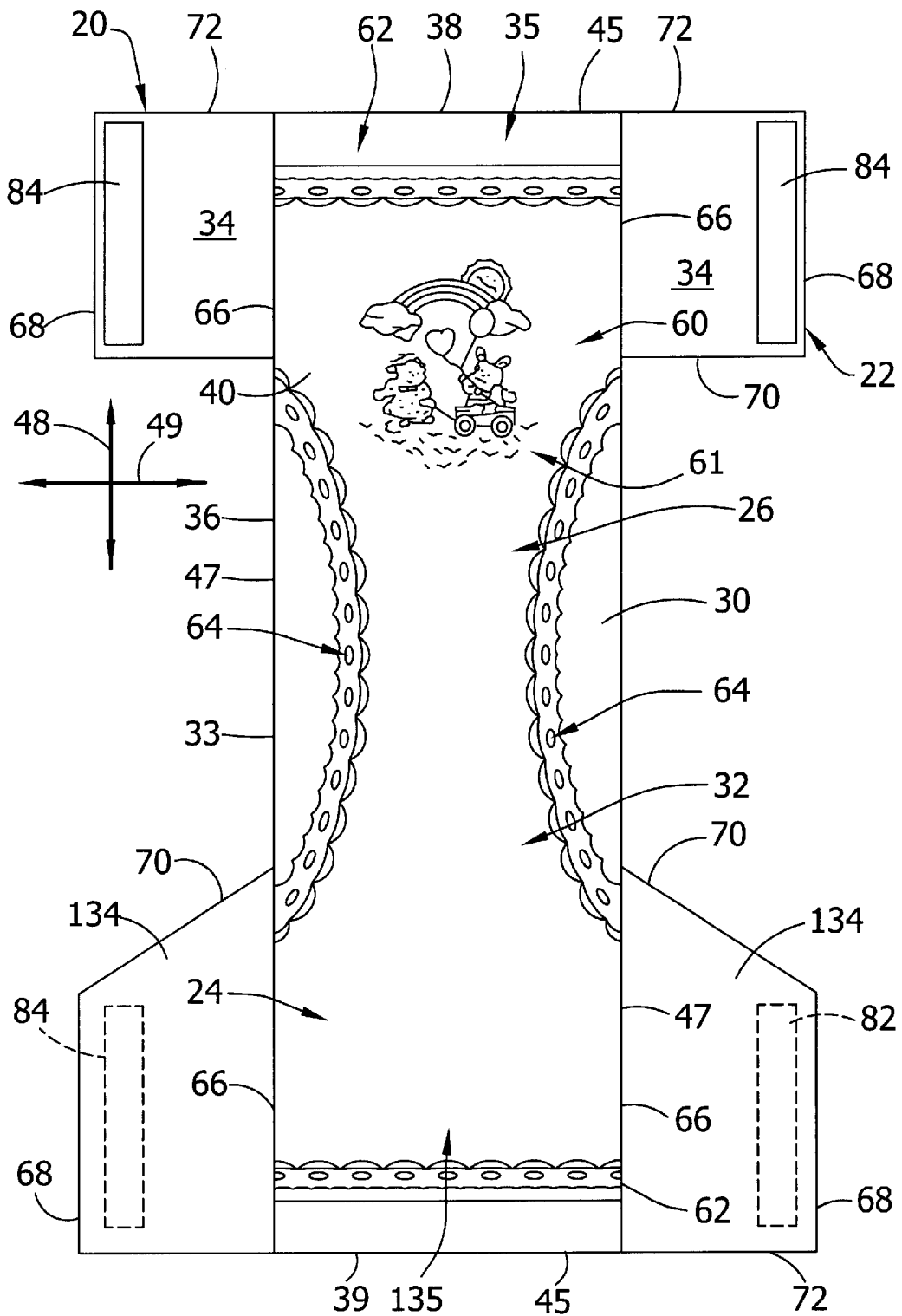
FIG. 2 is a bottom plan view of the training pants of FIG. 1 in an unfastened, stretched and laid flat condition to show an outer surface of the training pants which faces away from the wearer.
Figure 3:
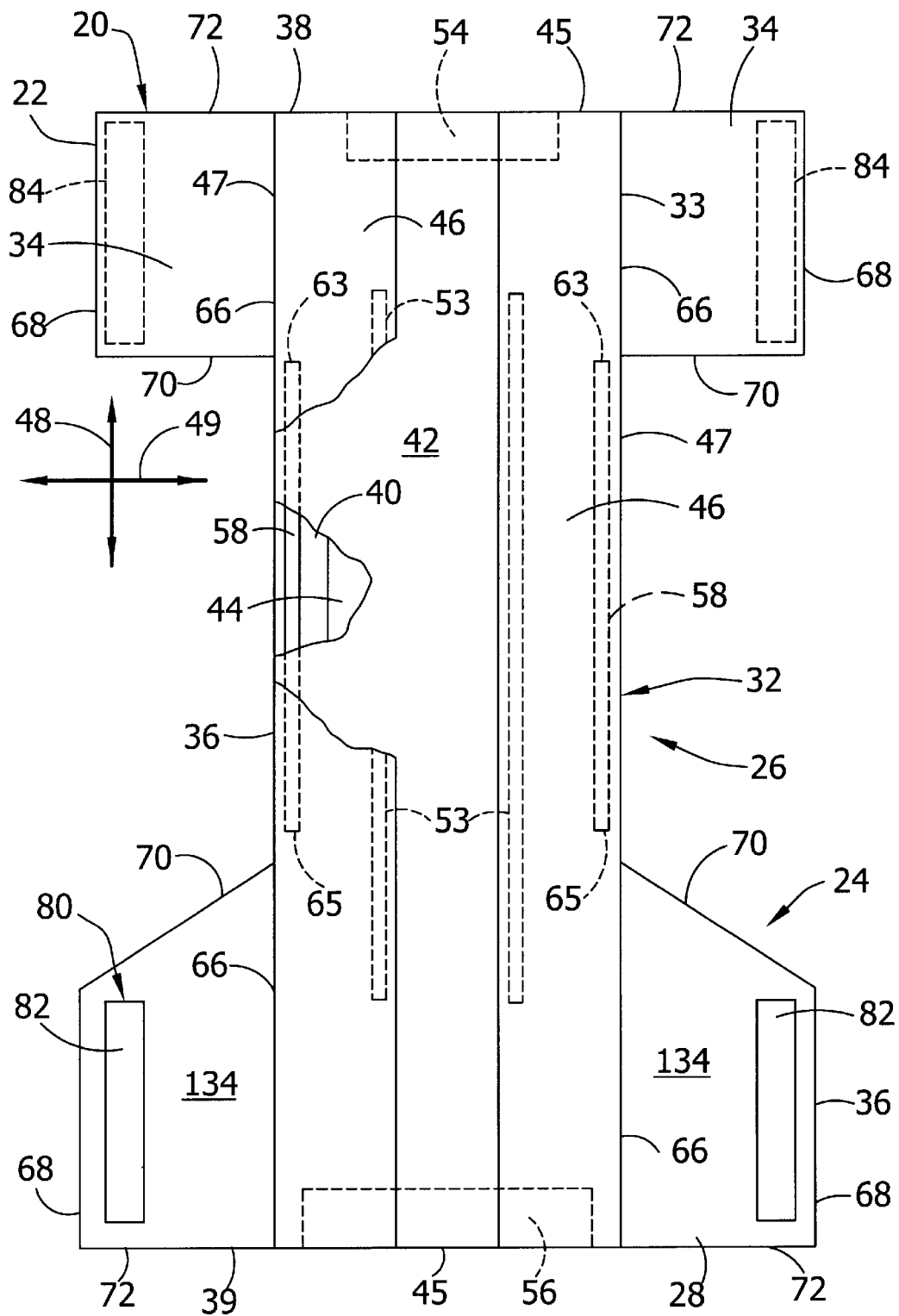
FIG. 3 is a top plan view of the training pants in its unfastened, stretched and laid flat condition to show an inner surface of the training pants which faces the wearer when the training pants are worn, with portions of the training pants being cut away to reveal underlying features.

The illustrated absorbent chassis 32 comprises a composite structure 33 (FIG. 3), which when laid flat can be rectangular or any other desired shape, and has a pair of laterally opposite front side panels 34 and a pair of laterally opposite back side panels 134 extending outward therefrom. The composite structure 33 and side panels 34, 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and could define a one-piece elastic, stretchable, or nonstretchable pants. The illustrated composite structure 33 comprises an outer cover 40, a bodyside liner 42 (FIGS. 1 and 3) connected to the outer cover in a superposed relation, an absorbent assembly 44 (FIG. 3) disposed between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having an interior space 51, a waist opening 50 for receiving the wearer into the interior space of the pants, a pair of leg openings 52 and engagement seams 88 along which the side panels are connected. The interior space 51 of the pants 20 is thus bounded by the absorbent chassis 32, the engagement seams 88 and the portions of the side panels 34, 134 extending on opposite sides of the engagement seams 88 (e.g., between the engagement seams and the absorbent chassis. As used herein, the "interior space" 51 is intended to refer to the space between any two portions of a three-dimensional article which generally oppose each other. It is understood that a transverse cross-section of the article need not be closed, e.g., continuous, to define an interior space. For example, a two-dimensional article may be generally folded over on itself so that two portions of the article oppose each other to define an interior space of the article therebetween. Thus, the interior space 51 of the training pants 20 shown in FIG. 1 may be defined by the side panels 34, 134 themselves or, if the side panels were fully straightened therebetween, the interior space would be defined by a combination of the side panels and the front and back waist regions 22, 24 of the absorbent chassis 32.

The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. 1. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene non-woven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

If the outer cover 40 is a single layer of material, it can be embossed and/or matte finished to provide a more cloth-like appearance. As earlier mentioned, the liquid impermeable material can permit vapors to escape from the interior space 51 of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of training pants 20 is designed for use by young girls and includes a registered outer cover graphic 60 (FIG. 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants can comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in training pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the attachment line 66 to the outer edge 68, as is best shown in FIGS. 2 and 3.

Each of the side panels 34, 134 can include one or more individual, distinct pieces of material. In particular embodiments, for example, each side panel 34, 134 can include first and second side panel portions that are joined at a seam, or can include a single piece of material which is folded over upon itself (not shown).

The side panels 34, 134 desirably although not necessarily comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes first fastening components 82 adapted for refastenable engagement to corresponding second fastening components 84. In one embodiment, one surface of each of the first fastening components 82 comprises a plurality of engaging elements which project from that surface. The engaging elements of the first fastening components 82 are adapted to repeatedly engage and disengage engaging elements of the second fastening components 84.

The fastening components can comprise separate elements bonded to the side panels, or they may be integrally formed with the side panels. Thus, unless otherwise specified, the term "fastening component" includes separate components which function as fasteners, and regions of materials such as the side panels which function as fasteners. Moreover, a single material can define multiple fastening components to the extent that different regions of the material function as separate fasteners. The fastening components 82, 84 can be located on the side panels, between the side panels such as on the absorbent chassis, or a combination of the two.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

The refastenable fastening system 80 allows for easy inspection of the interior space 51 of the pants 20. If necessary, the fastening system 80 also allows the pants 20 to be removed quickly and easily. This is particularly beneficial when the pants contain messy excrement. For training pants 20, the caregiver can completely remove the pant-like product and replace it with a new one without having to remove the child's shoes and clothing.

In the illustrated embodiment, the first fastening components 82 comprise hook fasteners and the second fastening components 84 comprise complementary loop fasteners. In another particular embodiment, the first fastening components 82 comprise loop fasteners and the second fastening components 84 comprise complementary hook fasteners. Alternatively, the fastening components 82, 84 can comprise interlocking similar surface fasteners, adhesive or cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height, a greater percentage of directionally-aligned hooks, or a more aggressive hook shape.

Loop fasteners typically comprise a fabric or material having a plurality of loop members extending upwardly from at least one surface of the structure. The loop material can be formed of any suitable material, such as acrylic, nylon, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook fasteners typically comprise a fabric or material having a base or backing structure and a plurality of hook members extending upwardly from at least one surface of the backing structure. In contrast to the loop fasteners which desirably comprise a flexible fabric, the hook material advantageously comprises a resilient material to minimize unintentional disengagement of the fastener components as a result of the hook material becoming deformed and catching on clothing or other items. The term "resilient" as used herein comprises an interlocking material having a predetermined shape and the property of the interlocking material to resume the predetermined shape after being engaged and disengaged from a mating, complementary interlocking material. Suitable hook material can be molded or extruded from nylon, polypropylene or another suitable material. Suitable single-sided hook materials for the fastening components 82, 84 are available from commercial vendors such as Velcro Industries B. V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 3, the fastening components 82 are disposed on the inner surface 28 of the back side panels 134. The fastening components 82 are desirably positioned along the outer edges 68 of the back side panels 134, and abutting or adjacent to the waist end edge 72. In certain embodiments, for example, the fastening components 82 can be located within about 2 centimeters, and more particularly within about 1 centimeter, of the outer edges 68, the waist end edges 72, and the leg end edges 70. With particular reference to FIG. 2, the second fastening components 84 are disposed on the outer surface 30 of the front side panels 134. The second fastening components 84 are sized to receive the first fastening components 82 and are desirably positioned along the outer edges 68 of the front side panels 34, and abutting or adjacent to the waist end edge 72. As an example, the second fastening components 84 can be located within about 2 centimeters, and more particularly within about 1 centimeter, of the outer edges 68, the waist end edges 72, and the leg end edges 70. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 84, 82 can be adhered to the respective side panels 34, 134 by any means known to those skilled in the art such as adhesive bonds, ultrasonic bonds or thermal bonds. The fastening components 82, 84 may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components 82, 84 can comprise integral portions of the waist regions 24, 22. For instance, one of the elastomeric front or back side panels 34, 134 can function as second fastening components 84 in that they can comprise a material which is releasably engageable with fastening components 82 disposed in the opposite waist region.

The fastening components 82, 84 of the illustrated embodiments are rectangular, although they may alternatively be square, round, oval, curved or otherwise non-rectangularly shaped. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 5 to about 13 centimeters, such as about 10 centimeters, and the width is desirably from about 0.5 to about 3 centimeters, such as about 1 centimeter. With particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

As shown in FIG. 1, when the fastening components 82, 84 are releasably connected, the side edges 36 of the absorbent chassis 32 in the crotch region 26 define the leg openings 52, and the waist edges 38 and 39 of the absorbent chassis, including the waist end edges 72 of the side panels 34, 134, define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When connected, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 75 to 100 percent, and particularly about 90 to about 98 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 80 to 100 percent, and more particularly about 90 to about 98 percent, of the distance between the waist end edge 70 and the leg end edge 72 of the side panels 34, 134. In other embodiments, the fastening components can comprise a plurality of smaller fastening elements covering a smaller portion of the distance between the waist opening 50 and the leg openings 52, but spaced apart to span a large distance between the waist opening and the leg openings.

For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between a set of fastening components 82, 84 is measured parallel to the transverse axis 49 between the longitudinal center lines of the fastening component, measured with the side panels 34, 134 in an unstretched condition.

FIG. 4A is a block diagram of an information system 1100, suitable for use in connection with a continuous production line 1102 manufacturing composite products such as, for example, the above-described training pants or other disposable absorbent garments. Such articles are generally fabricated using high speed web converting processes. For example, some articles are fabricated at speeds in excess of 300 products/minute, and some articles may be fabricated at speeds in excess of 500 products/minute, by a converting process that includes a sequential addition of component parts (e.g., web materials, graphics, elastic components, and so on) during a production run. It should be understood that articles may be fabricated in accordance with the systems and methods described herein at lower or higher speeds, the foregoing being provided for exemplary purposes.

In one aspect, the system comprises an inspection system 1104 having a plurality of inspection devices (identified generally in FIG. 4A as reference character 1106) positioned at various places along the production line 1102 to inspect different components of each composite product produced. In the illustrated embodiment, the inspection devices 1106 preferably comprise CCD cameras, such as Sony CCD cameras, part No. XC-75, coupled to one or more machine vision inspection systems, such as a Cognex 8120 series processor running Checkpoint® III software, available from Cognex Corporation, of Natick, Mass., U.S.A. An advantage of such an inspection system is that it provides a processor for vision system purposes and another processor for networking purposes.

As a particular example, two such cameras coupled to a Cognex 8120 series processor running Checkpoint® III software can be used to inspect the amount of overlap between fastening components 82, 84, of fastening system 80 used in connection with the above-described training pants, at or near the leg and waist extremes of fastening system 80 (FIGS. 1–3). More particularly, one camera is positioned to capture an image of fastening system 80 as completed (e.g., first and second fastening components 82, 84 being engaged) on the left side of the product. A second camera is positioned to capture an image of fastening system 80 on the right side of the product at substantially the same time. The inspection system (which could be any type of examination system including a SICK detector, photoeye, proximity switch or machine vision system) determines an amount of overlap between fastening components 82 and 84 for each side of the product.

Further, and as is generally known in the art, machine vision systems, such as the Cognex 8120 series processor and Checkpoint® III software use machine vision "tools" to determine an inspection parameter. In this example, the inspection parameter comprises an amount of overlap between two fastening components during the manufacture of a training pant. The tools are configured, again as is known in the art, to detect edges on the basis of gray scale differences within a region of captured images. Preferably, the machine vision system is configured to provide an indication of when it senses an error or failure of its tools (e.g., the object to be inspected is not present or there is insufficient gray scale signal strength due to poor contrast resulting from material variability, lighting variability, presentation of the object to the camera lens, and/or camera focus/aperture settings). In such case, the machine vision system may or may not provide an inspection parameter, but it is preferable that such system provides an indication of the existence of an inspection failure (such as a tool failure) so that any data can be addressed accordingly (e.g., data relating to an incomplete/inaccurate inspection or a failed tool may be discarded, ignored, or discounted in value).

It should be appreciated and understood that the foregoing discussion regarding inspecting fastening components 82 and 84 is provided for exemplary purposes. Other inspection systems, cameras, and methodologies are compatible with the present disclosure.

Depending upon placement, machine vision inspection systems provide an ability to detect substantially all points on all products produced, and allow for image processing of the detected points.

Other inspection devices 1108 may also be used in connection with information system 1100. Such other inspection devices 1108 include a number of suitable devices, and should be selected according to the particular inspection need. For example, it has been found to be advantageous to employ edge detection inspection devices, such as Part No. 85427-002, available from Fife Corporation, Oklahoma City, OKla., U.S.A., in order to detect the edges of moving webs and for guiding such moving webs in a desired path. Other inspection devices include photoeye sensors (e.g., MAXIBEAM® photoeyes, available from Banner Engineering Corporation, Minneapolis, Minn., U.S.A.), and UV sensors, such as UV photoeye sensors (e.g., LUT1-4 series luminescence sensors, available from Sick, Inc., Bloomington, Minn., U.S.A.).

As an example, it is also contemplated that product spacing information may be detected and tracked by photoeyes. For example, after the final cut off (where the continuous web of pants is cut into individual pants), the training pants are discrete objects flowing through the folding, fastening, side panel tucking, and cull processes. Because of the timing of these processes, there may be a need to maintain consistent pant-to-pant spacing. In this case, photoeyes may be installed to monitor the pant spacing at several locations after the final cut off.

In one embodiment, an information exchange 1110 is connected to receive inspection data from inspection system 1104. Preferably, the information exchange 1110 is also connected to one or more manufacturing-related databases and systems such as, for example, a quality system 1112, a machine set point database 1114, a registration control system 1116, an operator display/interface 1118, a waste/delay database 1120, or a raw material database 1122.

The information exchange 1110 preferably comprises a computer system. More particularly, in one such an embodiment, information exchange 1110 comprises a personal computer (PC) running SoftLogix™ v.10, available from Rockwell Automation. Advantageously, such a configuration allows the PC to operate as a "soft" PLC. Information exchange 1110 further comprises a SoftLogix™ controller running RSLogix™ 5000 software, which is substantially the same programming software used for ControlLogix™. These products are also available from Rockwell Automation. The RSLogix™ 5000 program reads inspection measurements off of an information network (e.g., a distributed node, shared memory system such as the REFLECTIVE MEMORY network described below). It should be understood that such a computer system is thereafter programmed to perform the specific functions desired. For example, and as will be appreciated from the descriptions that follow, in one embodiment dynamic link libraries ("DLL's" which may be written in the C programming language) are used to perform desired statistical/mathematical calculations and to read/write information to reflective memory. Processor speed should be selected on the basis of the volume of information and how often the information is provided/updated. For example, when inspecting training pants, which are preferably manufactured at high converting speeds, high processing speeds are desirable (especially if data is gathered for each product produced during a production run). In particular, information exchange 1110 is configured to perform one or more of the following exemplary tasks:

monitor/receive inspection data regarding substantially all products produced during a production run or a sample set thereof;

determine relevant mathematical characteristics of the inspection data, including determining averages and standard deviations;

filter inspection data, for example, to eliminate clearly out-of-bounds data (e.g., compare to upper and/or lower limits), or to eliminate inspection data reflecting errors of machine vision tools associated with the inspection system;

compare inspection data (and/or the mathematical characteristics of such data) to targets/tolerances/limits and to monitor trends;

publish inspection data, mathematical characteristics of such data, or the results of comparing such data to targets for use by other manufacturing systems or for storage;

generate quality reports;

generate machine set point changes and registration control set point changes;

generate troubleshooting recommendations;

provide inspection data and/or mathematical characteristics of such data for use by other systems to accomplish one or more of the above exemplary tasks;

provide machine direction registration control (e.g., in the direction of product flow through the machine); and/or provide registration control in a cross direction (e.g., perpendicular to the machine direction.

It should be further understood that multiple information exchanges can be used to achieve additional levels of distribution of processing.

In one embodiment, each of the above described systems and databases is connected to a communication network 1124. Preferably, the communication network 1124 comprises a distributed node, shared memory system wherein camera inspection system 1104, information exchange 1110, quality system 1112, machine set point database 1114, registration system 1116, operator interface 1118, waste/delay database 1120, and/or raw material database 1122 comprise distributed nodes of the network. One suitable distributed node, shared memory network system is commercially available from Encore Real Time Computing, Inc., under the mark REFLECTIVE MEMORY System (RMS™). In such a system, applications write relevant data to a local memory and the REFLECTIVE MEMORY hardware facilitates transfer of the data to the local memory of the other nodes, at extremely high speeds. The high speed and high bandwidth characteristics of such a system permits real time usage of inspection data developed by inspection system 1104, as well as other data available to information system 1100. In an alternative embodiment, each of the various systems are directly connected, as reflected by the dashed lines in FIG. 4A. In still another embodiment, communication between the systems comprises the use of both direct connections, as well as communication network 1124. The foregoing communications may be over wired connections, wireless connections, or partially wired and partially wireless connections.

The operation of information system 1100 will now be described in connection with several advantageous operational configurations. Other operational aspects will become apparent in the context of certain methods suitable for use in connection with system 1100, which are described below.

Real Time Quality System

In one aspect, information system 1100 is useful for providing a real time quality data information system for use in connection with manufacturing disposable absorbent garments, manufactured by the sequential addition of component parts (including web materials). For simplicity, the operation will be described in terms of inspecting training pants, such as those illustrated and described with respect to FIGS. 1–3. In general, inspection system 1104 inspects a plurality of quality aspects of each (or a statistical sample) training pant produced during a given production run. For example, inspection systems 1104 and 1108 detect a measurement of a placement of a component (e.g., relative to another component). One specific example of such a measurement is a measurement of an overlap between hook and loop components of refastenable fastening system 80 of each training pant produced. Such a measurement may be provided by an optical detection system although other types of measurements (e.g., flow, temperature, pressure, etc.) may be made by other types of inspection and/or detection systems (e.g., flow meters, temperature sensors, pressure transducers, etc.). As a further example, such measurements and such systems may be used for process setting checks.

An inspection parameter is thereafter published for use on communication network 1124. In the present example, the inspection parameter may comprise a numerical indication of the detected amount of overlap between fastening components, and is correlated to a particular product produced. Correlation to a particular product can be achieved a number of ways, including assigning a product index number to each product produced. Information exchange 1110 thereafter obtains the inspection parameter and determines a quality parameter based thereon which is thereafter stored in quality system 1112. For example, information exchange 1110 can be programmed to monitor a memory location having the product index numbers stored therein. Each time the product index number increments, information exchange 1110 obtains the latest inspection data from the network. It should be appreciated that information exchange 1110 can also be configured to update its information based on a sampling plan (e.g., every fifth increment in the product index number). It should further be appreciated that it is also possible to store the inspection parameter as a quality parameter directly in quality system 1112.

One advantage of the present system is that it allows for real time quality monitoring and data storage without the need of a quality technician. Further, the present system is suitable for use with discontinuous items (e.g., hook and loop fastener components added to form a fastening system 80 as part of a training pant). This is unlike prior art inspection systems that attempt to capture quality data in real time in connection with continuous webs of materials.

In one embodiment, information exchange 1110 repeatedly accumulates inspection parameters associated with a plurality of training pants produced during a particular production run (e.g., the fifty most recent pants produced). Thereafter, information exchange 1110 computes an average and standard deviation of the accumulated plurality of parameters and compares the average and/or standard deviation to a target reflecting desirable quality characteristics. For example, if the inspection parameter is a numerical value indicative of a measured amount of hook-to-loop overlap for a refastenable training pant, the target can be an ideal value for an average or standard deviation, a limit, a range of values defining upper and lower tolerances, and so on. Product quality can be graded by comparing the average and/or standard deviation (e.g., a percent defective based on the average and standard deviation) to the target. As a result of this comparison, information exchange 1110 determines the quality parameter and makes it available for storage in the quality system. This is preferably repeated for each successive plurality of produced product.

In one preferred embodiment, average and standard deviation data is used to calculate a percent defective value.

The percent defective value is thereafter compared to a target (e.g., an allowable percent defective) to determine if the calculated percent defective value is close to or beyond the percent defective limit. More particularly, raw data is collected until a sample set of data has been obtained. Preferably the number of data points comprising a full sample set is configurable (e.g., 25 to 600 products inspected). An array of averages and an array of standard deviations are calculated. An array of target values and one or more arrays of limit conditions are previously stored in the system. An algorithm (e.g., written in C++) calculates a theoretical percent defective (i.e., how many products are theoretically outside the given limits, assuming a perfect normal distribution with the given average and standard deviation), and passes the percent defective information array back to an RSLogix™ program (discussed above) to perform additional functions (e.g., alarming decisionmaking) based on the percent defective array.

Alternatively (or additionally), the average and standard deviation can be compared to a target and limits as in control chart methods/practice.

In a similar embodiment, information exchange 1110 provides the average and/or standard deviation information (or another mathematical characteristic of relevance) to another manufacturing system which can store the information and/or compare the information to a target. For example, in one embodiment, information exchange 1110 sends the average and standard deviation information to operator interface 1118 (FIG. 4A). Software associated with operator interface 1118 compares the average and/or standard deviation information to a target, and thereafter presents the information to an operator.

In some contexts, it will be advantageous to know the quality associated with each product or package of products actually made available for sale—as opposed to the quality of all products produced, which would include culled products. Therefore, it is seen to be advantageous to provide an indication of whether a particular inspection parameter is associated with a culled product, as well to maintain a relationship between non-culled products and the packages into which they are to be (or have been) packaged for shipping. Thus, inspection data (and data derived therefrom) may be identified by population sets. One possible population set includes all data associated with a production run. A different population set may include all data associated with a sample set of products produced during the production run. Another population set includes only data associated with culled products. Still another population set includes only data associated with non-culled products (e.g., those being packaged for sale). Other population sets are possible.

Preferably, camera inspection system 1104 and/or one of the other inspection systems 1108 are configured to provide a signal/indication of which inspected products have been automatically culled by the inspection system. Automatic culling during manufacturing is known in the art and will not be further described herein. If information exchange 1110 receives a culled indication, it can eliminate the inspection data associated with the culled product when determining the quality parameter so that only data associated with non-culled products is stored in quality system 1112. This permits the manufacturer to determine with a great deal of precision the quality of the products it makes available for use in the market place. For example, if a group of products is consistently at the margin of acceptable quality, that product might be packaged for discount sale. Similarly, such a system provides the manufacturer with a high degree of confidence that substantially all products reaching consumers will exhibit positive quality characteristics. This provides a substantial advantage over prior art systems that rely on manual quality determinations of a limited number of the non-culled products produced.

At this point, it is instructive to note that information can be accumulated for all products inspected (e.g., both culled and non-culled), or a subset of all products inspected (e.g., only non-culled products). Further, information can be accumulated for all products inspected and, thereafter, subsets of the accumulated data may be used for a particular purpose. In this way, information may be accumulated for a variety of purposes. For example, quality data can focus on non-culled products, while waste assessments can focus on culled products. Similarly, process-health related analyses can focus on information from both culled and non-culled products.

In one embodiment, information exchange 1110 and/or quality system 1112 make available quality reporting data. Such quality reporting data can include real time data associated with each product produced (or a sample set of such data or mathematical characteristics of such data). For example, the quality data can be provided for display on operator interface 1118. A machine operator can view this data in real or near real time and monitor trends. For instance, quality data can be displayed against one or more targets. One example of a display which may optionally be used is a box-whisker plot of the data. This type of display graphically shows the user the average, upper and lower quartiles, and extremes of the data. It is a good graphical method to show average and variability information in one display. Other displays are also contemplated.

If the data is trending away from a desired target (or toward a limit), the operator can make a determination of how to alter the process before the quality data becomes unacceptable. Further, quality reporting from information exchange 1110 and/or quality system 1112 can correlate stored quality data to package codes (e.g., individual bags or cases of products). For example, when product is packed, the package code can be sent to information exchange 1110 and/or quality system 1112. Similarly, if repacking of any product occurs, codes can likewise be provided and stored.

One particular advantage of the present quality inspection system is that it does not require any destructive testing in order to acquire the quality data. For example, it is known to use "disappearing graphics" on training pants. The graphics are designed to disappear as exudates are discharged from the wearer. A prior art destructive test is sometimes referred to as a pulsed adhesive test for determining whether there is any glue on the poly cover relative to the graphics. The inspection systems and methods described herein allow for the use of a vision system to detect the presence of adhesive (glue) relative to the disappearing graphics, without the need for destructive testing. More specifically, an ultraviolet light may be used to fluoresce an optical brightener contained in the adhesive, thereby making the adhesive visible to the machine vision camera. It is also contemplated that the glue could be detected by other means such as SICK detectors or other inspection systems. Advantageously, when using the machine vision system, the camera can also see/detect material edges such that a determination can be made as to whether the glue is in a correct location. As one alternative, non-ultraviolet lighting can also be used, with the lighting positioned such that the adhesive casts shadows which are visible to the camera. In the context of a product comprising training pants, this would preferably be done prior to pant construction (e.g., immediately after applying glue to the outer cover web, but before the web is applied to the final product).

Further, such approaches do not require any products to be removed from the line and manually inspected. Of course, manual inspection and selective destructive testing can be used in connection with the present system and the results of such tests can be provided directly to quality system 1112 and/or information exchange 1110.

Another advantage of the quality inspection system disclosed herein is the ability to correlate data from a variety of sources. For example, information exchange 1110 can retrieve waste and/or delay data stored in waste/delay database 1120 and relate such data to inspection and quality data obtained from inspection system 1104 or manually entered into quality system 1112. Such waste and delay information can include, for example, the number of products produced and/or culled during a particular production run or work shift. By correlating this information in time with the inspection system, information exchange 1110 enables an operator or logic system to spot trends between quality data and waste/delay information, machine crew information, and so on.

Similarly, in one embodiment information exchange 1110 retrieves machine/process set point information from machine set point database 1114 and/or registration system and correlates such data to inspection/quality data. By correlating this information in time, it is possible to identify machine/process setting contributions to product quality. This information is also useful for improving future production runs and/or to automatically make adjustments to current production runs. Likewise, information exchange 1110 can correlate raw material data from raw material database 1122 to product quality for determining raw material contributions (positive and negative) to quality and/or productivity.

It is instructive to note at this point that data manipulation can be accomplished within a processor associated with information exchange 1110, or in another system. For example, data manipulation can be accomplished in one or more vision inspection system computers (e.g., computers associated with inspection system 1104), a quality system (e.g., quality system 1112), a registration control system (e.g., system 1116), and so on. This aspect of the present disclosure is reflected, at least in part, by the dotted lines indicating information flow into and out of information exchange 1110, as well as the use of communication network 1124 for information flow. Further; although no particular data manipulation task need be accomplished in information exchange 1110, the use of information exchange 1110 facilitates an exchange of data/information, thereby allowing such data/information to be related together in the various advantageous ways such as those described herein.

Figure 4B:
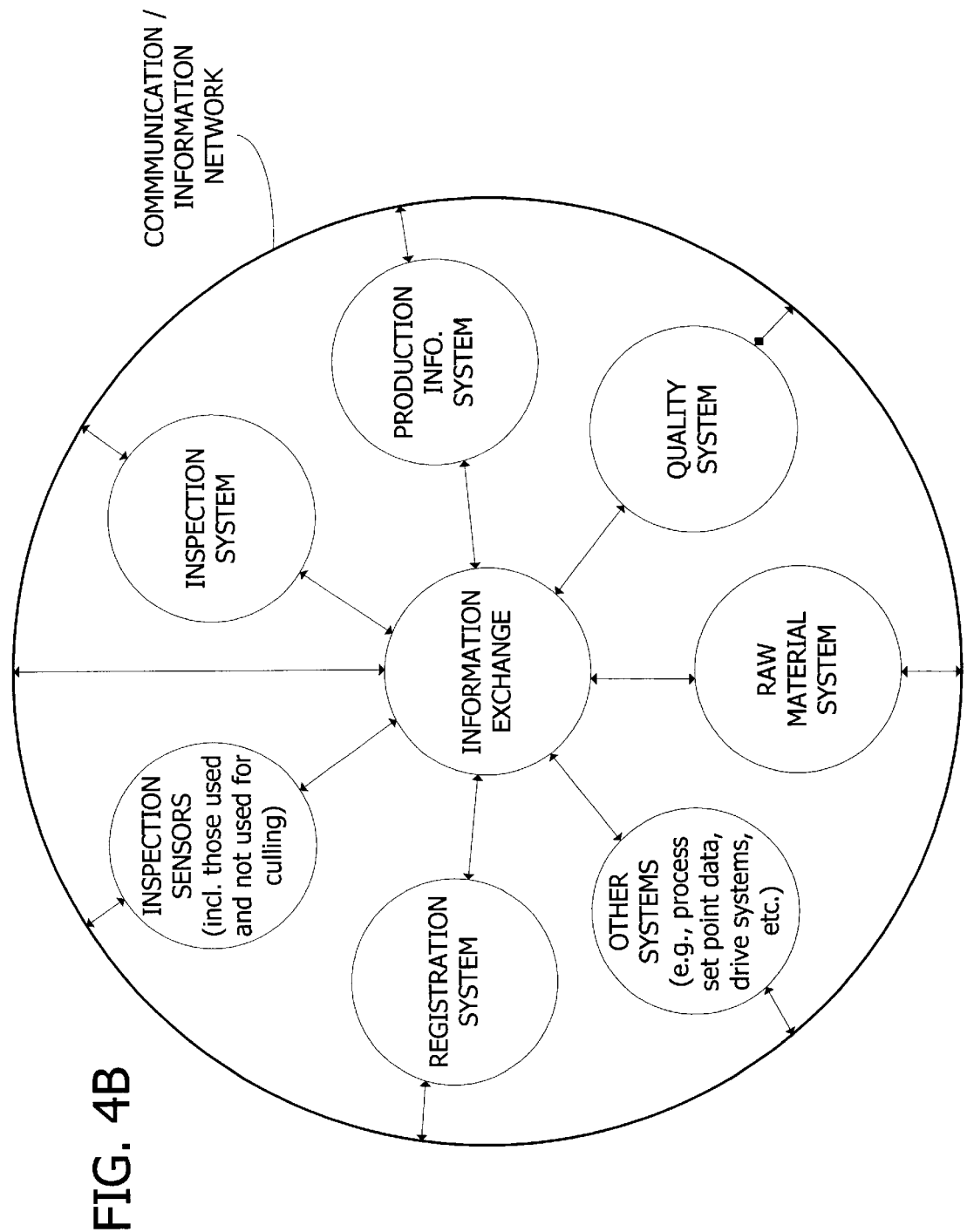
FIG. 4B illustrates schematically one embodiment of a flow of information to and from an information exchange.

FIG. 4B schematically illustrates information flow to and from an information exchange, such as information exchange 1110 of FIG. 4A. As illustrated, information may flow both to and from the information exchange using an information network.

FIGS. 5A and 5B are logic flow diagrams illustrating a method (identified generally as reference character 1150) of providing real time quality information, suitable for use in connection with an inspection system such as that illustrated in FIG. 4A. At block 1152, an inspection system automatically inspects one or more aspects of the product being produced (e.g., a machine vision inspection system detects a measurement of the hook-to-loop overlap of a training pant). As indicated above, inspection system 1104 (FIG. 4A) can detect an absolute placement of one or more components, or a relative placement of one component relative to another component, or a combination of absolute and relative placements. At block 1154, a quality parameter is determined in association with the inspected aspect of the product produced. In one form, the quality parameter is a numerical value corresponding to the inspected aspect (e.g., a numerical value of the hook-to-loop overlap detected by a machine vision system). The quality parameter is thereafter correlated to specific products inspected (block 1156). Preferably, this correlation is done at least on the basis of a product index and/or time, but may be done on other bases. For example, if a unique serial number or lot number is assigned to a particular product, the quality parameter can be correlated in that way as well. At block 1158 a determination is made as to whether the quality parameter is associated with a culled product. As reflected by blocks 1160 and 1162, it is generally believed to be preferable (and not mandatory)—for quality purposes—to store quality data only with respect to non-culled products.

In one embodiment, a culled/non-culled signal is correlated to the particular product inspected using a shift register approach. More specifically, the inspection system sets an offset for each inspection point on the machine. For example, assume that one inspection point (e.g., a photoeye positioned to detect a flap position) detects a misalignment with respect to a particular product that should lead to culling that product. The inspection system knows the position of that product relative to the next available culling point because it knows the location of the inspection point. As such, the system can use an offset and shift register to track the product being culled.

Further, it should be understood that the stored quality data can relate to individual inspected products, or to a mathematical characteristic of a plurality of all products or culled products or non-culled products. For example, the stored quality data can reflect an average and/or standard deviation of each 50 non-culled products produced during the production run. Advantageously, average and standard deviation data is useful for identifying a percent "defective" characteristic relative to a target(s) (e.g., an acceptability range). It should be understood that other sample sets may be used. For example, a suitable sample set can be selected and inspected such that a statistical representation of a quality characteristic of substantially all products produced during the production run may be determined from the inspected sample set.

Connector A (block 1168) is a connection to a flow diagram (FIG. 5B) that illustrates exemplary steps for determining a quality parameter as a function of a plurality of inspection measurements. At blocks 1170 and 1172, the inspection system obtains an image of one or more component parts and publishes a numerical value corresponding to a detected placement of the one or more component parts. At block 1174, a plurality of the published numerical values of the detected placements are accumulated so that a mathematical characteristic (e.g., average and standard deviation, as shown in block 1176) can be used to determine the quality parameter to be stored (block 1178).

Referring again to FIG. 5A, at blocks 1164 and 1166, the stored quality data is used to prepare a quality report for publication and use. In one form, the quality report is a computed, exponentially weighted moving average of the quality data stored in the quality database. It should be understood, however, that a large variety of quality reports and report formats can be achieved with the novel systems and methods disclosed herein.

Connector B (block 1180) is a connection to a flow diagram (FIG. 5B) that illustrates exemplary uses of the quality report prepared and published at blocks 1164, 1166 of FIG. 5A. One such use is to display—preferably in real time—the quality report to an operator associated with the manufacturing process. Another exemplary use is to display the quality parameter relative to a standard/target. For instance, the quality parameter can be displayed relative to upper and lower quality limits, or a number of "quality bins" (e.g., best quality, nominal/acceptable quality, degraded quality, and unacceptable quality). Yet another exemplary use of the quality report is to correlate the determined quality parameters to a package of products produced during the production run.

Connector C (block 1184) is a connection to a flow diagram (FIG. 5B) that illustrates additional ways to use quality data developed during method 1150. Although connector C is illustrated as occurring between blocks 1162 and 1164, such other uses are not limited to being performed at that particular point in the method. As illustrated in block 1186 of FIG. 5B, quality data can be related to raw material data so that relationships between raw material and quality can be mined. Likewise, quality data can also be related to productivity data (e.g., waste and delay data) to determine relationships between quality and waste/delay. Similarly, quality data can be related to machine set point information so that relationship between quality measurements and process/machine settings can be identified and used to improve quality.

Quality data can be related to raw material data so that relationships between raw material and quality can be mined. For example, data from an inspection system positioned to detect side panel skew in a training pant manufacturing process can be correlated to particular material lots (i.e., using a raw material database) to determine if material properties affect the converting process and product quality in any significant way.

Quality data can also be related to productivity data to determine relationships between quality and waste/delay. For example, juxtaposing cross direction material overlap variability determinations with machine waste data provide an indication of the relative importance of reducing fastening overlap variability (i.e., for a prefastened training pant) to the productivity of the manufacturing process. Assume, as a further example, that it is desirable to reduce average fastening overlap variability by 0.5 mm, data from a prior production run is analyzed to determine whether there was any marked improved in waste during times at which the measured overlap variability fell within the desired range. If there was no marked improvement, the cost of achieving the improvement in variability might not be justified.

Relationships between quality measurements and process/machine settings can also be identified and used to improve quality. Referring to the manufacture of prefastened training pants as an example, in trying to reduce fastening overlap variability (e.g., in a machine direction), an operator could vary/change settings of relevant vacuum levels on the machine. An automated quality data system can detect such changes substantially immediately, so that the modification to the machine can be evaluated in the short term by comparing, for example, average and standard deviation information to those achieved before the change. Unlike the prior art, this approach permits much faster process optimization and further permits quality determinations associated with or correlated to one or more composite products produced during the production run.

Another example of an advantage, in the context of improving fastener overlap with prefastened training pants, is the position of a device used in the fastening operation (e.g., a folding board or a folding finger) can be monitored with an electric tape or with an LVDT (linear voltage differential transducer) to identify and determine the impact of finger placement on fastener overlap quality.

As still another example, side panel base material (sometimes referred to as "SBL") stretch to stop information (e.g., test data available from a raw material database and supplied by the raw material supplier) can be used to automatically adjust a side panel cut length (and/or finished product panel width).

Although a wide variety of advantages are possible, it should also be understood that less data can be monitored, stored and used, if desirable. For example, in some applications, computer storage limitations may present concerns. In those and similar situations, periodic sampling of measurements can be employed to reduce the amount of data handling required.

As can be appreciated from the foregoing, the systems and methods for automating quality processes disclosed herein provide distinct advantages over prior art systems that require a quality technician to manually measure and enter quality measurements into a quality database. A specific example is instructive. With prior art manual inspection systems (i.e., those in which quality data is not tied to product packages), if the inspector finds a defect, the inspector must typically "back track", starting with packaging at the end of the machine until he/she finds the end of defect occurrences. This can be significant because an inspector can only inspect a limited number of items—perhaps one item every 30 minutes or so. By tracking data in real time and relating that data to a package code (e.g., bag or case), operators and/or quality inspectors are notified as to the existence of defects faster (i.e., those not significant enough to cause an automatic cull, but beyond acceptable limits) and to pinpoint those defects to a particular package or group of packages. Further, with the present quality inspection systems and methods, quality reports can be generated that include quality data for substantially every product shipped, rather than just a few products that are manually inspected during each production run. Also, the present quality systems and methods permit operators to relate inspection data to other manufacturing-related data that may be available which is useful for root cause failure analysis, process improvement, and problem elimination. Such other manufacturing-related data includes raw material data, machine settings data (including changes to such settings during a production run), and/or waste/delay data.

Figure 6:
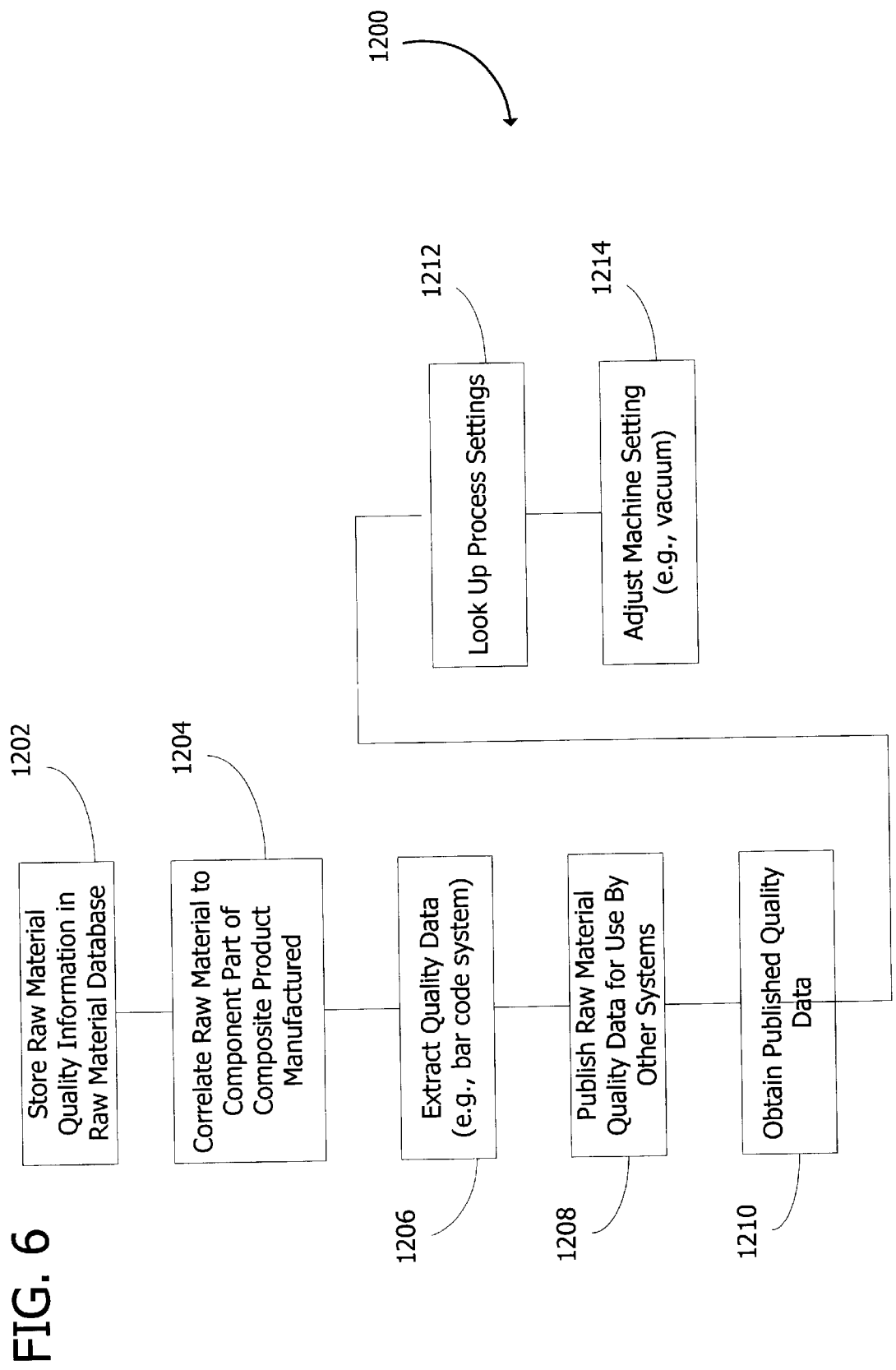
FIG. 6 is a logic flow diagram of one method of using quality information from a raw material database to adjust process settings, suitable for use in connection with an information system such as that illustrated in FIG. 4A.

FIG. 6 is a logic flow diagram of a method of using quality information from a raw material database to adjust process settings, suitable for use in connection with the information system 1100 of FIG. 4A. At block 1202, quality information associated with raw material is stored in a raw material database. Preferably, the raw material supplier provides this information. For example, as described above in connection with FIGS. 1–3, in one embodiment of a child's training pant 20, side panels 34, 134 desirably (although not necessarily) comprise an elastic material capable of stretching in a direction generally parallel to the transverse axis 49 of the training pants 20. A certain amount of stretching, therefore, is desirable. Advantageously, the quality inspection systems and methods disclosed herein allow for the elimination of redundant testing of side panel stretch testing, such as a stretch to stop test. For example, the supplier of the elastic material used to supply side panels 34, 134 typically provides data corresponding to a stretch to stop test conducted on the supplied elastic material. That data can be entered directly into a quality system associated with the product being manufactured from the raw material (e.g., quality system 1112 of FIG. 4A in connection with manufacturing training pants). With this data in the system, there is no longer a need to conduct a stretch to stop on a finished product because the information is already known.

Referring still to FIG. 6, at block 1204 and 1206 the raw material quality data is correlated to products being produced on the production line. For example, it is known in the art to track when a particular spindle of material is switched into (or out of) a production line process. Further, the pertinent raw material quality data can be stored in a code (e.g., a bar code) associated with the material itself. Thus, an operator can use a code reader to extract the data and have that data published (e.g., via raw material system 1122 or information exchange 1110 of FIG. 4A) for use by other manufacturing information systems. For example, at blocks 1210–1214, the information exchange 1110 can obtain the raw material quality information, as well as process settings (e.g., from machine set point data base 1114 or registration system 1116) and, based on the raw material quality information, adjust a machine setting.

Registration Set Point Control System

Referring again to FIG. 4A, information system 1100 can also be configured to provide a real time automatic registration set point control system. Such a system is particularly useful in connection with manufacturing disposable absorbent garments made from a sequential addition of component parts requiring registration during a production run. Such a system is particularly useful for controlling registration of one or more components of a training pant.

An inspection system (e.g., camera inspection system 1104 or one of the other inspection systems 1108) is employed to inspect a component part of composite products produced during the production run. Advantageously, the inspected aspects of the component parts can be the same aspects inspected as part of the quality system described above. Preferably, the inspection system is configured to inspect each product produced or a statistical sampling of products. The inspection system thereafter publishes an inspection parameter that provides an indication of a characteristic of the inspected component part. Information exchange 1110 thereafter obtains the inspection parameter (e.g., via communication network 1124) and determines a set point adjustment as a function of the inspection parameter. The set point adjustment is used to adjust a set point of registration system 1116.

Various aspects of controlling registration in connection with manufacturing training pants (e.g., prefastened training pants) help illustrate additional aspects of registration set point control system constructed and operated in accordance with aspects of the present disclosure. For example, and as described above with in connection with FIGS.1–3, it is considered desirable to control longitudinal placement of side panel 34, 134 component parts of training pants 20. Thus, there is a need to control the longitudinal placement of side panels 34, 134. One or more photoeye sensors (i.e., part of the other inspection systems 1108 illustrated in FIG. 4A) detect and control the longitudinal placement of each side panel. An exemplary photoeye type is the MAXI-BEAM® series, available from Banner Engineering Corporation, Minneapolis, Minn., U.S.A. More particularly, one or more photoeyes detect the leading edge of the side panel in the longitudinal direction. One or more cameras of camera inspection system 1104 are positioned "downstream" from the photoeye sensor(s) to double check the longitudinal placement of the side panels. For example, a machine vision system captures an image of the entire product at a point after the side panel placement takes place. The machine vision system is preferably programmed to detect gray scale differences in the captured image(s) to determine an absolute position of the side panel placement on each product produced during a production run. The determined longitudinal position of the side panel is compared to a target (e.g., in information exchange 1110 or in another subsystem such as registration system 1116). Based on an amount of difference between the determined absolute position of the side panel placement and the target, the photoeye set point is adjusted to maintain the longitudinal placement within desirable bounds. It should be understood that variations are possible. For instance, in one embodiment, rather than comparing each determined position of the side panel placement to a target, information exchange 1110 (or another subsystem such as registration system 1116) accumulates a plurality of measurements. The set point determination is then made on the basis of a characteristic of the accumulated plurality of measurements (e.g., on the basis of an average and/or standard deviation determined from the accumulated plurality of measurements).

Another example involves predictive adjustments and, in particular, adjustments based on the determined absolute position of the side panel placement and the target. When the vision system is capturing images before a downstream process, predictive adjustments can be made. As a specific example, if the side panels on one side of the product begin to get short, all other parameters being substantially equal, the fastener overlap on the one side would also decrease. Since this side panel width prior to the fastening module, the system can be programmed to steer the web towards the one side with the shorter side panels. This would be a predictive or an anticipatory adjustment which would minimize the overall loss in overlap on the one side.

Another example involves detecting fastener components of fastening system 80 of the above-described training pants 20. As discussed above, it is desirable to control placement of a hook fastener component (e.g., first fastening component 82 above of FIGS. 1–3 above) in the machine direction (MD) relative to an associated side panel. In one embodiment, hook fastener placement is controlled by relative positioning of a signal from a proximity switch (e.g., an applicator proximity switch on a line shaft) located on a cut/place module, in connection with signals from a pair of photoeye sensors (e.g., other inspection systems 1108) positioned to detect the side panels. A full product inspection machine vision system (e.g., one or more machine vision systems associated with camera inspection system 1104) positioned downstream of the photoeye sensors can measure the absolute placement of the hook component on the training pant, in a manner similar to that described above with respect to measuring side panel longitudinal placement. With this information, information exchange 1110 (or another subsystem such as registration system 1116) can determine a desired relative offset between a signal from the applicator proximity switch and the associated photoeye sensor and thereafter adjust the set point of the offset to maintain the desired placement of the hook fastener.

Still another example involves manufacturing training pants 20 (FIG. 1). As described above, it is often desirable to locate one or more graphic components on such training pants during manufacture. Certain graphics, such as a graphic waist band, are registered for placement relative to placement of a pad component. Thus, graphics registration may be controlled by a pad detection signal coupled with a graphics eyespot detector (e.g., detected by a UV photoeye), by known methods. A full product inspection system (e.g., such as a multiple camera system 1104) determines an absolute measurement of the graphic placement relative to the pad. Based on this absolute measurement, information exchange 1110 (or another subsystem such as registration system 1116) thereafter determines whether a set point adjustment is required based on the relative offset between the pad detection signal and the detected graphics eyespot. Thus, the full product inspection system provides an input for controlling the registration of the graphics.

Also, and as described above, other examples include detecting the placement of adhesives (e.g., determining where glue is positioned relative to graphics, such as disappearing graphics, or the position of glue used to hold elastic components to a final product).

Figure 7:
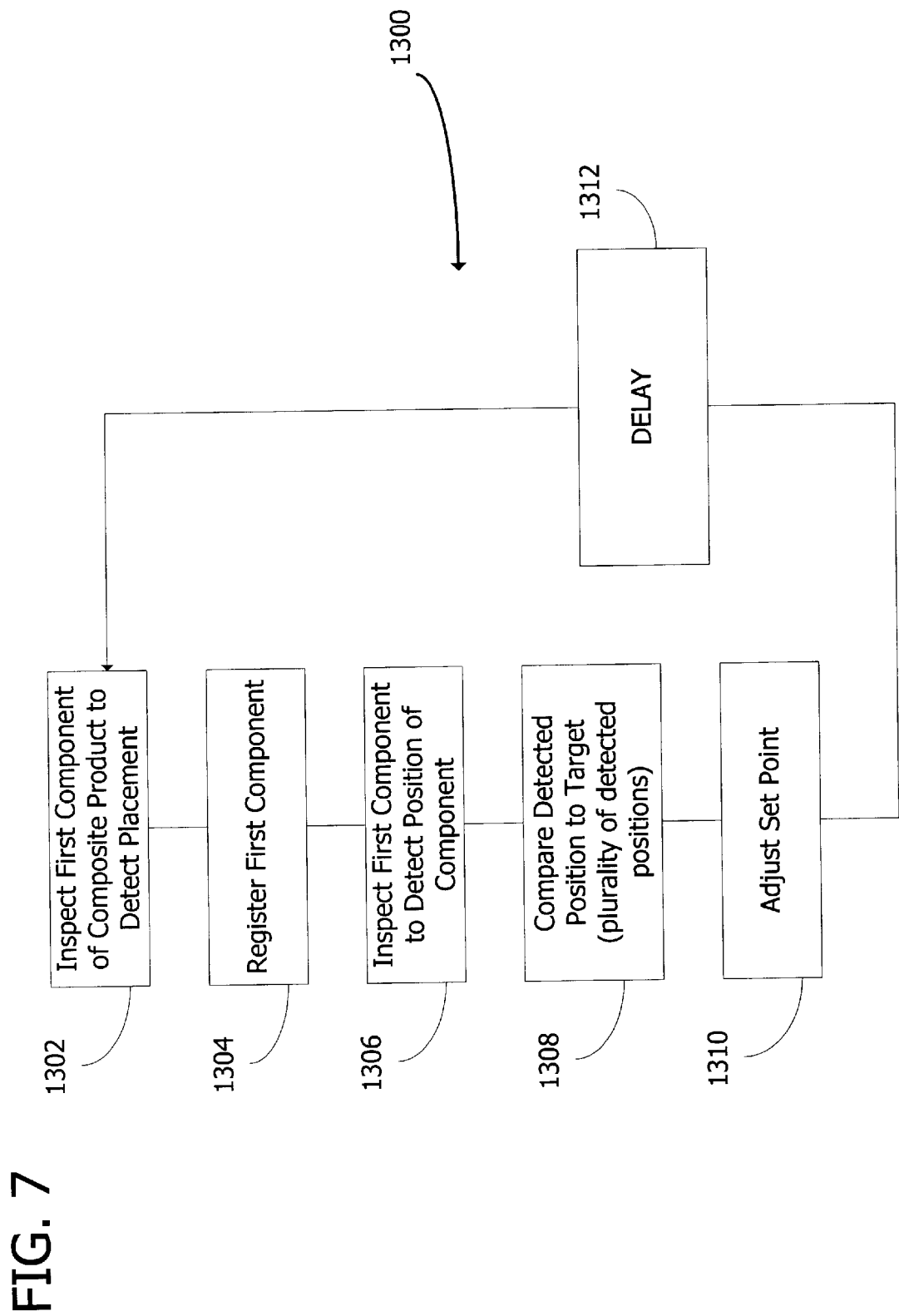
FIG. 7 is a logic flow diagram illustrating one method of providing real time registration set point control, suitable for use in connection with an information system such as that illustrated in FIG. 4A.
Figure 8:
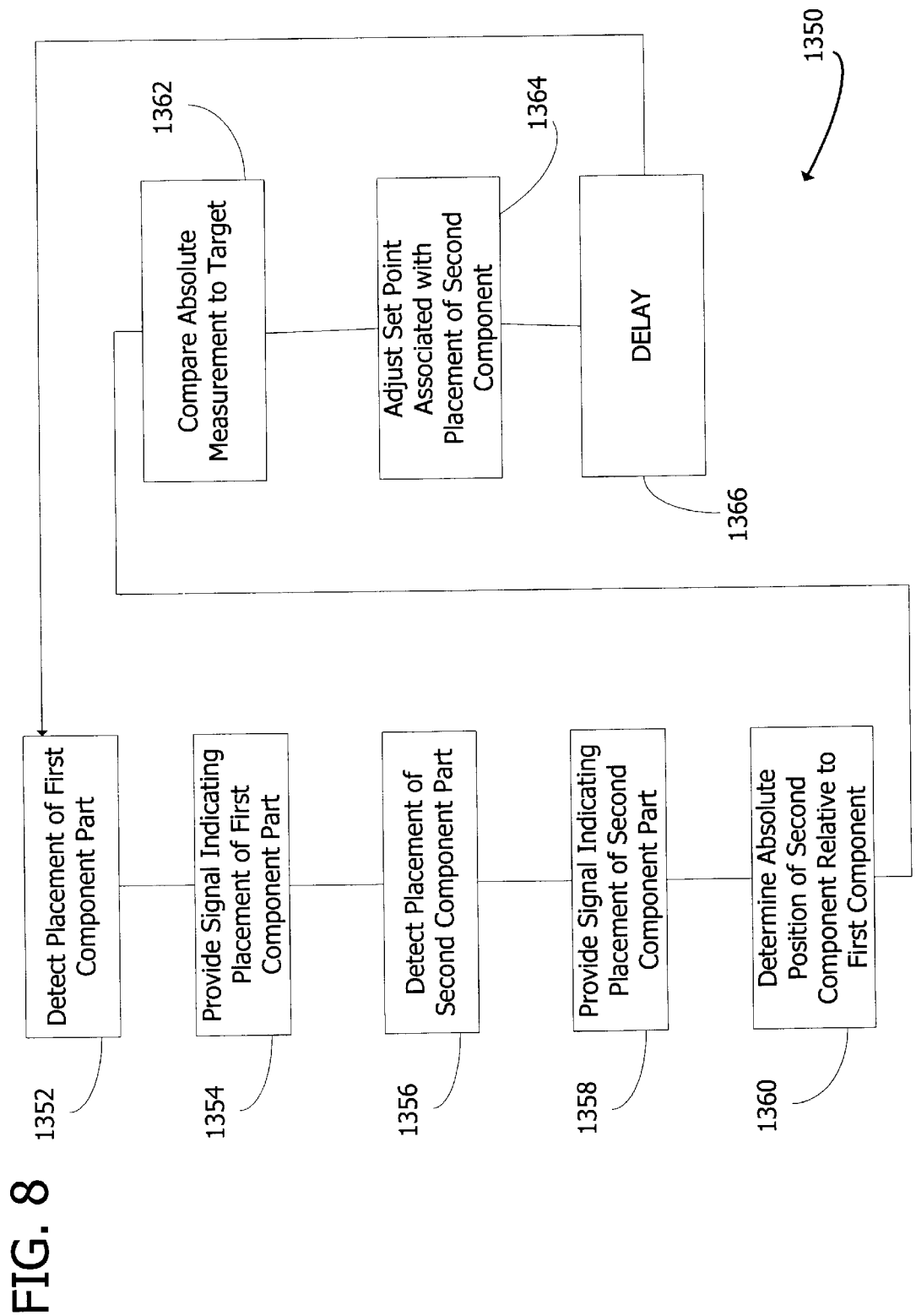
FIG. 8 is a logic flow diagram illustrating another method of providing real time registration set point control, suitable for use in connection with an information system such as that illustrated in FIG. 4A.

FIGS. 7 and 8 are logic flow diagrams illustrating methods of providing real time registration set point control, suitable for use in connection with an information system such as information system 1100 illustrated in FIG. 4A.

Referring first to FIG. 7, illustrated therein is a method 1300 for using an inspection system to control registration of component parts of composite products, such as components of disposable absorbent garments, including training pants 20. At blocks 1302 and 1304, first inspection system detects and controls a placement of a first component of a composite product. For example, as discussed above, a photosensor such as a photoeye is positioned to detect and trigger a side panel cut length, which may be regarded as a form of registration control (controlling the side panel length relative to the entire training pant). At block 1306, a second inspection sensor (e.g., a full product machine vision system such as camera inspection system 1104 of FIG. 4A positioned downstream from the first inspection sensor) detects an absolute position of the first component. The second inspection sensor provides a numerical value of the absolute position of the first component which, as illustrated at block 1308, is compared to a target for determining (block 1310) whether a set point change is desirable. In one embodiment, a delay or deadband (block 1312) may be implemented (e.g., immediately after changing a set point). This delay may also be viewed as a filtering process, initiated in response to a machine transition, to avoid the collection of transitional data that may occur while during such a machine transition.

Apart from set point changes, other machine transitions that can initiate similar data filtering (e.g., deadband filtering) include splice occurrences. For example, a machine indication that a raw material splice is pending may be used to disregard collection of inspection data during a particular time period (e.g., a period immediately following the machine transition or indication of the pending machine transition). As can be appreciated in view of the foregoing, such filtering on transitions is applicable to a variety of the data collection methods and systems disclosed herein. For example, deadband filtering may be used to limit data collection for use in providing operator alarms and/or machine troubleshooting indications.

Using side panel longitudinal placement as an example, a photoeye (e.g., one of the other inspection systems 1108 of FIG. 4A) is positioned to detect and control the longitudinal placement of side panel components of training pants manufactured during a production run. The photoeye operates at a controllable set point and provides a signal indicative of a position of the leading edge of the side panel. A full product machine vision inspection system thereafter determines an absolute position of the side panel longitudinal placement. A plurality of these absolute measurements are accumulated (e.g., by information exchange 1110) and one or more mathematical characteristics, such as the average and/or standard deviation of the plurality of measurements are thereafter determined. The mathematical characteristics are thereafter compared to a target to determine if an adjustment to the set point of the photoeye is required in order to maintain a desired degree of registration of the side panel longitudinal placement.

It should be understood that the foregoing example can be scaled to include detecting positions of two or more components and controlling registration by controlling the position of one component relative to another component, using a machine vision system. This is an area in which a machine vision inspection system provides certain advantages. For example, it is possible that a relative registration between first and second component parts remains relatively steady (within acceptable bounds, and as measured by reference to a position of the sensor), but the absolute registration of the two components on the full product is out-of-bounds. Hook longitudinal placement relative to a leading edge of a side panel of a prefastened training pant provides an illustrative example. The hook may be placed by comparing a hook applicator proximity switch signal to a side panel longitudinal placement photoeye signal. With a full product vision inspection system, it is possible to obtain an absolute measurement of the leading edge of hook to the leading edge of the SBL, and thereafter adjust the proximity switch/photoeye system offset accordingly to obtain and/or maintain a desired spacing.

FIG. 8 is a logic flow diagram illustrating another method of providing real time registration set point control, suitable for use in connection with an information system such as information system 1100 illustrated in FIG. 4A. At blocks 1352 and 1354, a placement of a first component part is detected. A signal is provided that indicates the placement of the first component. For example, a photosensor can be used to detect a placement of a pad component of a training pant product during manufacture. At blocks 1356 and 1358, a placement of a second component part is detected and a signal is provided to indicate the placement of the second component (e.g., a UV photoeye detects a graphics eyespot on the training pant during manufacture). At block 1360, an absolute position of the second component relative to the first is determined. For example, a full product inspection system can detect a position of the graphics on the training pant and the position of the pad. At blocks 1362 and 1364, this absolute measurement is compared to a target so that a set point adjustment can be made with respect to placement of one or both components (e.g., adjusting a set point so that the graphics are positioned at a correct position relative to the pad). In one embodiment, a delay or deadband (block 1366) is implemented immediately after changing a set point. This helps to avoid the collection of transitional data that occurs while the process shifts from one set point to another. As already explained herein, it may be preferable to accumulate a plurality of absolute measurements associated with a plurality of composite products (e.g., 50) and compare an average and/or standard deviation of the plurality of measurements to a target. It should be understood that such an approach will help reduce the possibility of spurious erroneous results being used to adjust registration set points.

It should be appreciated that the desired set point adjustment can be determined by, for example, the information exchange, the inspection system, or the registration control system.

Web Guiding

Figure 9:
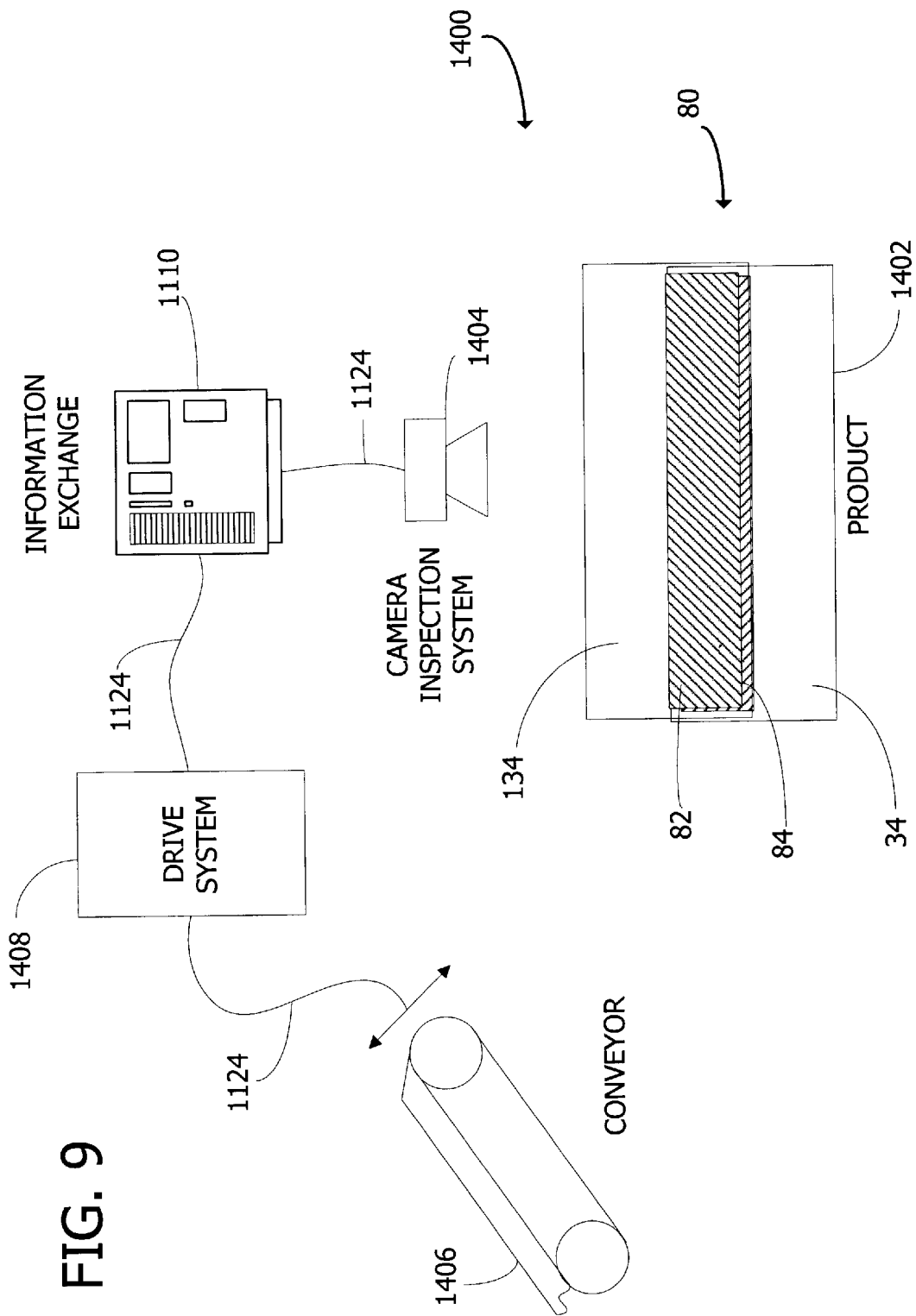
FIG. 9 is a schematic illustration of one embodiment of a web guiding system, suitable for use in connection with an information system such as that illustrated in FIG. 4A.

FIG. 9 illustrates one embodiment of a web guiding system (indicated generally as 1400 in FIG. 9), suitable for use in connection with an information system such as that illustrated in FIG. 4A. For ease of understanding, FIG. 9 will be described in terms of a web guiding system for use in controlling an amount of overlap between fastening components 82, 84 of fastening system 80, associated with side panel components 34, 134 of a pre-assembled training pant 20.

A product 1402, including fastening system 80 is inspected by a camera inspection system 1404. The camera inspection system 1404 can be part of multiple camera inspection system 1104 (FIG. 4A), or can be a separate system. In one embodiment, camera inspection system 1404 comprises a machine vision inspection system (e.g., a Cognex series 8210 processor, running Checkpoint® III software). In the illustrated exemplary embodiment, camera inspection system 1404 is positioned to detect an amount of overlap between fastening components 82, 84 of fastening system 80 after an assembly. This may be described as inspecting a visual image of two web components to determine the placement of the components relative to one another. In one embodiment, camera inspection system 1404 captures images of the overlap between fastening components 82, 84 for every training pant produced during a production run, and from two aspects—a left side and a right side. The joinder of fastening components 82, 84 actually occurs downstream from a conveyor system 1406. By steering conveyor system 1406 (e.g., using drive system 1408), it is possible to steer the product prior to and into the fastening process (which, in this example, cannot be steered). As noted below, it is also contemplated that one embodiment would steer the fastening process to the product.

FIG. 9 also illustrates information exchange 1110 and a network (communication network 1124) for facilitating communications between camera inspection system 1404, information exchange 1110, drive system 1408, and conveyor 1406. It should be understood that other means for facilitating communications between these subsystems can be employed, including direct connections or multiple communication networks or combinations thereof.

In operation, camera inspection system 1404 automatically inspects each training pant produced during a production run (or a sample set of training pants produced during the run) to detect an amount of overlap between fastening components 82, 84. In one embodiment, camera inspection system 1404 captures images of fastening system 80 from two sides of the product (referred to as a "left side" or "right side", or a "drive side" and an "operator side"). FIGS. 10A–10D schematically illustrate fastening system 80 in this regard. In particular, FIG. 10A illustrates fastening components 82, 84 unfastened. FIG. 10B illustrates an overlap between fastening components 82, 84, viewed from a right side of the product. FIG. 10C illustrates the overlap between fastening components 82, 84, viewed from a left side of the product. FIG. 10D illustrates a completed product 20 for context.

In one embodiment, fastener overlap on the right side of the product is inspected by lighting the seam from the inside of the training pant and taking a picture/image with a camera located on the outside of the training pant. A substantially similar process occurs with the fastener overlap on the left side of the product (e.g., using a separate camera and light). In this embodiment, rather than using two inspection systems to inspect the images of the right and left side fastener overlaps separately, an image combiner places the two images on the same monitor screen (e.g., side by side). In this regard, the combined images may be viewed as a form of a composite image. Is it also possible to overlay the images.

Camera inspection system 1404 publishes an inspection parameter (e.g., a numerical value) indicative of the detected amount of overlap of fastening components 82, 84 (e.g., based on machine vision tools which are generally understood in the art). Thereafter, information exchange 1110 uses the inspection parameter data to determine whether the position of conveyor 1406 should be adjusted. For example, in one embodiment, information exchange 1110 accumulates a plurality of inspection parameters associated with a plurality of products produced (i.e., a plurality of composite webs formed by the joinder of fastening components 82, 84 of releasable fastening system 80). Information exchange 1110 determines a mathematical characteristic (e.g., an average and/or standard deviation) of the accumulated plurality of inspection parameters. The mathematical characteristic is compared to a target (e.g., an acceptability value/range of values) to determine whether drive system 1408 should adjust the position of conveyor 1406 to achieve a more desirable amount of overlap between fastening components 82, 84 on future products produced.

In one embodiment, information exchange 1110 provides the mathematical characteristic data for use by drive system 1408. Drive system 1408 thereafter compares the mathematical characteristic to target data to determine an amount (if any) to adjust conveyor 1406 (e.g., in a cross-direction) so that the desired amount of overlap between the two fastening components 82, 84 is achieved. In another embodiment, information exchange 1110 determines an amount that conveyor 1406 should be adjusted and provides an adjustment parameter to drive system 1408 for adjusting conveyor 1406.

Figure 11:
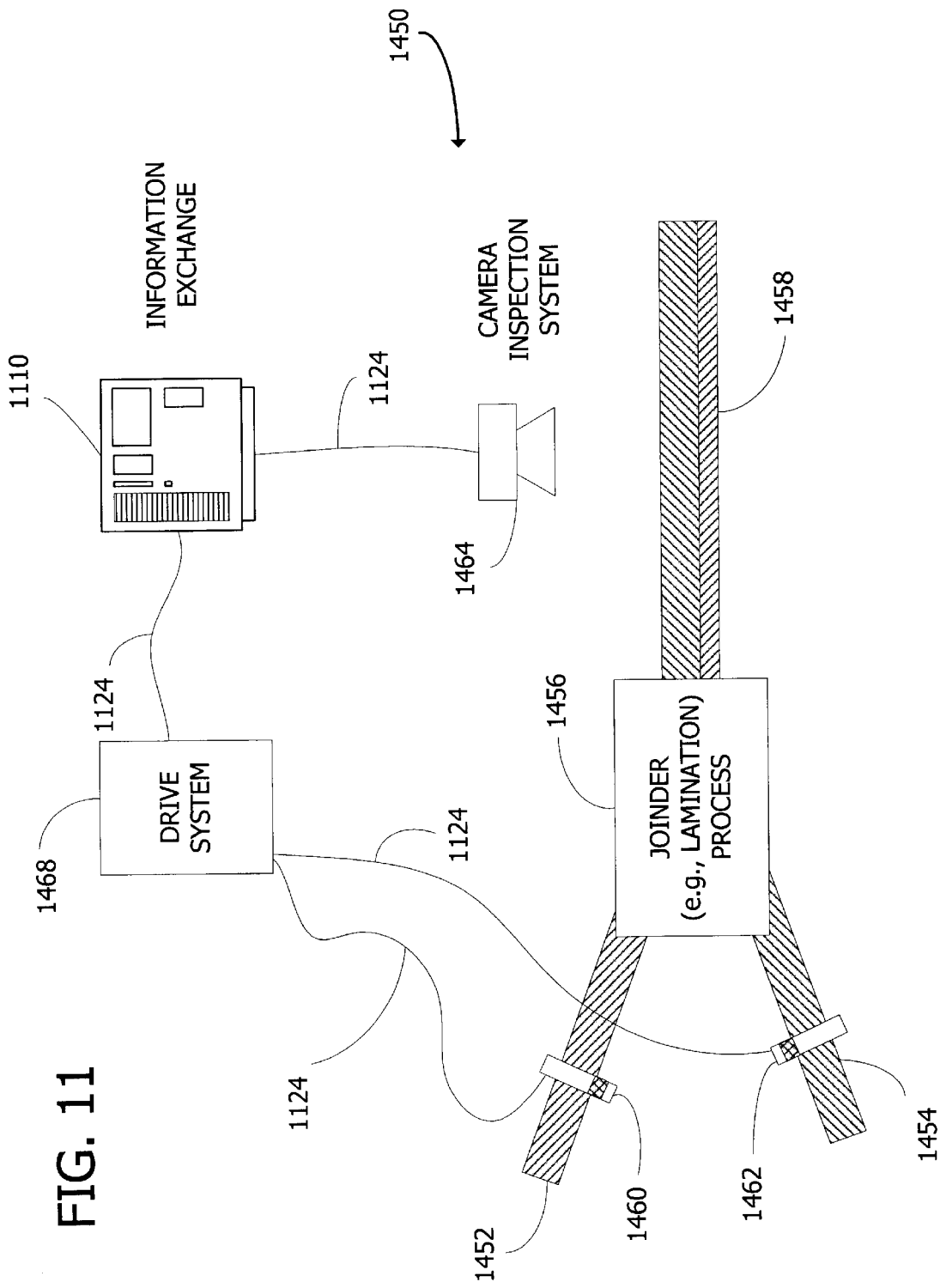
FIG. 11 is a schematic illustration of another embodiment of a web guiding system, suitable for use in connection with an information system such as that illustrated in FIG. 4A.

FIG. 11 illustrates another exemplary embodiment of a web guiding system (indicated generally as 1450 in FIG. 11), suitable for use in connection with an information system such as that illustrated in FIG. 4A. System 1450 is illustrated in the context of an aspect of a manufacturing process in which first and second web components 1452, 1454 are provided on separate feed systems (e.g., conveyors) and processed (e.g., a joinder process 1456 such as a lamination process or a cutting process) to form a composite product or product component 1458. In the illustrated example, a first web guide 1460 steers web component 1452 based on a sensor (i.e., a web guide sensor) associated with web guide 1460 that is designed to detect the edge(s) of web components. Similarly, a second web guide 1462 steers web component 1454 based on a sensor associated with web guide 1462 that is designed to detect the edge(s) of web components. Such sensors are generally referred to as edge detectors (e.g., ultrasonic or light bar detectors), and they are located in close proximity to the associated web guide and provide a web edge detection signal to the web guide. Fife Corporation of Oklahoma City, OKla., provides such sensors and web guide equipment, including part no. 85427–002.

An operational example further illustrates the advantages of web guiding system 1400. Disposable diapers and training pants often include a web of "surge material" that is designed to rapidly intake discharged exudates to prevent leaking outside of the garment. Such surge material is added as a continuous web of material during the manufacturing process. If a typical prior art web guide with an edge detector is used to guide the web of surge material into a cut and place process on the manufacturing line, there is no feedback of the placement of the surge material (e.g., in the cross direction) on the downstream web. A downstream vision system, such as camera inspection system 1404, provides feedback of the actual placement of the surge material after the cut and place operation so cross direction errors can be corrected. This can be done automatically by moving the guide, by physically moving the guide point (e.g., by way of a mechanically operated microslide or the like), or by moving the guide point electronically inside the sensor (e.g., by adjusting an electrical offset).

Preferably, one or both web guide sensors are mechanically and/or electronically adjustable. For example, a mechanically adjustable web guide sensor preferably includes a capability to have its position mechanically translatable. Likewise, an electronically adjustable web guide sensor preferable includes a capability to have its operating set point be adjusted (e.g., via a message/signal over communication network 1124).

After the joinder process 1456, a camera inspection system 1464 inspects the composite web 1458 to detect an alignment between components 1452, 1454 based on one or more captured images of composite web 1458. Preferably, the camera inspection system 1456 is part of multiple camera inspection system 1104 (FIG. 4A); but it can be a distinct system. In one embodiment, camera inspection system 1456 comprises a machine vision inspection system, such as a Cognex 8120 processor running Checkpoint® III software, available from Cognex Corporation. Camera inspection system 1464 communicates with a drive system 1468 for controlling one or both feed systems supplying the first and second web components 1452, 1454 to adjust a placement of guides 1460 and 1462 to achieve a best alignment of the individual webs in composite web 1458. In the illustrated example, web guides 1460, 1462, camera inspection system 1464, drive system 1468, and information exchange 1110 communicate on an information/communication network, such as communication network 1124. Other communication schemes are possible.

The web guiding system 1450 illustrated in FIG. 11 will be further described in terms of operational control examples. A first example is generally referred to as a direct control example. In the first example, web guide 1460 and its associated edge detector generally guide first web component 1452 as it is fed into joinder process 1456. Similarly, web guide 1462 and its associated edge detector generally guide second web component 1454 as it is fed into joinder process 1456 to form composite web 1458. In this example, camera inspection system 1456 comprises a machine vision system capable of detecting grayscale differences indicative of the placement of first and second web components 1452, 1454 to determine the alignment of such components after the joinder process. Camera inspection system 1456 is preferably configured and arranged to periodically inspect composite web 1458. For example, when manufacturing training pants 20, such as those described above in connection with FIGS. 1–3, camera inspection system 1456, composite web 1458 corresponds to a plurality of training pants, prior to a cutting stage. Thus, camera inspection system 1456 is configured to inspect each training pant 20 as it is being manufactured at a point after joinder process 1456.

Camera inspection system 1464 provides an inspection parameter that indicates the determined relative placement (e.g., alignment) of first and second web components 1452, 1454. Information exchange 1110 obtains the inspection parameter. If the inspection parameter indicates that one of the web components 1452, 1454 is out of alignment, drive system 1468 selectively steers the affected feed system (e.g., a conveyor) in a direction calculated to bring the affected web component back into a proper level of alignment.

Preferably, information exchange 1110 accumulates a plurality of inspection parameters corresponding to a plurality of products inspected. Information exchange 1110 then calculates a pertinent mathematical characteristic of the accumulated plurality of inspection parameters, such as, for example, an average and/or standard deviation. As a further example, information exchange 1110 accumulates the fifty most recently published inspection parameters and calculates an average/standard deviation, and repeats this process throughout a production run for each group of fifty inspection parameters published. The mathematical characteristic data is compared to one or more targets to determine whether the position of the first or second web component needs to be adjusted. In one embodiment, information exchange 1110 provides the average and standard deviation information to drive system 1468, and drive system 1468 determines whether a change is needed. In another embodiment, information exchange 1110 determines the need for a change and provides an indication to drive system 1468 as to how much of a change to make. It should be further understood that information exchange 1110 and drive system 1468 can share a common computer system for processing purposes.

A second operational example directed to FIG. 11 involves using camera inspection system 1464 as part of an outer control loop for controlling one or both web guides 1460, 1462. In this way, web guides 1460, 1462 provide pre-joinder web alignment control to maintain short term control. The outer control loop provides long-term control. More specifically, camera inspection system 1464 captures images of composite web 1458 (e.g., corresponding to each product produced or a statistical sample thereof). Inspection system 1464 detects the alignment/placement of the components of the composite web and publishes an inspection parameter accordingly. Information exchange 1110 accumulates a plurality of published inspection parameters and determines a mathematical characteristic of the accumulated plurality. In one embodiment, the determined mathematical characteristic comprises an average and/or standard deviation. The determined mathematical characteristic is compared to a target to determine whether the detected alignment/placement of the component parts of composite web 1458 is acceptable. If the difference between the detected placement and the target is unacceptable, it is next determined which component is out of alignment. Based on this latter determination, drive system 1468 adjusts a position of web guide 1460 and/or 1462 such that the alignment of the component parts of composite web 1458 returns to an acceptable level. Such adjustment may include, for example, mechanically and/or electrically adjusting a sensor associated with one or both of web guides 1460, 1462.

One particular operating example involves adjusting a web guide position using guides mounted on movable slides or arms (e.g., mechanically translatable). In this example, drive system 1468 adjusts the position of a rod on which web guide 1460 and/or web guide 1462 is mounted. The determination of which web guide, which web component and/or which web to move can be determined by a logic filter such as a filter for measuring the placement of each web or web component relative to a third component or a fixed point in the field of view of the inspecting camera (1464). Another example involves adjusting the hook placement relative to the outside edge of the side panel location. The hook web can be automatically adjusted by using a logic filter to steer a guide that feeds the hook into a cut and place module. As a further example, the logic filter may determine whether the first web component 1452 only should be selectively adjusted by adjusting guide 1460, whether the second web component 1454 only should be selectively adjusted by adjusting guide 1462 or whether both the first and second web components 1452 and 1454 should be simultaneously selectively adjusted by adjusting both guides 1460 and 1462. In this example, the drive system 1468 would be responsive to the logic filter to implement the determination of the logic filter.

In one preferred embodiment, information exchange 1110 provides an average and standard deviation of the plurality of inspection parameters to drive system 1468. Drive system 1468 compares one or both of these values to a target(s). Based on this comparison, drive system 1468 determines whether and by how much to adjust a position of one or both web guides 1460, 1462. It should be appreciated that information exchange 1464 can be configured to compare the determined mathematical characteristic to the target and to determine which web guide to adjust and by how much.

Also, if the mathematical characteristic deviates from the target to the point that an erroneous signal is suspected and/or web guiding errors are very large, drive system 1468 can be programmed to trigger a "blow-off" to clean any lint or other obscuring particles that may have accumulated on a web guide sensor.

One advantage of the embodiment illustrated in FIG. 11 is that machine vision systems are used to detect discrete and/or integral component placements and/or irregular edges that conventional web guides and web edge detector systems cannot detect. Also, the inspection system need not be located near the point of web control (e.g., near the web guides). For example, typical web guides with light bar or ultrasonic edge detectors do not accurately detect component placement in composite webs when the components are of similar densities, have similar light transmittance characteristics, or edges that are internal to a product such as edges in a closed portion of a training pant.

Similarly, typical edge detector web guiding systems may not be suitable for use with webs having irregular edges and/or "C-folding" edges where the web rolls over on itself. Traditional prior art web guides simply guide off of the folded edge, which can potentially place a component in an incorrect location. With a machine vision system as the detector (rather than or in addition to a typical edge detector), web width measurements are possible. It should now be appreciated that web width will change significantly if the web C-folds. In such a circumstance, the machine vision system can trigger a warning such as provide an alarm and/or effect automatic machine shutdown that may not have been triggered by an edge detector. For example, the drive system may include software which is a monitoring subsystem which monitors a parameter, such as width, of the composite web. The software would compare the monitored parameter to a preset range, which range would exclude C-folds. The software would provides an indication when the monitored width is outside the preset range (e.g., a monitored width below the range may correspond to a C-fold condition), wherein the indication is an alarm or a command to effect a shutdown of the web guiding system.

For example, composite web products, including disposable absorbent garments such as training pants, may require components having die cut outs with one or more angled edges. Typical edge detectors used with web guides do not adequately detect discontinuous web edges/components. A photoeye can be placed to detect the edge, but if the web moves in the cross direction a photoeye detecting scheme can lead to an incorrect conclusion that the die cuts (as opposed to the moving web) are out of position, possibly resulting in an incorrect adjustment. This problem occurs because the measurement is relative to the fixed position of the photoeye. A machine vision system used as part of a camera inspection system—such as system 1104 (FIG. 4A), system 1404 (FIG. 9), or system 1464 (FIG. 11)—can measure an absolute position of the die cut relative to its associated product component, instead of relative to the fixed sensor (e.g., photoeye) position. As an example, infant diapers typically include two fasteners, which may comprise a pair hook and loop fastener systems positioned on opposite sides of the diaper. These fasteners typically have an ear portion with a finger tab area. In one manufacturing process, these "diaper ears" are provided from a roll of material that is die cut to form the ears. A camera vision system positioned immediately downstream from the die cutter can inspect the width of irregular edges to ensure that the ears are cut correctly (e.g., to the middle). Such a camera vision system (or another vision system) can be positioned before the die cutter as well to provide web guiding improvements before the die cutting operation.

Referring still to FIG. 11, it should be appreciated that a web guiding system, such as system 1450, can be configured to adjust the position of the web to be guided (e.g., first web component 1452) by reference to a variety of reference points. For example, web guide 1460 can be configured to adjust the position of first web component 1452 by reference to a reference point. Such a reference point can be a fixed point (e.g. a mounting associated with web guide 1460), a reference point associated with the web being guided (e.g., a position of periodic reference mark placed on first web component 1452, as detected by inspection system 1464), and so on. Similarly, web guiding can occur by reference to multiple reference points, or by adjusting the position of one web component (e.g., second web component 1454) relative to a position of another web component (e.g., first web component 1452). Other references are possible.

One of the advantages of aspects of the systems and methods of the present disclosure is the ability to steer a web relative to a downstream inspection. In typical prior art systems, the web detector and web guide need to be located relatively close to one another to operate effectively to provide short term control. By using vision system information, it is possible to locate a sensor at a greater distance from the web guide and still maintain adequate long term web alignment control. Also, one sensor/camera system can detect the placement of multiple components and, as such, can control multiple webs. Further, using machine vision systems for web guiding allows web steering based on product (or process) attributes, as opposed to guiding to a sensor placement. In the context of prefastened training pants such attributes include, for example, die cut out placement and fastener overlap. In general, the drive system adjusts the position of the feed system at a particular point along the path and the vision inspection system captures an image at a particular point along the path which is downstream from the particular point along the path at which the drive system adjusts the position of the feed system.

Alternatively, it is also contemplated that the drive system adjusts the position of the feed system at a particular point along the path and the vision inspection system captures an image at a particular point along the path which is upstream of the particular point along the path at which the drive system adjusts the position of the feed system. For example, it is contemplated that a fastening process may be steered according to a product. Parts of the fastening process may be moved towards or away from the process centerline. If one side is at target and the other side is away from target, fold fingers on the non-target side may be moved to bring that side to target.

In addition, depending on the next, downstream process which will receive the web, it may be advantageous to guide the web according to a parameter of the next process. For example, a web may be guided into a joining process in which case a parameter related to joined parts may be used to guide the web. As other examples, a web may be guided into a cutting, folding or fastening process so that a cut, a fold or a fastened component or components, respectively, may be used to guide the web.

Further, disposable absorbent garments, including training pants 20, are commonly formed from composite webs of material, formed from spunbond/poly laminates. Traditional web guides and detectors can be used to control the delivery of each component, but they do not provide control over the placement of the resulting composite web. A machine vision system, however, can capture one or more images of the composite web (e.g., composite web 1458) and, using grayscale differences, detect different edges of the spunbond and the poly to determine proper alignment in the composite web. Thus, having a downstream machine vision system (e.g., a full product inspection system) provides distinct advantages over the prior art.

Information Display, Alarming, and Trouble Shooting

Referring again to FIG. 4A, in another aspect, information system 1110 is useful as a system for providing information to an operator associated with production line 1102. For example, information regarding inspection data can be displayed to the operator on operator interface 1118. Such information includes indications of the values of properties of the various components and aspects inspected by inspection system 1104 (e.g., an amount of overlap between fastening components 82, 84 of a training pant), an alarm indication when an inspected property falls outside of a desired limit or is trending toward a limit or otherwise requires the operator's attention, a troubleshooting indication prompting the operator to correct a detected problem (or that an automatic troubleshooting correction has taken place), and so on. Such a system allows the operator to react earlier than prior art systems and reduces the occurrence of automatic culls or other waste and delay. Similarly, when an automatic cull occurs, the operator is better able to determine exactly what measurement likely caused the cull.

In one embodiment, operator interface 1118 comprises a personal computer operating pursuant to a commercially available operating system such as Microsoft® Windows NT, and running one or more of a bundle of industrial and process information software applications such as Wonderware® Factory Suite™ 2000, available from Wonderware Corporation. Such an industrial and process information application preferably provides one or more of the following capabilities: display of process information such as inspection data (including information derived from inspection data), compare process information data to targets, real time relational database capabilities, and so on.

An operational description directed to inspecting an amount of hook-to-loop overlap between fastening components 82, 84 of fastening system 80 of a child's training pant 20 is instructive (FIGS. 10A–10D illustrate schematically such a fastening system). Inspection system 1104 (e.g., a machine vision system) inspects each training pant produced during a production run to identify an amount of overlap between fastening components 82, 84. Periodically, inspection system 1104 publishes an inspection parameter indicative of a characteristic of the inspected component—in this example, an amount of overlap detected. Information exchange 1110 obtains the published inspection parameters and, based thereon, provides a process display parameter for use by operator interface 1118. In one embodiment, information exchange 1110 accumulates a plurality of published inspection parameters corresponding to a plurality of training pants produced during a segment of a the production run (e.g., every 50 training pants produced). In such an embodiment, information exchange preferably computes a mathematical characteristic (e.g., an average and/or standard deviation) of the accumulated plurality of inspection parameters, such that the process display parameter corresponds to the mathematical characteristic.

Advantageously, the process display parameter, which is related to the inspected characteristic, is useful in a variety of ways. For example, with this information, operator interface 1118 can display a numeric and/or graphic of the inspected characteristic. More specifically, operator interface 1118 can display an indication of the inspected characteristic relative to a target such as, for example, a range of acceptable values or a trend line or a box-whisker plot. With this information, the operator can anticipate when a problem might occur and take corrective steps to avoid the problem.

Preferably, information exchange 1110 filters the information it receives from inspection system 1104). For example, and as discussed above, certain machine vision inspection systems rely on tools for determining positions of components within a captured image. If an inspection failure occurs, the vision system preferably provides an indication of the failure, in which case information exchange 1110 can disregard non-trustworthy inspection data associated with inspection failures. Information exchange 1110 may also filter incoming information to determine if the information is so far out-of-bounds as to be untrustworthy. Such untrustworthy information can be discarded and/or used to determine if the inspection system requires attention. It should be understood, that such filtering can also be accomplished by operator interface 1118, with information exchange 1110 simply passing unfiltered data.

It is also possible to display indications of a plurality of inspected components—using inspection system 1104 or multiple inspection systems. In some circumstances, it is desirable to correlate the information regarding the various inspected components (e.g., to a particular training pant produced or to a group of training pants produced in sequence) so that relationships between components can be monitored. Similarly, display indications can be grouped according to various criteria such as, for example, by inspection device (or location) and/or by the component being inspected. These types of groupings would have benefits in troubleshooting problems. Other display grouping criteria include grouping by a particular operational needs or events, such as grouping information based on an automatic cull event or when a new supply of material is spliced into the production line.

As mentioned above, apart from displaying inspection-related data on operator interface 1118, information system 1100 can also provide an alarming system. For example, if the amount of overlap between fastening components 82, 84 exceeds a target threshold, an alarm is automatically triggered. In one embodiment, operator interface 1118 makes this determination. But such a determination could occur elsewhere in system 1110, most notably information exchange 1110. An alarm may simply comprise a particular indication on operator interface 1118 (e.g., a flashing number or graphic, a change in size or color of a displayed number or graphic, and so on). An alarm can also include a signal to an alarming device 1130 associated with operator interface 1118. Alarming devices include, for example, sound devices (e.g., horns or buzzers), lights, and/or communication devices such as a pager, a computer, a personal digital assistant, a mobile telephone, a regular telephone, and so on.

Information system 1110 can further provide automated trouble-shooting support capabilities. For example, in addition to (or rather than) providing alarm indications, information system 1110 can compare inspection data to target data to determine whether a corrective action is required. The term corrective action is intended to include preventative actions as well. In some cases, such as adjusting set points or blowing off dust on sensors, the corrective action is preferably implemented automatically, without operator input. In other cases, a recommended corrective action is presented to an operator (e.g., a series of steps displayed on operator interface 1118). Still further, the information system can be configured to track the number of times a particular corrective action has been recommended/initiated.

FIG. 12 is a schematic representation of an exemplary automated trouble-shooting system (referred to generally therein as system 1500). The example illustrated relates to inspecting prefastened, refastenable training pants, such as training pants 20 described above, but the principles disclosed herein are applicable to the manufacture of a much broader range of products. In this example, a multiple camera inspection system (e.g., system 1104 of FIG. 4A) comprises three or more machine vision inspection systems positioned at various points in the manufacturing process. A first machine vision system 1502 is positioned to inspect a composite web of material 1504 on a product assembly conveyor. The composite web of material 1504 is formed by a forming/joinder process (e.g., a lamination process) 1506 carried out on two supplied web components 1508, 1510, such as that described with respect to system 1450 in FIG. 11. In one embodiment, the first machine vision system 1502 is referred to as a Product Assembly Conveyor ("PAC") linescan inspection system because it uses a vision camera mounted near the conveyor where the product is assembled. In this location, vision system 1502 is positioned to acquire images of each product being produced before the addition of an outer cover assembly.

A second machine vision system 1512 is positioned to inspect each training pant produced at a position 1514 after fastening system 80 is added to the side panels of each training pant by a fastening system application process 1516. In this context, the second machine vision system 1512 may also be referred to as a full product inspection system 1512. FIG. 12 schematically illustrates the supply of fastening components by reference character 1518. After the fastening system application process 1516, the web of products proceeds to a fastening engagement process 1519 where the fastening components are engaged to form a prefastened product. A third machine vision system 1520 is positioned downstream of the fastening engagement process 1519 and is referred to as an assembled fastening system inspection system 1519 or a fastening seam inspection system because it inspects the fastening seam of the completed training pants 1522 after fastening engagement process 1519.

Preferably, machine vision systems 1502, 1512, and 1520 communicate with information exchange 1110 and/or operator interface 1118 via a communication network such as network 1124. Other forms of data/information transfer are also possible, such as dedicated lines or daisy chained communications.

In general, machine vision systems 1502, 1512, and 1520 publish inspection data, such as that already described herein relating to the inspected components of each training pant 1522 produced, for use by information exchange 1110. In this context, information exchange 1110 comprises a logic system that accumulates inspection data (e.g., from the fifty most recently inspected products) from machine vision systems 1502, 1512, and 1520 and determines an average and standard deviation calculation of the accumulated data. The average and/or standard deviation data is thereafter incorporated into a spreadsheet (e.g., Microsoft® Excel) where a series of logic statements sort the information (e.g., by comparing the average and/or standard deviation data to reference target values), to produce recommended corrective action(s), if necessary. The recommended corrective action(s) can be displayed to an operator on operator interface 1118 and/or automatically performed. For example, for some problems, the corrective action includes a series of steps to be performed by the operator or another technician. For other problems, the corrective action can be automatically initiated (e.g., initiating a blow off procedure to clean a photodetector). If the logic recommends multiple corrective actions, the logic preferably organizes the recommended actions to prioritize the order in which the actions are displayed to the operator and/or implemented automatically. It should be understood that information exchange 1110 can also be configured to simply pass inspection data (e.g., "raw" data, or averages and standard deviations based on accumulated data) information to operator interface 1118. In such a case, operator interface 1118 preferably incorporates the logic system functionality. It should further be understood that the logic functions may be implemented directly in dedicated software.

For example, in one embodiment, it is contemplated that a Visual Basic (VB) application program may be used to read data from the reflective memory network, compute an average and standard deviation, and then publish the summary statistics back out to the reflective memory. The summary statistics would then be available for display, such as by Wonderware® Factory Suite™ 2000, available from Wonderware Corporation, or available for analysis by a logic routine. In this embodiment, the VB application program may perform the functions performed by the DLL files noted herein.

The foregoing description, focusing on a spreadsheet-based approach is provided for exemplary purposes only. In one embodiment, rather than using a commercially available spreadsheet, a logic program is used. For example, and as described above, such a logic program can be written in RSLogix™ 5000 software and run on a SoftLogix™ PC platform within information exchange 1110 A dynamic link library (DLL) file (e.g., in C language) retrieves inspection data from network 1124 (e.g., a reflective memory network) and places the retrieved data into a data array. Another C language DLL performs mathematical manipulations, as desired, on the data array. For example, in one embodiment a DLL performs statistical calculations on the data array such as determining averages and standard deviations. Thereafter, the RSLogix™ program uses the statistical information to perform the desired functions (e.g., determining quality by comparing the statistical information to a target, determining an alarm conditions, determining process setting changes, and so on), in accordance with the present disclosure, so that recommended actions can be published to the machine operator and/or automatic commands may be sent to the machine to make a change.

Referring still to FIG. 12, in one exemplary operational scenario, joinder process 1506 is a lamination process for laminating web component 1510 to web component 1508 to form composite web 1504. Machine vision system 1502 periodically captures images of composite web 1504 corresponding to substantially a training pants being produced during a production run (e.g., a given time period during a production cycle). Machine vision system 1502 determines the placement of web component 1510 relative to web component 1508 based on grayscale differences in the captured images. Information exchange 1110 accumulates the inspection data published by machine vision system 1502 (e.g., for the fifty most recent inspections) and determines an average and standard deviation of the accumulated data. The average and standard deviation data are stored in the data array and logic statements determine whether component 1510 is positioned correctly relative to component 1508 by comparing one or both of the average and standard deviation values to a target reference. If the logic determines that the alignment of components 1510 relative to 1508 is unacceptable, the logic will recommend an adjustment of a position of component 1510 prior to joinder process 1506 (e.g., by a directing a web guide change or by directing a steering correction of a conveyor supplying component 1510). The logic makes this recommendation because it is programmed to know that component 1510 is applied to component 1508 and it is normally preferable to move the object being attached (in this case 1510) to a "base" component (in this case 1508). Advantageously, by recommending a proper order of corrective actions prevents an operator from "tail chasing" and reduces the likelihood that a corrective action merely fixes a symptom rather than a source of a problem.

With the benefit of the present disclosure, it should be understood that there exist a number of ways to identify a recommended corrective action. Three exemplary approaches will now be described. A first approach uses the calculated averages of accumulated inspection data. The averages are imported into a spreadsheet and logic statements compare the averages to target values and associated tolerance range(s). Based on a difference between an average and a target, the logic is programmed to recommend and/or initiate a corrective action. With such an approach, a single item of inspection data that is out of bounds would not trigger a corrective action because the use of averages tends to smooth out spurious occurrences. A second approach for identifying recommended corrective actions uses a "percent defective" determination based on both the calculated averages and standard deviations of the accumulated inspection data from the relevant machine vision system(s). Thus, the logic compares the actual percent defective in a given sample (e.g., the fifty most recent inspections) to a target percent defective to determine if and where any corrective action is required.

A third approach for identifying corrective recommended corrective actions compares both the average and standard deviation against their respective targets. The average deviating from its target may indicate that a different corrective action is required than if the standard deviation deviates from its target, or that a different corrective action is required than if both numbers deviate from their targets. For example, referring to the previously discussed example of using photoeyes to detect pant spacing after the final cut off, a high standard deviation of spacing may signify a belt slip issue while a high or low average spacing can signify that a process change (perhaps machine draw) needs to be made.

It should also be understood that that the systems and methods disclosed herein are not limited to using mathematical/statistical determinations in the forms of averages, standard deviations, and percent defectives. With the benefit of the present disclosure, it is possible to choose other mathematical/statistical calculations that will yield acceptable results in a given application.

Both of these approaches provide advantages over the prior art. For example, with even a small number of inspection data points to monitor, it is difficult for a process operator to track such data as it is being presented, mentally process the information, determine whether a corrective action is needed, and then determine what corrective action to take.

It should be appreciated that in one embodiment, information exchange 1110 simply supplies inspection information (e.g., an average and/or standard deviation of the fifty most recent measurements of the overlap between fastening components 82, 84) to operator interface 1118, and operator interface 1118 compares that data to one or more targets and determines what to display and how to display it, whether an alarm condition is triggered, whether to filter the data, whether a troubleshooting action is required, and so on. In another embodiment, however, information exchange 1110 makes one or more of the foregoing determinations and simply passes a parameter or command message to operator interface 1118 which thereafter displays that which has been commanded by information exchange 1110 Further, although it is preferred that each product produced be inspected, the foregoing automated trouble-shooting system can be effectively implemented using a sampling set such as a set based on a statistical sampling plan.

Figure 13A:
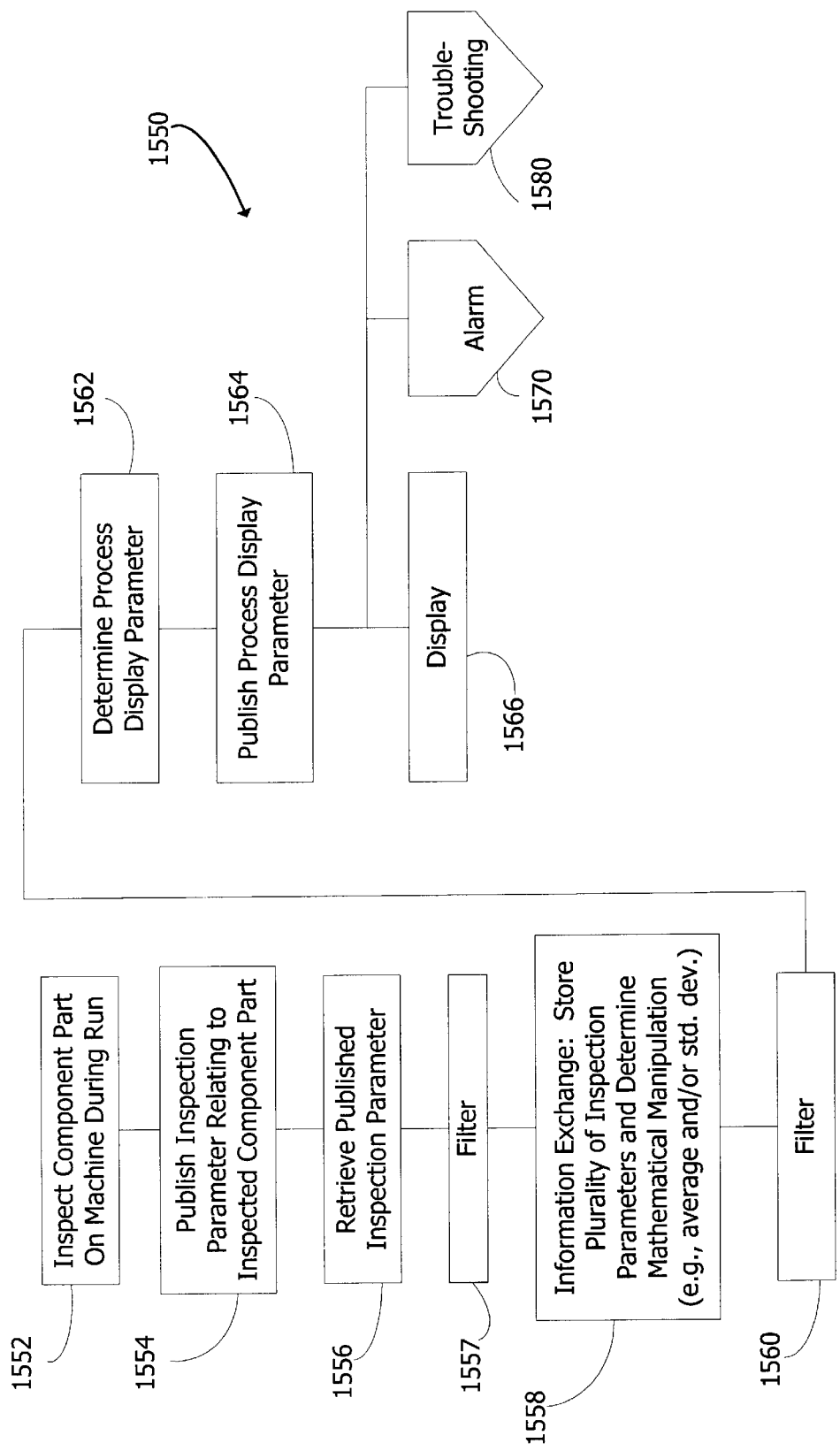
FIGS. 13A and 13B are logic flow diagrams illustrating one method of providing process information, suitable for use in connection with an information system such as that illustrated in FIG. 4A.
Figure 13B:
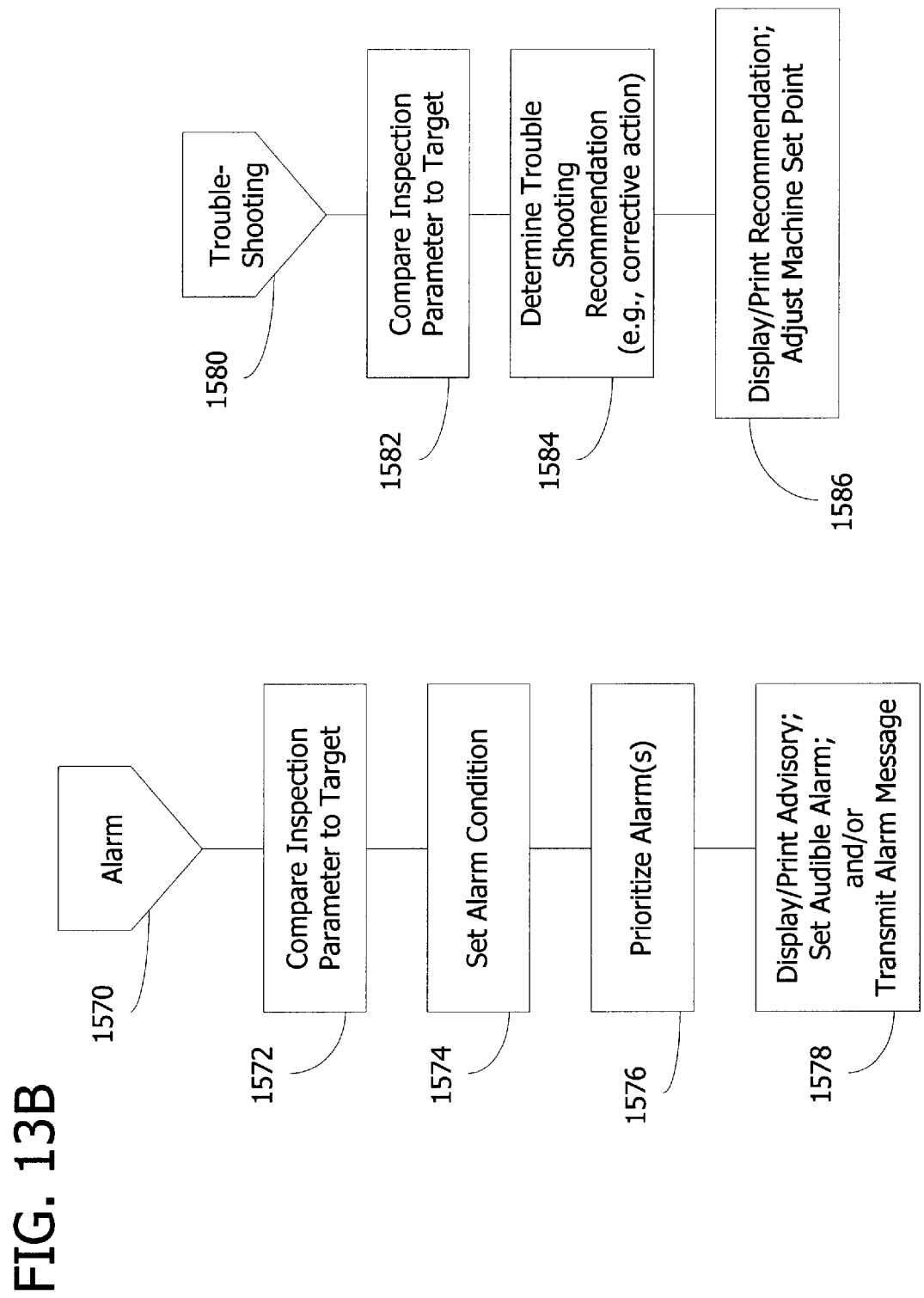

FIGS. 13A and 13B are logic flow diagrams illustrating one method (indicated generally by reference 1550) of providing process information, suitable for use in connection with an information system such as that illustrated in FIGS. 4 and/or 12. More specifically, FIG. 13A illustrates, in logic flow format, a method for providing process information to an operator in real time. Such a method is suitable for use in connection with a manufacturing production line producing composite products, such as disposable absorbent garments, from a sequential addition of component parts. At block 1552, an inspection system (or a plurality of inspection systems—such as those illustrated in FIGS. 4 or 12) inspects one or more component aspects of disposable absorbent garments produced during a production run. Thereafter, at block 1554, the inspection system provides an inspection parameter that indicates a characteristic of the inspected component. For example, if the inspection system is configured to inspect an amount of overlap between fastening components 82, 84 of training pants 20 produced during a production run, the inspection system preferably provides a numeric value of the amount of overlap detected in each training pant inspected. At blocks 1556, 1558 an information exchange (e.g., information exchange 1110 ) obtains and stores the inspection parameters provided by the inspection system. As indicated at block 1558, in one embodiment, the information exchange computes an average and standard deviation of an accumulated plurality of inspection parameters corresponding to a plurality of inspected products (e.g., the fifty most recently inspected products).

Blocks 1557 and 1560 are intended to illustrate that inspection data may be filtered at one or more points in the method, and based on various filter criteria. For example, in one embodiment the information exchange disregards (or discounts) inspection parameters that fall outside of a range of acceptable values, indicating that the inspection parameter is suspect. Similarly, the information exchange can disregard inspection parameter data if the inspection system indicates that an inspection failure relating to the data has occurred. In another embodiment, such filtering occurs elsewhere, such as at operator interface 1118.

At block 1562, one or more process display parameters are determined based on the inspection data. The process display parameter(s) indicates what information should be displayed to an operator, e.g., on operator interface 1118 (block 1564, 1566). Such information includes numerical and/or graphical indications of the inspection parameter, indications of the average and/or standard deviation of the accumulated plurality of inspection parameters, comparisons to one or more targets, alarm indications and messages, trouble-shooting recommendations (e.g., corrective actions and automated corrective responses), and so on. In one embodiment, the process information display determines the process display parameter. In another embodiment, operator interface 1118 determines the process display parameter.

FIG. 13B further illustrates, in flow diagram form, exemplary methods for providing alarm and trouble-shooting indications (blocks 1570, 1580). Referring first to providing alarm indications, at block 1572 the inspection data is compared to a target. This includes comparing the inspection parameters directly, as well as comparing information derived therefrom, including average and standard deviations and display parameters. If the inspection data as compared to the target is unacceptable, an alarm condition is triggered at block 1574. For example, if a particular item of inspection data is trending toward a limit, the operator may be notified so that he/she can take corrective action before the limit is met.

Because the present method may be used in connection with a system that inspects a large plurality of components, it is possible that multiple alarms will be triggered at or near the same time. Thus, at block 1576, the alarms are prioritized according to importance. For example, an alarm indicating a critical failure would take priority over an alarm indicating that an item is trending toward a limit.

As another example, the system is programmed to prioritize alarms to correspond to the sequence of manufacturing steps involved in making the product. A more particular example involves alarming in connection with the manufacture of prefastened training pants. In one embodiment of such an example, alarming is based generally on the sequence of steps for constructing a training pant. This approach translates into alarming based on the location of inspection points along the manufacturing process. More specifically, and still referring to the example of prefastened training pants, fastening components 82, 84 of training pant 20 are applied to side panels 34, 134. If both side panels 34, 134 and fastening components 82, 84 were misplaced, the alarms would be prioritized in order of unit operations in the pant manufacturing process. Thus, the alarm for the side panel 34, 134 placement would be programmed to have a higher priority than the alarm for fastener component 82, 84 placement because side panels are applied earlier in the pant construction process.

Still another example involving the manufacture of prefastened training pants is instructive at this point. To alarm for hook 84 cross direction (CD) placement relative to side panel 34, the program will have checked, in the following order: the separation of the inside edge of the side panel 34, the width of each of the side panels 34, and then the distance from the inside edge of the hook 84 to the outside edge of the side panel 34. Similarly, to alarm for hook 84 machine direction (MD) placement, the alarm program checks in the following order: MD placement of the side panels relative to the absorbent assembly 44, the MD placement of the panels with respect to each other, the hook length, and finally the hook MD placement relative to the edge of the side panel. In these cases, if all of these checks result in an indication of an erroneous placement, the program prioritizes the alarms to alarm the first failed check first and the last failed check last.

Block 1578 indicates that the alarm indications can take on any of a number of forms. In a simple form, an alarm is simply an indication on a display associated with operator interface 1118. Other indications include audible alarms, flashing lights, and/or alarm messages sent to electronic equipment such as telephones, mobile telephones, pagers, computers (e.g., email), and so on.

Referring still to FIG. 13B, block 1580 relates to a method of providing an automated trouble-shooting response. At block 1582, the inspection data is compared to a target. This can include comparing the inspection parameters directly, as well as comparing information derived therefrom. Preferably, the comparison is done in either an information exchange (e.g., information exchange 1110) or an operator interface computer (e.g., operator interface 1118). If the comparison indicates an error condition (e.g., a misalignment of components), a corrective action is indicated to an operator, such as on a display associated with operator interface 1118 (block 1586). Alternatively, or in addition to displaying a corrective action, an automatic response, such as a machine set point adjustment or a conveyor steering command, is triggered.

Providing troubleshooting responses and/or alarm indications may also be accomplished by identifying relationships between inspection parameters and machine settings. For example, after inspecting an aspect of the composite product being constructed, one or more component attributes may be automatically identified by the inspection system. The component attribute is obtained by a system such as information exchange 1110 that also determines a machine setting associated with the construction process. If the component attribute falls outside of acceptable limits (e.g., as determined at block 1582 of FIG. 13B, the information exchange can identify the troubleshooting recommendation (see block 1584 of FIG. 13B) as a function of an identified relationship between the component attribute and the determined machine setting. Such a capability can be used to identify relationships between one component attribute and one or more machine settings (including settings from multiple machines), as well as between multiple component attributes and multiple machine settings. For example, machine vacuum and/or blowoff settings may be related to one or more inspected component attributes to identify and/or isolate a troubleshooting action. Using refastenable training pants as an example, if a hook cut length problem is detected (e.g., at block 1582 of FIG. 13B), information exchange 1110 can check to see if the associated vacuum setting is within an expected range. Thus, a relationship between the hook cut length problem and the vacuum set point can be identified to the operator and/or the vacuum setting can be automatically adjusted in a direction determined to alleviate the detected hook length problem.

Figure 14:
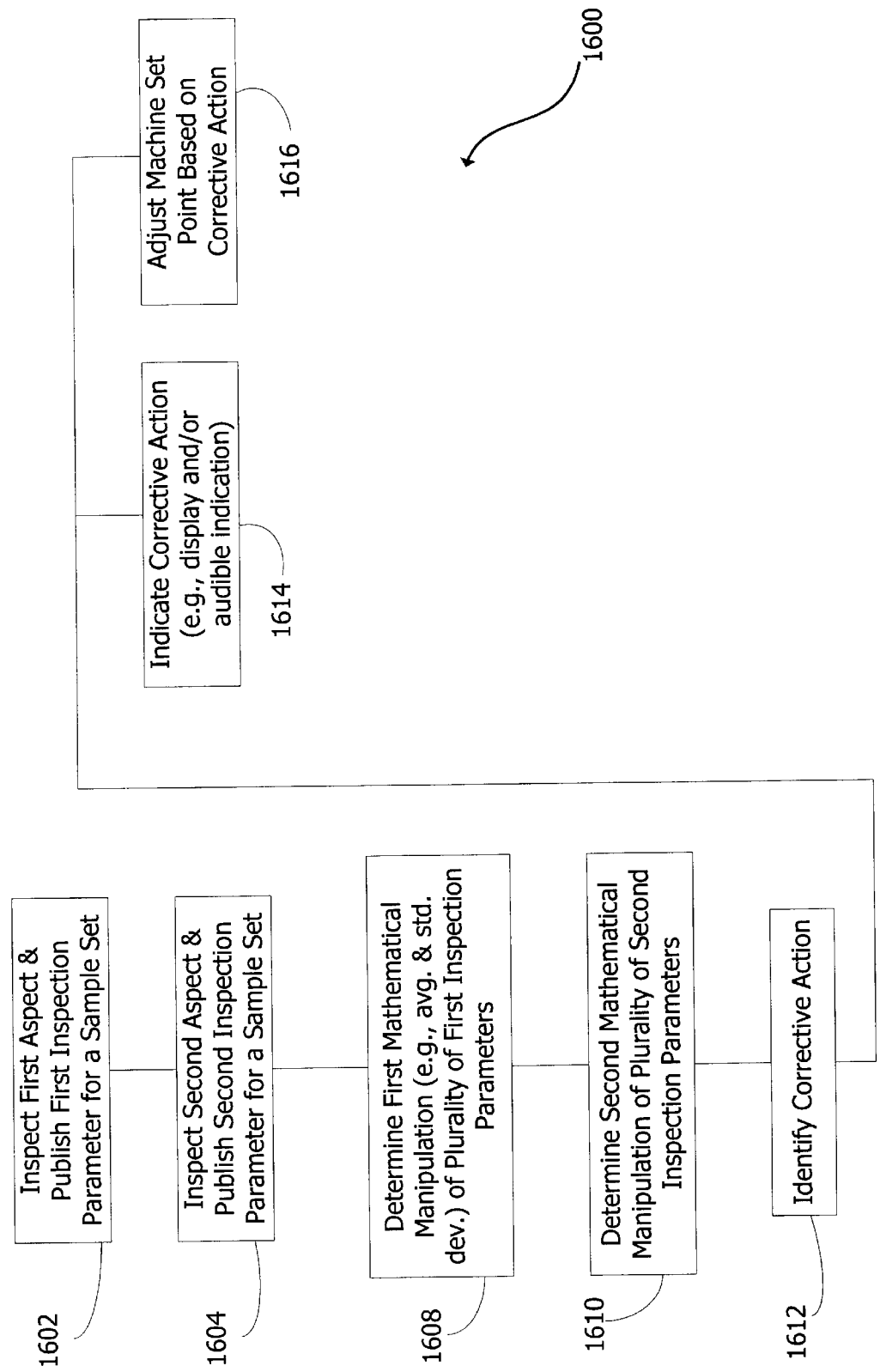
FIG. 14 is a logic flow diagram illustrating one method (indicated generally by reference 1600) of providing an automated trouble- shooting capability, suitable for use in connection with an information system such as that illustrated in FIGS. 4 or 12.

FIG. 14 is a logic flow diagram illustrating one method (indicated generally by reference 1600) of providing an automated trouble-shooting capability, suitable for use in connection with an information system such as that illustrated in FIGS. 4 and/or 12. In particular, the method 1600 is suitable for use in connection with a manufacturing process having at least one machine operating at a set point and producing disposable absorbent garments from a sequential addition of component parts during a production run. At block 1602, an inspection system (e.g., one or more of the inspection systems illustrated and described in connection with FIGS. 4 or 12) inspects a first aspect of substantially all of the garments being manufactured and provides a first inspection parameter correlated to an inspected garment. For example, in FIG. 12, inspection system 1502 inspects a composite web 1504 formed by the joinder of web components 1508, 1510 and detects a measurement of the alignment of components 1508, 1510. At block 1604, a second aspect of the product being produced is inspected and a second inspection parameter is provided.

Using FIG. 12 again as an example, inspection system 1520 comprises a full product machine vision system for inspecting the finally assembled product, in this case a child's training pant (reference 1522 in FIG. 12) having a refastenable fastening system 80 (see FIG. 1). Inspection system 1520 preferably is capable of detecting a plurality of points/characteristics of each training pant produced (or a statistical sample set of each product produced). For example, inspection system 1520 can inspect the final product 1522 to determine if the portion of that product formed from composite web 1504 is correctly aligned. Based on the first and second inspection parameters, a logic system (e.g., logic residing in either information exchange 1110, operator interface 1118, or elsewhere) determines whether a corrective action is required.

Advantageously, by using inspection data from more than one inspection source, the logic can better pinpoint the source of possible problems. For example, if the inspection parameter(s) published by inspection system 1502 (FIG. 12) relating to a given product (or group of products) does not indicate a misalignment with respect to components of composite web 1504, but inspection system 1520 detects an alignment error in the final product (or group of products), the logic system can determine that the problem most likely occurred downstream from joinder process 1506.

Referring still to FIG. 14, blocks 1608 and 1610 indicate that in one embodiment, the "raw" inspection data is accumulated. Mathematical characteristics of the accumulated data (e.g., averages and standard deviations) are calculated and it is these mathematical characteristics that are analyzed by the logic system to determine whether a corrective action is required. It should be appreciated that the use of data from a plurality of inspection events reduces the likelihood that spurious errors and/or erroneous readings will trigger a corrective action. It should also be appreciated that the use of data from a plurality of inspection events allows for alarming based on variability of inspected events, instead of or in addition to alarming based on deviation from set point.

Once a corrective action is identified/triggered (block 1612), the method proceeds to block 1614 and presents an indication of the corrective action to an operator (e.g., on operator interface 1118) and/or initiates an automatic set point adjustment (e.g., steers a conveyor or adjusts a cutting process) at block 1616.

At this point, it is instructive to note that the information exchange concept disclosed and described herein provides a powerful innovation in that it makes possible the ability to relate multiple data points to each other, whether those data points originate from a single inspection system, multiple inspection systems, or other manufacturing-related databases (e.g., raw material data, waste/delay data, quality data, machine set point data, and/or registration data). Thus, while obtaining data from multiple locations is possible, it is not critical. In other words, it is first important to obtain the desired data (e.g., inspection data), and then important to process the obtained data points for decision making purposes. In this regard, the information exchange facilitates an expert system that is programmed to follow a logical analytical process (developed by human experts). Advantageously, the use of computer processors allows for the performance of the necessary calculations, comparisons, and logical assessments on a large number of data points considerably faster than humanly possible.

Referring again to FIG. 12, an operational example based on manufacturing training pants is described. In this example it is assumed that it is desirable, from a quality perspective, to cull products in which the hook 84 is not placed within a preferred distance from an edge of the side panel 34 near the leg edge of the training pant 20. Notifying an operator associated with the manufacture of the product of the proper corrective action may include processing information from more than one inspection system. In the illustrated embodiment, a first machine vision system 1502 detects the placement of side panels 34 and 134 with respect to some other component of the pant being constructed, such as, for example, absorbent assembly 44, and preferably from a plurality of inspection events. By using a plurality of inspection events, it is possible to obtain an average value (e.g., for the fifty most recent inspection events). A second machine vision system 1512 is positioned to inspect each training pant produced at a position 1514 after fastening component 84 is added to the side panels (by fastening system application process 1516). For instance, the second machine vision system 1512 detects a measurement of the length of fastening component 84 along the longitudinal axis 48. The same inspection system 1512 can also be used to detect a position of fastening component 84 relative to the edge of side panel material 34 at a position near the leg opening of the assembled pant. A third machine vision system 1520 is positioned to measure the length along the longitudinal axis 48 of side panel 84. The measurements from one or more of these plurality of inspection events at each inspection system (1502, 1512, and 1520) may be passed to a computer system (e.g., information exchange 1110 ) capable of calculating averages and standard deviations of the accumulated data, comparing the calculated values to set points and/or quality limits to determine a percent defective, and to determine if any of the four measurements taken by the three inspection systems falls outside of quality limits. In one embodiment, a logic system associated with information exchange 1110 prioritizes the above-noted four measurements in the following order: (1) side panel machine direction (MD) placement; (2) fastening component (e.g., hook) length; (3) fastening component (hook) placement relative to side panel; and (4) front panel length. If side panel MD placement is incorrect, placement is phased in a direction selected to correct the MD placement. If MD placement is satisfactory, then the hook length is analyzed and corrected, if necessary. If the hook length is satisfactory, then the MD placement of the hook is analyzed and, if incorrect, the alarming system could be triggered to suggest a corrective action. If the hook MD placement is satisfactory, then the front panel length is analyzed. If this measurement is unsatisfactory, the product cut off section of the machine can be phased (either automatically and/or by notifying the operator of a corrective action) to correct that front panel length. If all four of these checks "pass," the hook is considered placed correctly and the pant is not culled.

At this point, it is instructive to identify yet another example of the power of the presently disclosed systems and methods to interrelate data from a variety of systems and information sources. Information from multiple camera inspection systems (e.g., inspection system 1104 of FIG. 4A) can be combined to automatically interpret the locations of various components of a composite product formed by the sequential addition of component parts, such as a child's training pant. One example of such a capability involves controlling placement of a final cut off, measured as a length of an endseal, using information from three vision systems: (1) a product assembly conveyor vision system; (2) a full product vision system; and (3) a fastening vision system. The product assembly conveyor vision system can be used to control longitudinal placement of the leading edge of the side panel relative to the trailing edge of an absorbent pad (see absorbent assembly 44 of FIGS. 1–3). This approach ensures that the side panel is put in a correct longitudinal place on the product being manufactured, in this case a training pant. Next, the full product inspection system camera measures the longitudinal length from the leading edge of the side panel to the trailing edge of the side panel at the leg cut out. Third, the final cut off can be controlled by measuring the longitudinal length of the front panel at the fastening vision system camera. Thus, knowing that the panel is the correct length and is in the correct location relative to the pad, it is possible to place the final cut off in the right location, measured by the front panel length, and interpolate that the endseal is the correct length. Advantageously, in one embodiment information exchange 1110 performs these calculations for displaying the relative measurements to an operator. Also, because there is no practicable automatic method for detecting endseal length directly, process information exchange 1110 can perform the mathematical calculations, based on the measured data, to determine by inference whether the endseal needs to be moved. With this information, the operator can make an adjustment, if necessary, or an automatic adjustment may be triggered. In other words, the inspection system 1104 detects the relative placement of first and second components and of second and third components. The information exchange 1110 infers the relative placement of the first and third components from the relative placement of first and second components and from the relative placement of second and third components. The information exchange 1110 uses the inferred relative placement of the first and third components for guiding the first or third components.

The following are examples of inferring the placement of components and using the inferred information for guiding system control or for controlling its operation. In a more general case, the inspection system would detect the relative placement of first and second components and of second and third components. In response, the information exchange system would infer the relative placement of the first and third components from the relative placement of first and second components and of second and third components. The information exchange system would use the inferred relative place of the first and third components for guiding the first or third components. In a specific case, an upstream vision camera detects a location of component 1 relative to component 3 (both on web 1). After a joining process, a downstream vision camera detects a location of component 2 relative to component 3. In this example, component 1 cannot be seen by the downstream camera because it is beneath component 2. However, the placement of component 1 relative to component 2 is an attribute of interest. The system infers the placement of component 1 relative to component 2 by performing mathematical operations on the vision system measurements provided by the upstream and downstream cameras, e.g., by knowing the placement of component 1 relative to component 3, and component 2 relative to component 3, the placement of component 1 relative to component 2 can be inferred.

It should be appreciated that the systems and methods disclosed herein, including those directed to information displaying, alarming, and trouble-shooting, can be based on data associated with inspecting one or more component parts associated with one or more products being constructed, as well as, data associated with inspecting multiple aspects of a single component part (e.g., using multiple vision systems to check the placement of a component part).

It should further be appreciated from the foregoing examples that alarming notifications and trouble-shooting/set point change actions (including those automated and those indicated to an operator on an operator display) are preferably prioritized. For example, it is preferable to provide alarm notifications in a logical order. Preferably, the order is chosen in terms of importance. One way to organize alarms and/or trouble-shooting actions is by order of occurrence. More preferably, however, alarms and trouble-shooting actions are prioritized by logical importance in terms of their respective relationship to a most-likely root source of the condition resulting in the alarm or trouble-shooting action. For example, if a measurement anomaly is detected at multiple points during a high speed web converting process, it may be preferable to prioritize any alarm or trouble-shooting action in process order (i.e., the first detection point being nearest a most-likely root source). Other logical priority schemes may be advantageously employed with the benefit of the present disclosure.

Exemplary Displays

Figure 15:
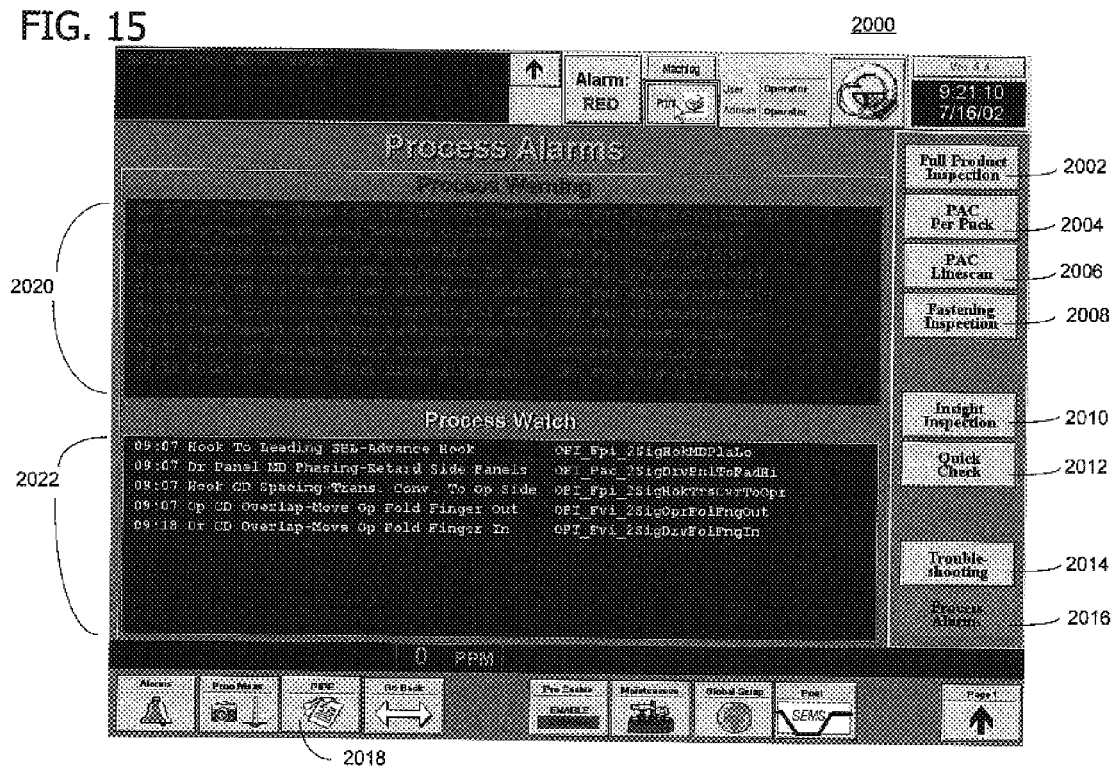
FIGS. 15–19 illustrate certain exemplary display information for display on an operator interface associated with a manufacturing process.

FIGS. 15–19A illustrate exemplary display information for display on an operator interface associated with a manufacturing process. The illustrated examples focus on manufacturing prefastened training pants, such as training pant 20 of FIGS. 1–3. FIG. 15 illustrates an exemplary display screen based on the above-described Wonderware® Factory Suite™ 2000, available from Wonderware Corporation. As illustrated in FIG. 15, a display screen 2000 has been configured and arranged to correspond to functions associated with the manufacture of training pants 20.

Figure 19:
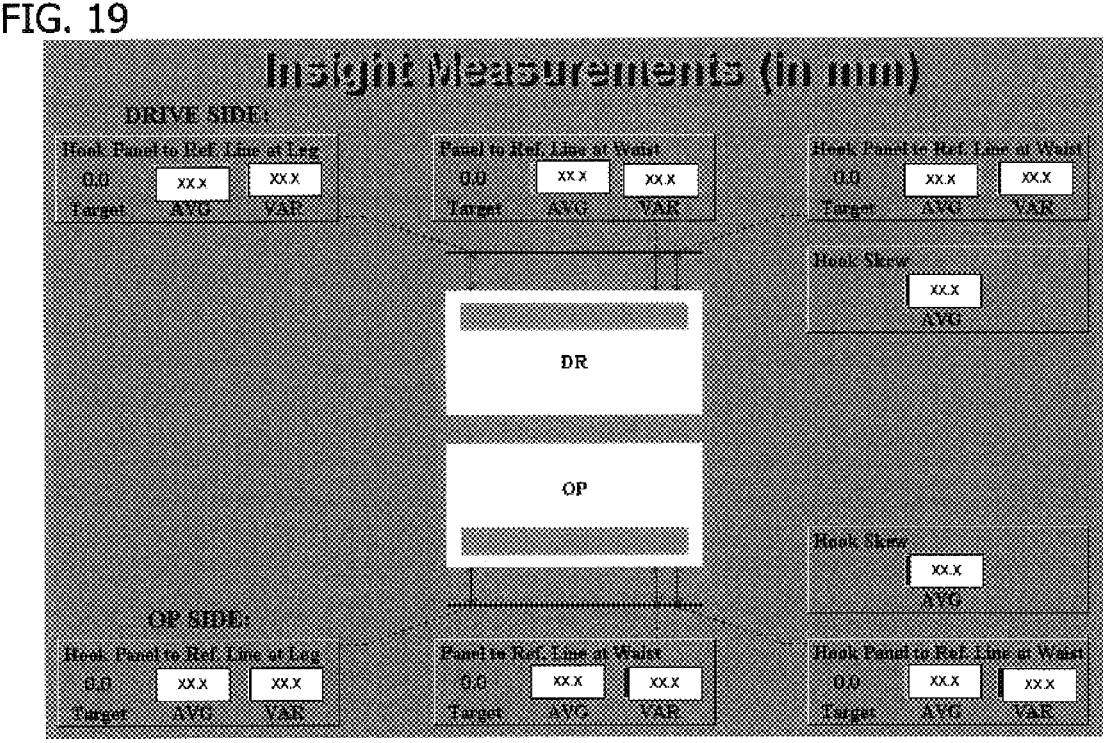
Figure 19A:
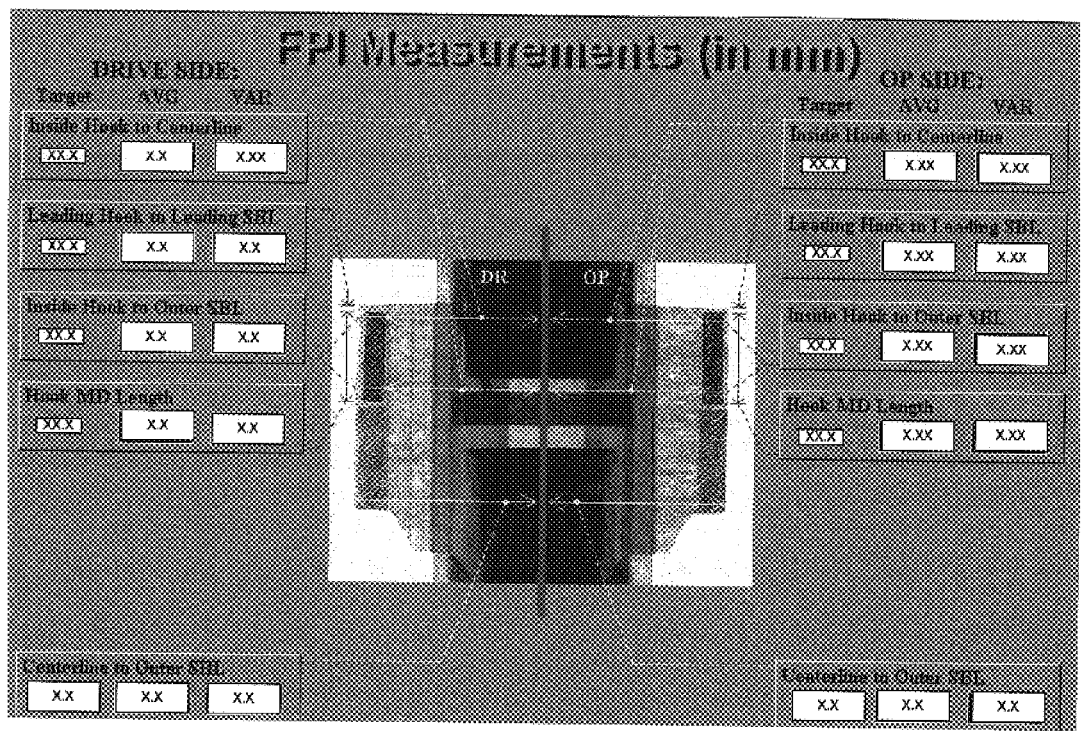
FIG. 19A illustrates an exemplary display of full product inspection information of a fastening system associated with a refastenable child's training pants as displayed on an operator interface.

Proceeding around the display screen 2000 in a generally clockwise fashion, displayed there on are a plurality of options for enabling the operator to select the type of information for display. A full product inspection (FPI) option is indicated at 2002. In the illustrated example, selecting the FPI option 2002 causes a display of inspection data from a full product inspection machine vision system (e.g., system 1512 of FIG. 12). FIG. 19A illustrates an exemplary display of full product inspection information of a fastening system associated with a refastenable child's training pants, as displayed on an operator interface. FIG. 19A provides an example of information displayed in connection with FPI option 2002. The next option 2004 enables a display of data relating to an applicator process, which will be discussed below in connection with FIG. 20 and FIG. 21. Display option 2006 enables a display of PAC linescan measurements. In the present example, the PAC linescan inspection system (e.g., inspection system 1502 of FIG. 12) includes a camera located at a position before the outer cover of the training pant 20 is applied, and can detect component edges and placement that would be hidden or otherwise more difficult to inspect by the placement of the outer cover. Option 2008 enables a display of an inspection system for inspecting fastening system 80 (e.g., inspection system 1520 of FIG. 12). Display option 2010 enables a display of so-called "Insight" measurements. In particular, these measurements refer to measurements of a Cognex In-Sight™ 3000 vision system, but are intended to be exemplary of the other inspection systems associated with the overall information system. Display option 2012 enables a display of "quick check" data. The quick check display screen is preferably configured to display certain critical values for the product in question. In this case, the quick check display is configured to display measurements that trigger product culls. Also displayed may be measurements that most often (e.g., typically based on experience or data analysis) require operator adjustments. Stated differently, the quick check display provides a convenient display of information that will often be of very high importance to an operator, such as information to help troubleshoot high cull occurrences. Advantageously, such a display screen saves time by reducing the number of displays an operator needs to monitor (i.e., it displays information that may be available on other screens, in a single, highly organized manner).

Display option 2014 enables a display of troubleshooting recommendations and/or actions. Display option 2016 enables a display of process alarms and watch conditions. In FIG. 15, process alarm option 2016 is enabled. Other display options include, for example, an option 2018 to access a so-called PIPE database. In this example, the PIPE database stores data relating to waste and delay.

Referring still to FIG. 15, in the illustrated embodiment, process alarms are grouped into two categories: process warnings 2020, and process watches 2022. In this example, process warnings are considered to have greater relevance to the operator than process watches. Thus, it is appropriate to use colors to differentiate the two categories (e.g., red for warnings and yellow for watches).

Figure 16:
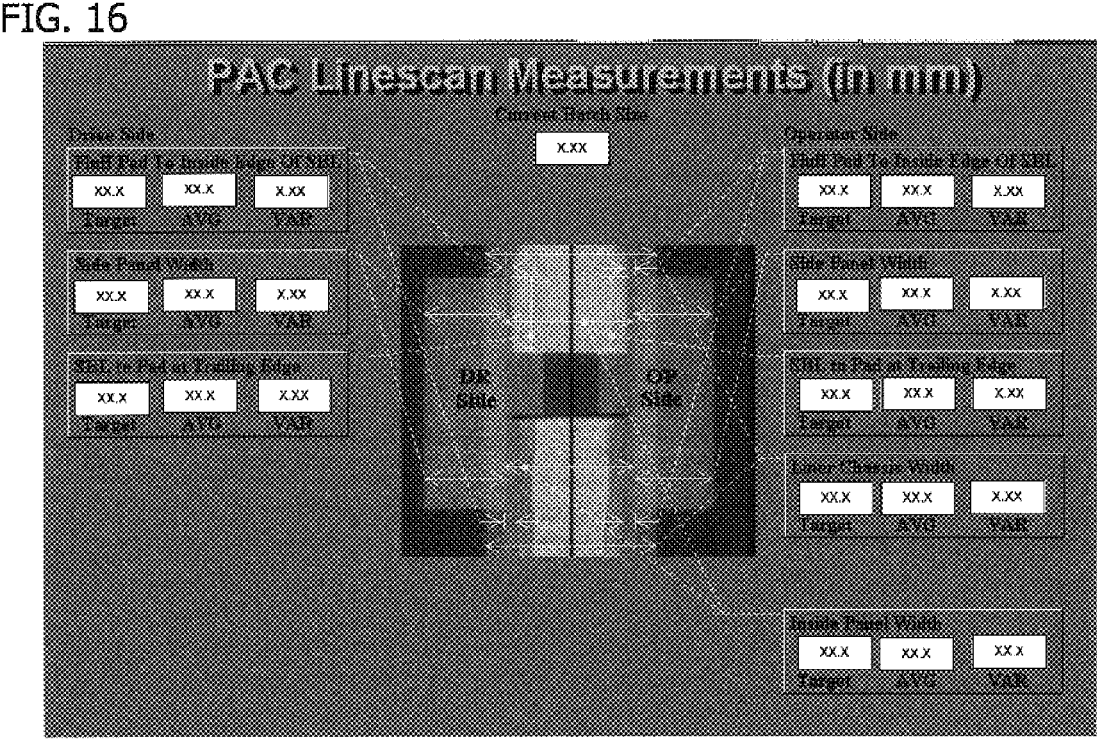
Figure 17:
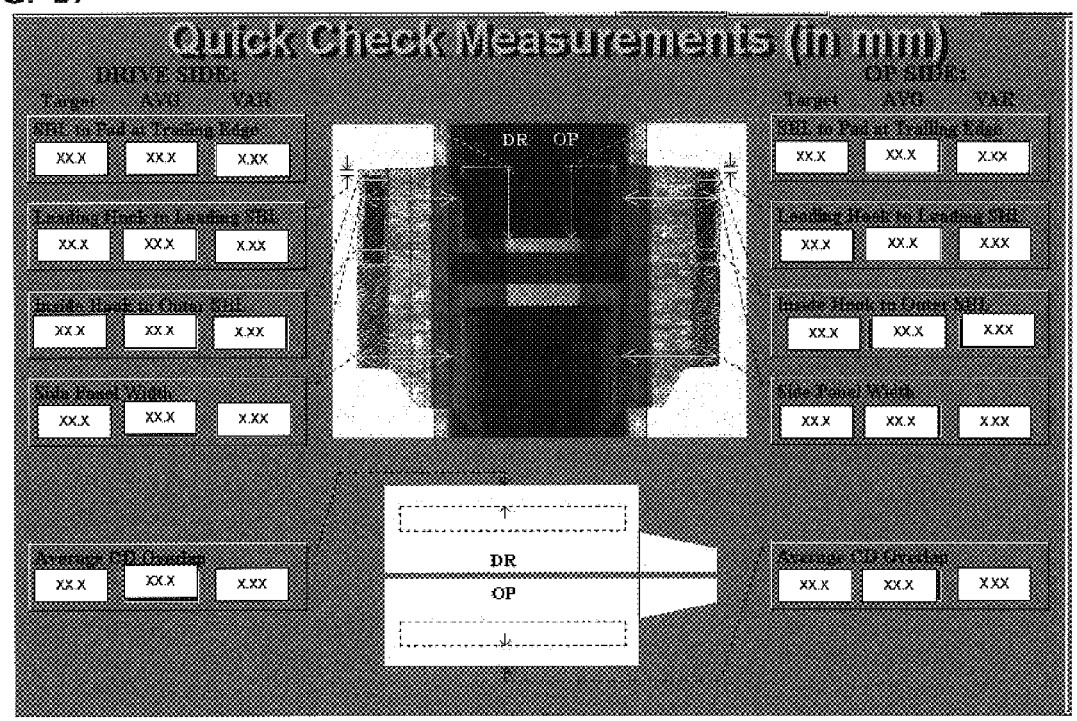
Figure 18:
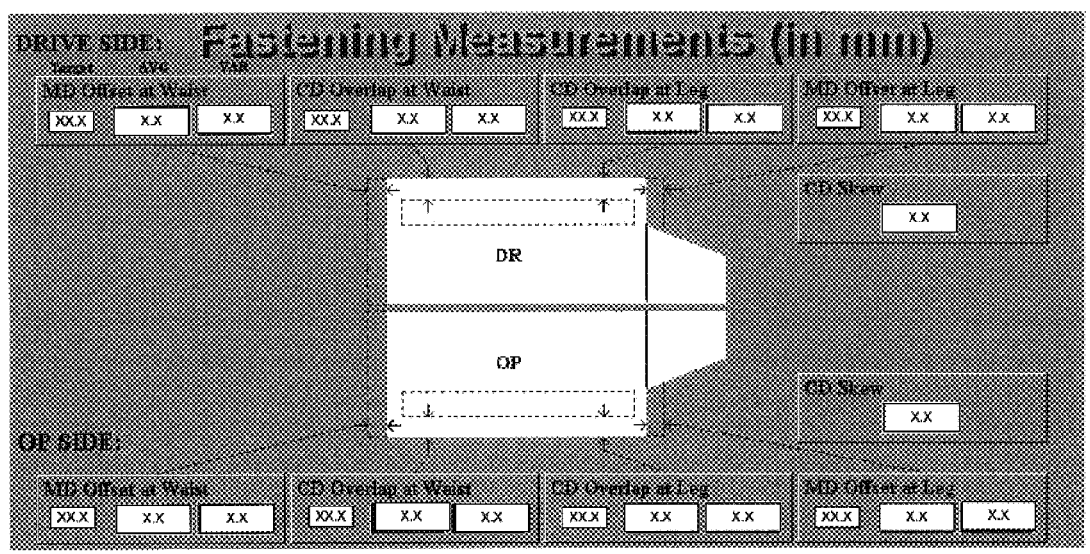

FIG. 16 illustrates an exemplary display of information associated with the selection of the PAC linescan option 2006. In this example, the data relates to a sample (batch) size of 50 inspected products. The average and standard deviation of various measurements taken by the PAC linescan inspection system are displayed relative to a desired target value. FIG. 17 illustrates an exemplary display of information associated with the selection of the quick check option 2012. FIG. 18 illustrates an exemplary display of information associated with the selection of the fastening inspection system option 2008. FIG. 19 illustrates an exemplary display of information associated with the selection of the Insight inspection option 2010.

Tracking Per Station Information On A Multiple Station Device

Referring now to FIG. 20, illustrated therein is a schematic representation of a system (referred to generally by reference 2100) and method for tracking per station manufacturing information from a multiple station device. For example, commonly owned U.S. Pat. No. 5,104,116 to Pohjola, discloses a multiple station device for rotating and placing a strip of material on a substrate so that the strip is "surfacely placed" generally flat with a continuously moving surface.

It has been known in the prior art to track information from a plurality of manufacturing stations, each station performing a different function in the manufacturing process. It has been generally unknown, however, to use machine vision systems and an information exchange to track and relate per station information from a multiple station device (sometimes referred to herein as a multiple repeat application device) that performs the same function—e.g., a six station device that performs the same function, sequentially using each of its six stations, on six sequential products being manufactured.

One particular example of a multiple station device is a side panel applicator used in manufacturing a disposable absorbent undergarment. Even more particularly, a side panel applicator 2102 uses twelve pucks mounted on a six-repeat applicator (two pucks per applicator station) to apply side panels to a product chassis, as generally described elsewhere herein. As also described herein, product (or process) attribute information, regarding each product being produced during a production run, is accumulated from various inspection systems (illustrated generally in FIG. 20 by reference 2104), including those illustrated elsewhere herein. This inspection data is available via network 1124 (e.g., a Reflective Memory network). The remainder of the discussion of FIG. 20 focuses primarily a discussion of particular examples. It should be understood that this discussion is provided for exemplary purposes and should not be construed in a limiting sense.

As explained above, in the exemplary embodiment illustrated, applicator 2102 is a six station device for applying side panels to the training pants. As shown in FIG. 20, station 1 of applicator 2102 applies a side panel for a first product A constructed during a portion of the production run. Station 2 of applicator 2102 applies a side panel to the next (second) product—product B—constructed during the production run. This process continues so that station 6 of applicator 2102 applies a side panel to the sixth product constructed in the sequence—product F. The process thereafter continues such that station 1 of applicator 2102 applies a side panel to the seventh product constructed in the sequence—product G. In other words, each product is identified by an identifier, in this example an upper case letter indicating its position in the manufacturing sequence and a number indicating which station of applicator 2102 applied the side panel to that product.

Inspection system 2104 images each product being produced (or a sample set thereof) and determines, for example, a measurement of side panel skew. The inspection data is accumulated and stored in a series of data collection/summary buffers 2110, which can be incorporated into information exchange 1110 As illustrated in the following TABLE 1, each buffer corresponds to a specific station of applicator 2102.

TABLE 1

| Buffer 1 (Station 1) | Buffer 2 (Station 2) | Buffer 3 (Station 3) | Buffer 4 (Station 4) | Buffer 5 (Station 5) | Buffer 6 (Station 6) |
|---|---|---|---|---|---|
| A | B | C | D | E | F |
| G | H | I | J | K | L |
| M | N | | | | |

Advantageously, therefore, the information (in this case inspection data) is now correlated to a particular station of the multi-station device 2102. Thus, problems (e.g., regarding quality, registration, and so on) can be pinpointed to an exact station. For example, information in each buffer can be displayed directly and/or mathematical manipulations of accumulations of such data can be displayed.

It is also contemplated that the same collected inspection data may be used to draw different conclusions. For example, the same information could be stored in buffers of different sizes to draw different conclusions for alarming and/or troubleshooting. As a specific example, the information from the side panel applicator system could be split into two buffers and related to the two repeat cut-off that is part of the applicator system. Alternatively or in addition, the information could be split into six buffers which would identify problems with a specific applicator station. Another example deals with the absorbent pad. Looking at the data broken between two buffers, each could be used to identify a problem with the absorbent debulker (two repeat), and eleven buffers could be used to identify a problem with the pad forming screens (eleven repeat).

Figure 21:
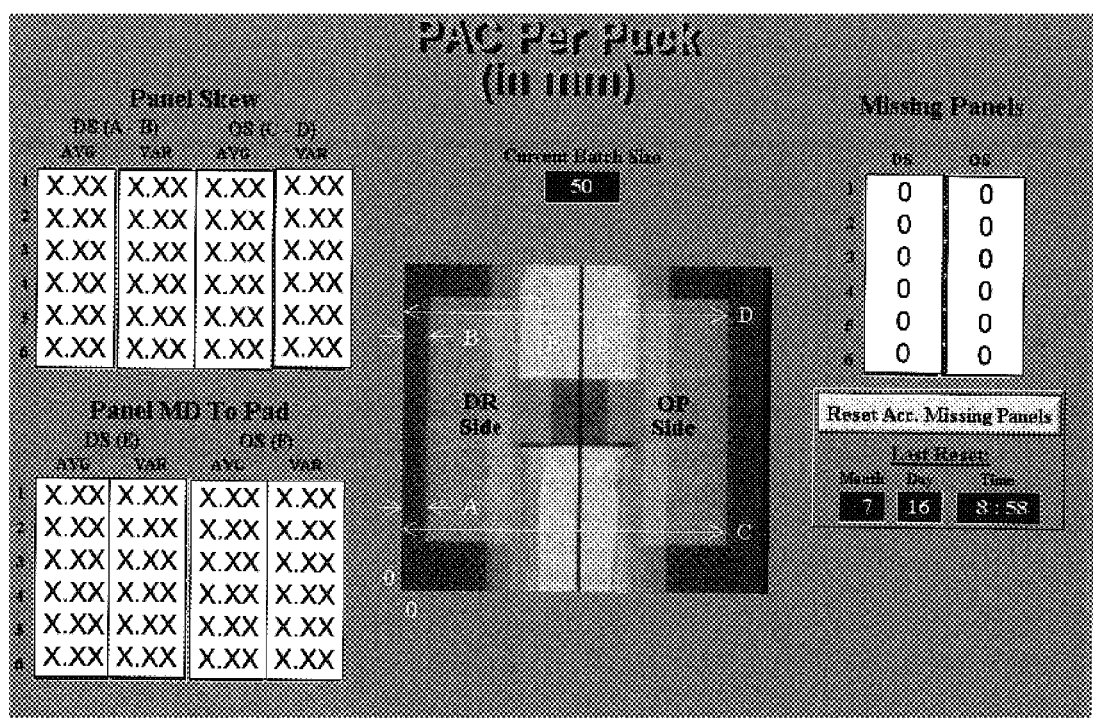
FIG. 21 illustrates an exemplary display of certain per station information for use in connection with a system such as that illustrated in FIG. 20.

FIG. 21 illustrates an exemplary display of inspection information, tracked on a per station basis, in connection with the example illustrated in FIG. 20. In the example of FIG. 21, the following information is displayed for a sample set of fifty products produced and inspected: (1) the drive side (DS) and operator side (OS) average side panel skew and skew variance, correlated by application station; (2) the drive side and operator side average and standard deviation calculations of measured panel placement in the machine direction relative to the pad, correlated by application station; and (3) the number of missing side panels (both drive side and operator side) detected during the sample set correlated by applicator station.

It should be understood that the per station information can also be stored in a database (indicated generally in FIG. 20 by reference 2112) so that historical relationships can be developed. For example, relationships can be assessed between the per station information and waste/delay data, raw material data, process setting data, and/or quality data.

The methods and systems disclosed herein for tracking per station information are applicable to a wide range of multiple repeat application devices, apart from the above-described six station device. For example, a multiple repeat screen applicator (e.g., an eleven repeat device) can be used in a pad formation process associated with constructing absorbent disposable articles (e.g., training pants). A two repeat debulker device may also be used in the pad formation process. If per station information is tracked for both of these multiple repeat devices—the eleven repeat screen applicator and the two repeat debulker—problems identified by inspection system 2104 can be correlated/isolated to the particular device and, preferably, to a particular a station of the isolated device. For instance, if an anomaly is detected in the pad—using inspection system 2104—on one out of eleven products (e.g., every eleventh product produced during a production run), it is likely that the eleven repeat device is implicated. If, however, an anomaly is detected in every other pad, it is more likely that the problem can be isolated to the debulker.

It should be appreciated that such isolation capabilities can be used in connection with the alarming and troubleshooting capabilities discussed elsewhere herein.

Another advantage of the methods and systems disclosed herein is the ability to relate data from multiple systems. For example, if inspection system 2104 comprises two or more inspection systems (such as those identified in FIG. 12), comparing measurements from both systems helps to better isolate problems. Referring to FIG. 12 as well as FIG. 20, in one exemplary embodiment, a first machine vision system 1502 comprises a Product Assembly Conveyor ("PAC") linescan inspection system because it uses a vision camera mounted near the conveyor where the product is assembled. In this location, vision system 1502 is positioned to acquire images of each product being produced before the addition of an outer cover assembly. Other vision systems (e.g., 1512 and 1520 in FIG. 12) are positioned at subsequent positions in the manufacturing process. Assume in this example that a position of absorbent assembly 44 is stable when inspected by the PAC linescan vision system (e.g., system 1502) but its position is not stable when inspected by a subsequent vision system. A processor (e.g., within information exchange 1110) having the inspection information regarding the position of the absorbent assembly from the inspection systems can apply a logic filter and determine that because absorbent assembly 44 is stable at the PAC linescan system but not stable in subsequent inspections, the problem causing the instability is not likely associated with formation of absorbent pad assembly 44 (which would be located upstream from the PAC linescan). Conversely, if absorbent assembly 44 is not stable at the PAC linescan inspection system, the logic filter preferably determines that the problem causing the instability is probably associated with the formation of absorbent assembly 44. Again, knowledge of such information can be used to provide, for example, alarms and troubleshooting indications to an operator. It can also be related to other data sources (e.g., raw material, productivity/waste/delay, quality, process setting, and so on) to identify relationships or potential relationships, such as data patterns, between manufacturing problems and the other data. These patterns may be identified by an information exchange, an operator interface or manually by an operator looking at a display of information relating to the patterns and performing calculations.

The ability to relate data from multiple systems (e.g., multiple inspection systems inspecting a product component from different locations in the production line) is especially powerful if a camera associated with a machine vision system is triggered off of a product component. For example, if the component triggering the camera is what is not stable (moving around), the image on the vision camera will appear stable—because it is triggered by the unstable component—and other components will look as if they are unstable. By using data from multiple systems, a processor such as information exchange 1110 can isolate which component is unstable.

The system disclosed in FIG. 20 will now be described in terms of another operating example involving an information exchange, such as information exchange 1110 illustrated and described elsewhere herein. A multiple repeat application device (e.g., applicator 2102) is configured for adding a component part to consecutive composite products (e.g., refastenable training pants) constructed by the sequential addition of various component parts. A machine vision system associated with inspection system 2104 preferably inspects substantially all composite products produced during a production run (or a sample set thereof) to identify one or more product (or process) attributes (e.g., side panel skew, absorbent assembly position, and so on) associated with each inspected product in the sequence. Preferably, inspection system 2104 determines a product (or process) attribute parameter corresponding to the inspected product (or process) attribute and makes that product (or process) attribute parameter available over the communication network 1124 (or otherwise). Information exchange 1110 collects product (or process) attribute parameters associated with the inspected products and buffers those parameters, as illustrated in FIG. 20 and TABLE 1, so that the parameters are correlated by product and by station of the multiple repeat device.

In one embodiment, information exchange 1110 accumulates sample sets of correlated product (or process) attribute parameters and determines a mathematical characteristic (e.g., an indication of variation, an average, and/or a standard deviation and so on) of each accumulated sample set. In a manner similar to that described elsewhere herein, the mathematical characteristic can be compared to a target (e.g., a limit or an ideal value or range of values) to determine if a problem exists. For example, in some contexts a high standard deviation may be indicative of a loose belt or a drive system problem.

Further, if information exchange 1110 determines that one of the six applicators of applicator 2102 is misplacing a component, an indication (e.g., an alarm or troubleshooting action corresponding to the applicator in question) can be displayed to an operator on operator interface 1118. Alternatively, information exchange 1110 can simply pass information to another processor (e.g., operator interface 1118) which compares the data to a target and determines any display indications to present on operator interface 1118.

In one embodiment, a data base system (e.g., data storage 2112) is configured for storing one or more types of data associated with the manufacturing process. Such manufacturing-related data types include, for example, quality characteristic data (e.g., derived from inspection system 2104 and/or manually measured and entered data), raw material characteristic data associated with the component part added by application device 2102, productivity data associated with a particular production run (e.g., waste and delay data associated with a work shift), and/or process setting data indicative of machine settings and set points associated with the manufacturing process (e.g., set points associated with device 2102). Such data items of interest are preferably stored in data storage 2112 are logically related to the inspection parameters provided by inspection system 2104. One way to provide such a logical relationship is to use a date/time stamp procedure. Another or additional way to provide such a logical relationship is to use specific product codes. Other relationship tools are possible. Preferably, information exchange 1110 includes a logic filter for executing data mining functions within such data stored in data storage 2112 to identify relationships such as data patterns between the inspection parameters and the manufacturing-related data.

With the benefit of the present disclosure, it will be possible to identify a number of data relationships of value to a variety of manufacturing processes such as high speed web converting processes. For example, storing per station inspection information can be stored for historical data tracking and reliability analyses, or for predictive maintenance actions and the like.

Product, Process, and Material Data Mining

Figure 22:
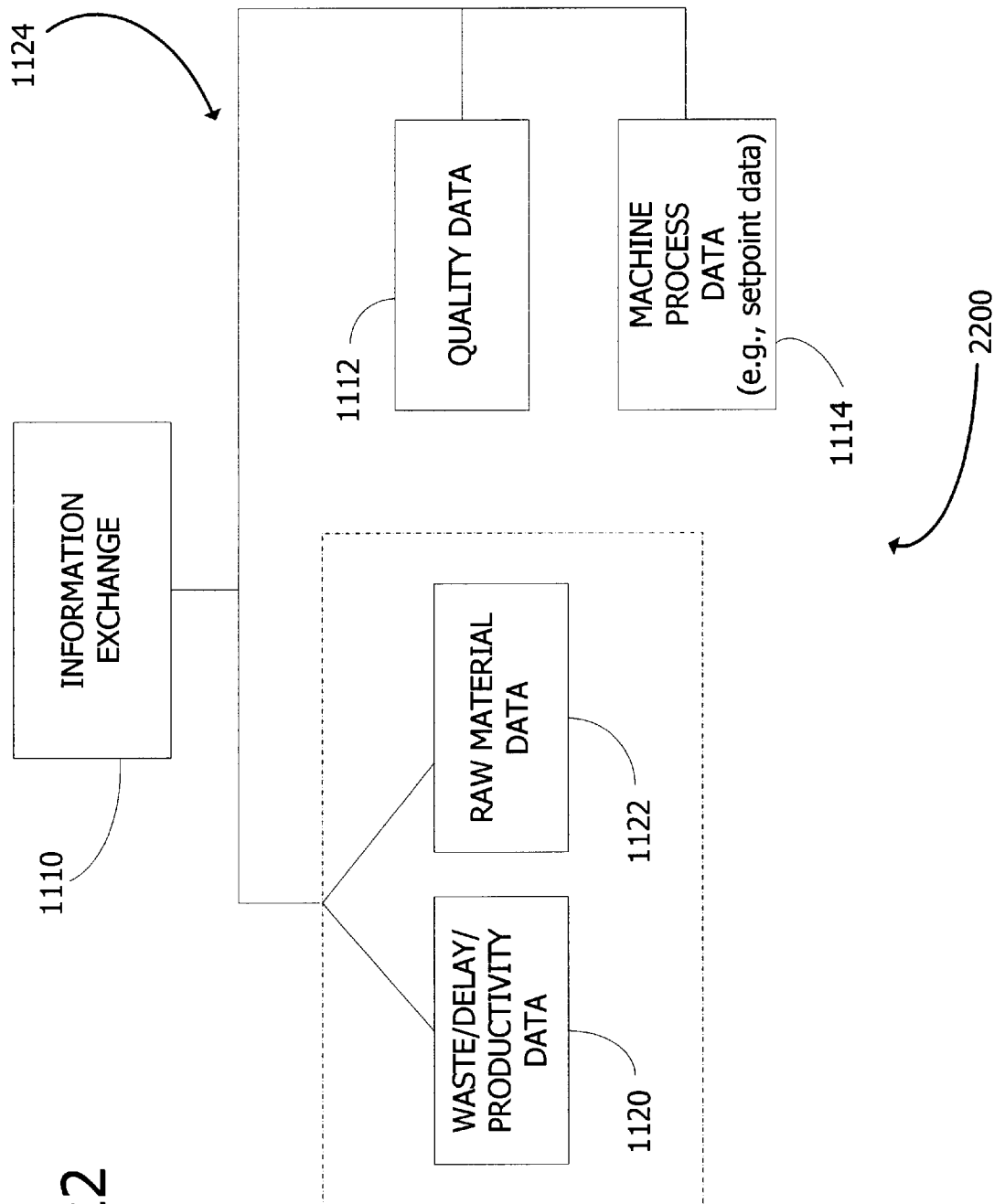
FIG. 22 is a block diagram illustrative of one configuration of a database system suitable for use in mining data in connection with an information system such as that illustrated in FIG. 4A.

FIG. 22 is a block diagram illustrative of one configuration of a database system (referred to generally in FIG. 22 by reference 2200) suitable for use in mining data in connection with an information system such as that illustrated in FIG. 4A. As illustrated, the database system includes waste/delay/productivity data 1120, raw material data 1122, quality data 1112 (e.g., automatically determined and/or manually measured data), and machine process data 1114. Each of these data types has been discussed and described elsewhere herein. Waste/delay/productivity data 1120 and raw material data 1122 are illustrated within a dashed box to reflect that, in one embodiment, such data is stored on a common computer system. It should be understood that the foregoing data may be stored separately or together. There are certain advantages to storing such data in a common computer, including a reduction in the overhead needed to access and transfer such data, which facilitates identifying relationships between the data.

As described above, a variety of product (or process) attribute information is gathered from machine sensors during the product manufacturing process. Again, using the manufacture of refastenable training pants (which includes high speed web converting processes) as an example, product (or process) attribute information includes side panel cut length, side panel skew, hook machine direction (MD) placement, hook cross direction (CD) placement, fastener overlap, fastener skew, MD fold offset, front panel length, and back panel length. As explained herein, some or all of this information is made available for display to an operator. Such product (or process) attribute information may also be stored for data mining or other analytical purposes. For example, such product (or process) attribute information can be stored in information exchange 1110 of FIG. 22. The product (or process) attribute information is thereafter linked to one or more other data sources of interest (e.g., one or more of data sources 1120, 1122, 1112, or 1114).

Advantageously, the foregoing data can be correlated to specific products or groups of products. Thus, it is possible to identify relationships that would have otherwise gone unnoticed. For example, assume that a particular product (or process) attribute is unsatisfactory for a group of products (perhaps even resulting in the culling of those products). Data mining techniques are used to determine if there is a correlation between the unsatisfactory products and the raw materials used or the process set points and so on. Similar, if a particular production run resulted in an exceptionally high rate of quality or productivity, it would be advantageous to identify any correlation to the raw material, set points, and so on. It should be understood that such data mining techniques include SQL queries used to generate reports that are correlated in terms of time (e.g., time-stamped data) and/or product. One or more logic filters can also be run on the data to further automate the data mining process.

Figure 23:
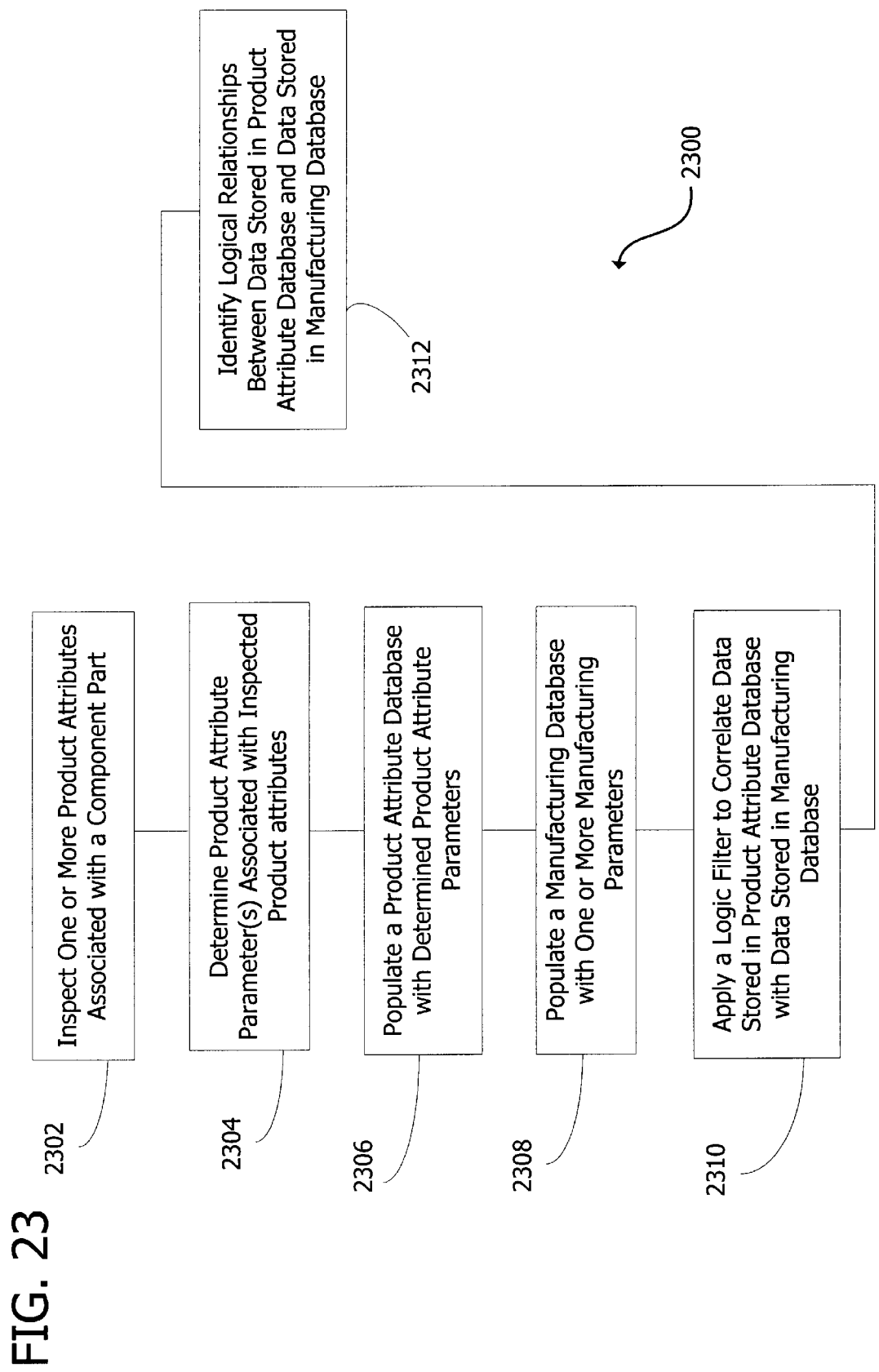
FIG. 23 is a logic flow diagram of a method for correlating product (or process) attribute information with other manufacturing related information for use in data mining applications in connection with an information system such as that illustrated in FIG. 4A.

FIG. 23 is a logic flow diagram of a method (indicated generally by reference 2300) for correlating product (or process) attribute information with other manufacturing related information. More particularly, at block 2302, an inspection system (such as inspection system 1104 having one or more machine vision inspection devices) inspects one or more product (or process) attributes associated with a composite product (e.g., a disposable absorbent article such as a refastenable child's training pant) being manufactured using a web converting process during a production run. In one embodiment, substantially all products constructed during the production run are inspected. In other embodiments, inspecting includes inspecting a sample set of products constructed during the production run.

At block 2304, product (or process) attribute parameters are determined for the inspected product (or process) attributes. In one embodiment, the inspection system provides an indication of the reliability/trustworthiness of the product (or process) attribute parameter. For example, and as discussed elsewhere herein, some machine vision inspection systems provide an indication of an inspection failure associated with the inspection system. Reliability/trustworthiness determinations can also be made by systems other than the inspection system. For example, an information exchange associated with the method could identify data that is so grossly out of bounds as to be untrustworthy.

At block 2306, the determined product (or process) attribute parameters are used to populate a product (or process) attribute database. In one embodiment, such a product (or process) attribute database comprises a part of information exchange 1110 (FIG. 22). It should be understood, however, that the product (or process) attribute database can be elsewhere, including, for example, a portion of quality database 1112 and so on.

Apart from (or in addition to) filtering product (or process) attribute parameters on the basis of reliability, one or more embodiments can also correlate such parameters to whether the particular product being inspected was culled or not culled. For example, one embodiment includes identifying two population sets within the product (or process) attribute database. A first population set comprises product (or process) attribute parameters associated with non-culled products, and a second population set comprises product (or process) attribute parameters associated with culled products. It should now be appreciated that certain data mining activities may focus only on culled products or non-culled products. For example, it may be desirable to conduct data mining activities associated with non-culled products to identify what factors tend to result in "good" production runs. In another embodiment, only data associated with non-culled products is stored in the product (or process) attribute database.

At block 2308, one or more manufacturing databases are populated with manufacturing parameters associated with the manufacture of the composite product. As described above, such manufacturing parameters include, for example, raw material data parameters (e.g., those stored in raw material database 1122), quality data parameters (e.g., those manually entered and those automatically added to quality database 11 12), waste/delay/productivity data parameters (e.g., those stored in waste/delay/productivity database 1120), and/or machine process data parameters (e.g., data stored in machine process database 1114).

In one embodiment, the data items of interest stored in the manufacturing databases include one or more identifiers for correlating the data stored therein with one or more product (or process) attribute parameters stored in the product (or process) attribute database. For example, a time-based identifier can be used to identify a time frame (e.g., a time of inspection or a time of manufacture) that may be used to correlate data in the respective databases. Other examples of identifiers that may be used separately or in combination include event-based identifiers (e.g., a raw material change, a shift change, a grade change, and so on) and product-based identifiers (e.g., product or lot identifiers).

At block 2310, a logic filter correlates data stored in the product (or process) attribute database with data stored in a manufacturing database. As suggested above, such a logic filter may include correlating the data of interest on the basis of a particular data identifier. In one embodiment, SQL queries perform the logic filtering functions.

At block 2312, the logical relationships are identified between the correlated data. As explained herein, such relationships include, for example, relationships between product (or process) attributes determined by the inspection system and raw material attributes (e.g., to identifying raw material contributions to good or bad product (or process) attributes). Other relationships include relationships between product (or process) attributes and process settings/set-ups (e.g., to identify good run and bad run settings), relationships between product (or process) attributes and waste/delay/productivity results (e.g., to identify whether a product (or process) attribute problems are responsible for waste/delay/productivity issues), and relationships between product (or process) attributes and product quality. Further, in one embodiment, multiple inspection systems are used to identify the product (or process) attribute. In such an embodiment, relationships between product (or process) attribute information from different inspection systems can be analyzed to identify additional relationships. Such relationships are useful for optimizing raw materials, product design, and improving manufacturing processes.

Further, logical relationships identified by the method illustrated in FIG. 23 can be displayed on an operator associated with the manufacturing production line, or can be determined later and used as part of post-manufacturing data analyses.

It should now be appreciated that the systems and methods disclosed herein result in several distinct advantages over the prior art. For example, although camera inspection systems have been used in the past, with the benefit of the present disclosure, it is now possible to take measurement data from one or more systems and relate such measurement data to other systems. Further, analyzing such relationships allows, among other things, improved process and quality control. As explained above, information from a raw material database can now be used to determine and anticipate material interactions to the manufacturing processes. Similarly, waste and delay data can be used to provide automatic grade changes to the process settings. Further, inspection data can be used in connection with maintaining and improving automatic registration control—using a separate registration control system and/or directly changing equipment set points. It is also possible to identify quality data for all products shipped, as opposed to determining quality only on the basis of a few samples.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A web guiding system suitable for use in connection with a continuous production line producing a composite web from two or more web components on a feed system supplying said web components to said continuous production line, the system comprising:
   a communication network;
   a vision inspection system capturing an image of the composite web and detecting in the captured image a relative placement of a first web component of the composite web to a second web component of the composite web, said vision inspection system providing to the communication network an inspection parameter indicative of said detected relative placement;
   an information exchange system obtaining via the communication network a plurality of inspection parameters, each associated with one of a plurality of composite webs, said information exchange system determining a mathematical characteristic of the obtained plurality of inspection parameters and providing the mathematical characteristic via the communication network; and
   a drive system for adjusting the feed system to adjust the relative placement of the first web component of the composite web to the second web component of the composite web, said drive system obtaining the provided mathematical characteristic and comparing said mathematical characteristic to a target, said drive system selectively adjusting the position of the feed system as a function of a difference between the mathematical characteristic and the target.

2. A system as set forth in claim 1 wherein the information exchange system is configured such that the mathematical characteristic comprises an average of the obtained plurality of inspection parameters.

3. A system as set forth in claim 1 wherein the information exchange system is configured such that the mathematical characteristic comprises a standard deviation of the obtained plurality of inspection parameters.

4. A system as set forth in claim 1 wherein the first web component comprises a first fastener component and the second web component comprises a second fastener component, said first and second fastener components being joined together by a composition process to form a fastener, and wherein the vision inspection system detects a relative placement of the first and second fastener components.

5. A system as set forth in claim 4 wherein the vision inspection system comprises a first camera and a second camera and the image captured by the vision inspection system comprises a composite image created from a first image captured using the first camera and a second image captured using the second camera.

6. A system as set forth in claim 4 wherein the vision inspection system is configured such that the inspection parameter comprises a numerical value being indicative of the relative placement of the first and second fastener components.

7. A system as set forth in claim 1 wherein the vision inspection system is configured such that the relative placement detected in the captured image comprises an overlap between the first and second web components and the inspection parameter comprises a numerical value indicative of said overlap and said target comprises an acceptability value.

8. A system as set forth in claim 7 wherein the information exchange system is configured such that the determined mathematical characteristic comprises an assessment of variability of the obtained plurality of inspection parameters, and wherein the drive system compares the assessment of variability to the acceptability value, whereby if said assessment of variability is greater than the acceptability value the drive system does not adjust the feed system, and if the assessment of variability is below the acceptability value the drive system steers the feed system in a direction chosen to maintain the overlap between the first and second web components at a substantially constant value.

9. A system as set forth in claim 8 wherein the assessment of variability comprises a standard deviation.

10. A system as set forth in claim 8 wherein the assessment of variability is a range, a variance, or a coefficient of variation.

11. A system as set forth in claim 8 wherein the feed system comprises a conveyor system.

12. A system as set forth in claim 11 wherein the conveyor system comprises a cross direction adjustable conveyor.

13. A system as set forth in claim 1 wherein the information exchange applies a filter to the plurality of inspection parameters, said filter being configured for identifying unreliable inspection parameters.

14. A system as set forth in claim 13 wherein the mathematical characteristic determined by the information exchange disregards unreliable inspection parameters included within the obtained plurality of inspection parameters.

15. A system as set forth in claim 1 wherein the feed system includes a web guide sensor for guiding the first web component, said web guide sensor having a mechanically translatable position, and wherein adjusting the feed system comprises adjusting the mechanically translatable position of the web guide sensor.

16. A system as set forth in claim 1 wherein the feed system includes a web guide sensor for guiding the first web component, said web guide sensor having a electronically adjustable operating set point, and wherein adjusting the feed system comprises adjusting the electronically adjustable operating set point of the web guide sensor.

17. A system as set forth in claim 1 wherein the feed system includes a web guide sensor for guiding the second web component, said web guide sensor having a mechanically translatable position, and wherein adjusting the feed system comprises adjusting the mechanically translatable position of the web guide sensor.

18. A system as set forth in claim 1 wherein the feed system includes a web guide sensor for guiding the second web component, said web guide sensor having a electronically adjustable operating set point and wherein adjusting the feed system comprises adjusting the electronically adjustable operating set point of the web guide sensor.

19. A system as set forth in claim 1 further comprising a logic filter for determining whether the first web component only should be selectively adjusted, whether the second web component only should be selectively adjusted or whether both the first and second web components should be simultaneously selectively adjusted and wherein the drive system is responsive to the logic filter to implement the determination of the logic filter.

20. A system as set forth in claim 1 further comprising a monitoring subsystem which monitors a parameter of the composite web, which compares the monitored parameter to a preset range and which provides an indication when the monitored parameter is outside the preset range.

21. A system as set forth in claim 20 wherein the indication is an alarm or a command to effect a shutdown of the web guiding system.

22. A system as set forth in claim 1 wherein the inspection system detects the relative placement of fist and second components and of second and third components and wherein the information exchange system infers the relative placement of the first and third components from the relative placement of first and second components and from the relative placement of second and third components and wherein the information exchange system uses the inferred relative placement of the first and third components for guiding the first or third components.

23. A system as set forth in claim 1 wherein the continuous production product line produces the composite web along a path, wherein the drive system adjusts the position of the feed system at a particular point along the path, wherein the vision inspection system captures an image at a particular point along the path which is downstream from the particular point along the path at which the drive system adjusts the position of the feed system and wherein the drive system adjusts the position of the feed system in response to the captured image.

24. A system as set forth in claim 1 wherein the continuous production product line produces the composite web along a path and wherein the produced composite web is provided to a downstream process.

25. A system as set forth in claim 24 wherein the drive system adjusts the position of the feed system at a particular point along the path, wherein the vision inspection system captures an image relating to a parameter of the downstream process system and wherein the drive system adjusts the position of the feed system in response to the captured image.

26. A system as set forth in claim 1 wherein the continuous production product line produces the composite web along a path, wherein the drive system adjusts the position of the feed system at a particular point along the path, wherein the vision inspection system captures an image at a particular point along the path which is upstream of the particular point along the path at which the drive system adjusts the position of the feed system and wherein the drive system adjusts the position of the feed system in response to the captured image.

27. A system as set forth in claim 1 wherein said drive system selectively adjusts the position of the feed system as a function of a predictive information correlated to the mathematical characteristic and the target.

28. A system as set forth in claim 1 wherein said drive system selectively adjusts the position of the first web component by reference to a reference point comprising one or more of the following: a fixed point; a reference point associated with the first web component being guided and/or a reference point associated with the second web component being guided.

29. A web guiding system suitable for use in connection with a continuous production line producing a composite web from two or more web components on a feed system supplying said web components to said continuous production line the system comprising:

a communication network;

a vision inspection system capturing an image of the composite web and detecting in the captured image a relative placement of a first web component of the composite web to a second web component of the composite web, said vision inspection system providing to the communication network an inspection parameter indicative of said detected relative placement;

an information exchange system obtaining via the communication network a plurality of inspection parameters, each associated with one of a plurality of composite webs, said information exchange system determining a mathematical characteristic of the obtained plurality of inspection parameters and providing the mathematical characteristic via the communication network; and a drive system for adjusting the feed system to adjust the relative placement of the first web component of the composite web to the second web component of the composite web, said drive system obtaining the provided mathematical characteristic and comparing said mathematical characteristic to a target, said drive system selectively adjusting the position of the feed system as a function of a predictive information correlated to the mathematical characteristic and the target.

30. A system suitable for use in connection with a continuous production line producing a composite web from two or more web components on a feed system supplying said web components to said continuous production line, the system comprising:

a communication network;

a vision inspection system capturing an image of the composite web and detecting in the captured image a relative placement of a first web component of the composite web to a second web component of the composite web, said vision inspection system providing to the communication network an inspection parameter indicative of said detected relative placement;

an information exchange system obtaining via the communication network a plurality of inspection parameters, each associated with one of a plurality of composite webs, said information exchange system determining a mathematical characteristic of the obtained plurality of inspection parameters and providing the mathematical characteristic via the communication network; and a drive system for adjusting the production line relative to the feed system to adjust the relative placement of the first web component of the composite web to the second web component of the composite web, said drive system obtaining the provided mathematical characteristic and comparing said mathematical characteristic to a target, said drive system selectively adjusting the production line as a function of a difference between the mathematical characteristic and the target.

31. A web guiding system suitable for use in connection with a continuous production line producing a composite web formed from two or more web components on a feed system supplying said web components to said continuous production line the system comprising:

a communication network;

a vision inspection system capturing an image of the composite web formed from first and second web components and detecting in the captured image a relative placement of the first web component to the second web component, said vision inspection system providing to the communication network an inspection parameter indicative of said detected relative placement;

an information exchange system obtaining via the communication network a plurality of inspection parameters, each associated with one of a plurality of composite webs, said information exchange system determining a mathematical characteristic of the obtained plurality of inspection parameters and determining an amount to adjust the feed system as a function of said determined mathematical characteristic, said information exchange system providing an adjustment parameter corresponding to the determined amount to adjust the feed system; and a drive system responsive to the adjustment parameter for selectively adjusting the feed system to adjust the relative placement of the first web component of the composite web to the second web component of the composite web.

32. A system as set forth in claim 31 wherein the information exchange system is configured such that the mathematical characteristic comprises an average of the obtained plurality of inspection parameters.

33. A system as set forth in claim 31 wherein the information exchange system is configured such that the mathematical characteristic comprises a standard deviation of the obtained plurality of inspection parameters.

34. A system as set forth in claim 31 wherein the first web component comprises a first fastener component and the second web component comprises a second fastener component, said first and second fastener components being joined together by a composition process to form a fastener, and wherein the vision inspection system detects a relative placement of the first and second fastener components.

35. A system as set forth in claim 34 wherein the vision inspection system comprises a first camera and a second camera and the image captured by the vision inspection system comprises a composite image created from a first image captured by the first camera and a second image captured by the second camera.

36. A system as set forth in claim 34 wherein the vision inspection system is configured such that the inspection parameter comprises a numerical value being indicative of the relative placement of the first and second fastener components.

37. A system as set forth in claim 31 wherein the vision inspection system is configured such that the relative placement detected in the captured image comprises an overlap between the first and second web components and the inspection parameter comprises a numerical value indicative of said overlap and said target comprises an acceptability value.

38. A system as set forth in claim 37 wherein the information exchange system is configured such that the determined mathematical characteristic comprises an assessment of variability of the obtained plurality of inspection parameters, said information exchange comparing the assessment of variability to the acceptability value, wherein when said assessment of variability is greater than the acceptability value the determined amount to adjust the feed system comprises no adjustment, and wherein when said assessment of variability is less than the acceptability value the determined amount to adjust the feed system comprises an amount of adjustment chosen such that the drive system will adjust the feed system in a direction determined to maintain the overlap between the first and second web components at a substantially constant value.

39. A system as set forth in claim 38 wherein the assessment of variability comprises a standard deviation.

40. A system as set forth in claim 38 wherein the assessment of variability is a range, a variance, or a coefficient of variation.

41. A system as set forth in claim 38 wherein the feed system comprises a conveyor system.

42. A system as set forth in claim 41 wherein the conveyor system comprises a cross direction adjustable conveyor.

43. A system as set forth in claim 31 wherein the information exchange applies a filter to the plurality of inspection parameters, said filter being configured for identifying unreliable inspection parameters.

44. A system as set forth in claim 43 wherein the mathematical characteristic determined by the information exchange disregards unreliable inspection parameters included within the obtained plurality of inspection parameters.

45. A system as set forth in claim 31 wherein the feed system includes a web guide sensor for guiding the first web component, said web guide sensor having a mechanically translatable position, and wherein adjusting the feed system comprises adjusting the mechanically translatable position of the web guide sensor.

46. A system as set forth in claim 31 wherein the feed system includes a web guide sensor for guiding the web component, said web guide sensor having a electronically adjustable operating set point, and wherein adjusting the feed system comprises adjusting the electronically adjustable operating set point of the web guide sensor.

47. A system as set forth in claim 31 wherein the feed system includes a web guide sensor for guiding the second web component, said web guide sensor having a mechanically translatable position, and wherein adjusting the feed system comprises adjusting the mechanically translatable position of the web guide sensor.

48. A system as set forth in claim 31 wherein the feed system includes a web guide sensor for guiding the second web component, said web guide sensor having a electronically adjustable operating set point, and wherein adjusting the feed system comprises adjusting the electronically adjustable operating set point of the web guide sensor.

49. A system as set forth in claim 31 further comprising a logic filter for determining whether the first web component only should be selectively adjusted, whether the second web component only should be selectively adjusted or whether both the first and second web components should be simultaneously selectively adjusted and wherein the provided adjustment parameter is responsive to the logic filter to implement the determination of the logic filter.

50. A system as set forth in claim 31 further comprising a monitoring subsystem which monitors a parameter of the composite web, which compares the monitored parameter to a preset range and which provides an indication when the monitored parameter is outside the preset range.

51. A system as set forth in claim 50 wherein the indication is an alarm or a command to effect a shutdown of the web guiding system.

52. A system as set forth in claim 31 wherein the inspection system detects the relative placement of first and second components and of second and third components and wherein the information exchange system infers the relative placement of the first and third components from the relative placement of first and second components and from the relative placement of second and third components and wherein the information exchange system uses the inferred relative placement of the first and third components for guiding the first or third components.

53. A system as set forth in claim 31 wherein the continuous production product line produces the composite web along a path, wherein the drive system adjusts the position of tee feed system at a particular point along the path, wherein the vision inspection system captures an image at a particular point along the path which is downstreamn from the particular point along the path at which the drive system adjusts the position of the feed system and wherein the adjustment parameter provided to the drive system is such that the drive system adjusts the position of the feed system in response to the captured image.

54. A system as set forth in claim 31 wherein the continuous production product line produces the composite web along a path and wherein the produced composite web is provided to a downstream process.

55. A system as set forth in claim 54 wherein the drive system adjusts the position of the feed system at a particular point along the path, wherein the vision inspection system captures an image relating to a parameter of the downstream process system and wherein the adjustment parameter provided to the drive system is such that the drive system adjusts the position of the feed system in response to the captured image.

56. A system as set forth in claim 31 wherein the continuous production product line produces the composite web along a path, wherein the drive system adjusts the position of the feed system at a particular point along the path, wherein the vision inspection system captures an image at a particular point along the path which is upstream of the particular point along the path at which the drive system adjusts the position of the feed system and wherein the adjustment parameter provided to the drive system is such that the drive system adjusts the position of the feed system in response to the captured image.

57. A system as set forth in claim 31 wherein the adjustment parameter provided to the drive system is such that the drive system selectively adjusts the position of the feed system as a function of a predictive information correlated to the mathematical characteristic and the target.

58. A system as set forth in claim 31 wherein the adjustment parameter provided to the drive system is such that the drive system selectively adjusts the position of the first web component by reference to a reference point comprising one or more of the following: a fixed point; a reference point associated with the first web component being guided and/or a reference point associated with the second web component being guided.

59. A system suitable for use in connection with a continuous production line producing a composite web formed from two or more web components on a feed system supplying said web components to said continuous production line, the system comprising:
   a communication network;
   a vision inspection system capturing an image of the composite web formed from first and second web components and detecting in the captured image a relative placement of the first web component to the second web component, said vision inspection system providing to the communication network an inspection parameter indicative of said detected relative placement;
   an information exchange system obtaining via the communication network a plurality of inspection parameters, each associated with one of a plurality of composite webs, said information exchange system determining a mathematical characteristic of the obtained plurality of inspection parameters and determining an amount to adjust the feed system as a function of said determined mathematical characteristic, said information exchange system providing an adjustment parameter corresponding to the determined amount to adjust the feed system; and
   a drive system responsive to the adjustment parameter for selectively adjusting the production line relative to the feed system to adjust the relative placementof the first web component of the composite web to the second web component of the composite web.

60. A web guiding method, suitable for use in connection with a production line producing a composite product from a first web component combined with a second web component, the method comprising:
   capturing an image of the first and second components after combining said first and second web components;
   detecting in the captured image a placement of the first web component relative to the second web component;
   providing an inspection parameter indicative of the placement of the first web component relative to the second web component;
   obtaining a plurality of inspection parameters, each associated with one of a plurality of composite products;
   determining a mathematical characteristic of the obtained plurality of inspection parameters;
   comparing the mathematical characteristic to a target; and
   selectively adjusting a drive set point associated with providing the first web component prior to combination with the second web component as a function of a difference between the mathematical characteristic and the target.

61. A method as set forth in claim 60 wherein determining the mathematical characteristic comprises determining an average of the obtained plurality of inspection parameters.

62. A method as set forth in claim 60 wherein determining the mathematical characteristic comprises determining a standard deviation of the obtained plurality of inspection parameters.

63. A method as set forth in claim 60 wherein the first and second components are combined by a joining process resulting in an overlapping relationship between the first and second components, and wherein detecting in the captured image the placement of the first web component relative to the second web component comprises detecting an amount of overlap between the first web component and the second web component and wherein the inspection parameter indicates said amount of overlap.

64. A method as set forth in claim 63 wherein the mathematical characteristic comprises an assessment of variability of the obtained plurality of inspection parameters and wherein comparing the mathematical characteristic to the target comprises comparing the assessment of variability to an acceptability value associated with the amount of overlap such that if the assessment of variability is greater than the acceptability value the drive set point is not adjusted.

65. A method as set forth in claim 64 wherein the assessment of variability comprises a standard deviation.

66. A method as set forth in claim 64 wherein the assessment of variability is a range, a variance, or a coefficient of variation.

67. A method as set forth in claim 60 wherein capturing the image of the first and second components after combining said web components comprises providing a composite image of the first and second components after combining, said composite image being created from separate images captured by two or more separate cameras positioned to selectively obtain images of the first and second components after combining.

68. A method as set forth in claim 60 further comprising applying a filter to the plurality of inspection parameters, said filter being configured for identifying unreliable inspection parameters.

69. A method as set forth in claim 60 further comprising selectively determining whether the first web component only should be selectively adjusted, whether the second web component only should be selectively adjusted or whether both the first and second web components should be simultaneously selectively adjusted and implementing the selective determination.

70. A method as set forth in claim 60 further comprising monitoring a parameter of the composite web, comparing the monitored parameter to a preset range and providing an indication when the monitored parameter is outside the preset range.

71. A method as set forth in claim 70 wherein the indication is an alarm or comprises shutting down the web guiding system.

72. A method as set forth in claim 60 further comprising detecting the relative placement of first and second components and of second and third components and inferring the relative placement of the first and third components from the relative placement of first and second components and from the relative placement of second and third components and guiding the first or third components in response to the inferred relative placement of the first and third components.

73. A method as set forth in claim 60 wherein the product line produces the composite product along a path, wherein the position of the web is adjusted at a particular point along the path, wherein an image is captured at a particular point along the path which is downstream from the particular point along the path at which the position is adjusted and wherein the position of the web is adjusted in response to the captured image.

74. A method as set forth in claim 60 further comprising providing the composite web to a downstream process.

75. A method as set forth in claim 74 wherein the drive system adjusts the position of the feed system at a particular point along the path, wherein the vision inspection system captures an image relating to a parameter of the downstream process system and wherein the drive system adjusts the position of the feed system in response to the captured image.

76. A method as set forth in claim 60 wherein the product line produces the composite product along a path, wherein the position of the web is adjusted at a particular point along the path, wherein an image is captured at a particular point along the path which is upstream of the particular point along the path at which the position is adjusted and wherein the position of the web is adjusted in response to the captured image.

77. A web guiding method, suitable for use in connection with a production line producing a composite product from a first web component combined with a second web component, the method comprising:

capturing a first image of the first and second components after combining said first and second web components;

detecting in the first captured image a first placement of the first web component relative to the second web component;

capturing a second image of the first and second components after combining said first and second web components;

detecting in the second captured image a second placement of the first web component relative to the second web component;

comparing the first placement to the second placement to identify an amount indicative of a relative placement of the first and second web components;

providing an inspection parameter indicative of the indicative amount between the first and second web components;

obtaining a plurality of inspection parameters, each associated with one of a plurality of composite products;

determining a mathematical characteristic of the obtained plurality of inspection parameters;

comparing the mathematical characteristic to a target; and selectively adjusting a drive set point associated with providing the first web component prior to combination with the second web component as a function of a difference between the mathematical characteristic and the target.

78. A method, suitable for use in connection with a production line producing a composite product from a first web component combined with a second web component, said fist and second web components supplied by a feed system, the method comprising:

capturing an image of the first and second components after combining said first and second web components;

detecting in the captured image a placement of the first web component relative to the second web component;

providing an inspection parameter indicative of the placement of the first web component relative to the second web component;

obtaining a plurality of inspection parameters, each associated with one of a plurality of composite products;

determining a mathematical characteristic of the obtained plurality of inspection parameters;

comparing the mathematical characteristic to a target; and selectively adjusting a parameter of the production line prior to combination of the first web component with the second web component as a function of a difference between the mathematical characteristic and the target to adjust the relative placement of the first web component to the second web component.

79. A web guiding method suitable for use in connection with a continuous production line producing a composite web from two or more web components on a feed system supplying said web components to said continuous production line, the method comprising:

capturing an image of the composite web;

detecting in the captured image a relative placement of a first web component of the composite web to a second web component of the composite web;

providing to a communication network an inspection parameter indicative of said detected relative placement;

obtaining via the communication network a plurality of inspection parameters, each associated with one of a plurality of composite webs;

determining a mathematical characteristic of the obtained plurality of inspection parameters;

providing the mathematical characteristic via the communication network;

adjusting a position of the feed system;

obtaining the provided mathematical characteristic;

comparing said mathematical characteristic to a target; and selectively adjusting the feed system as a function of a predictive information correlated to the mathematical characteristic and the target to adjust the relative placement of the first web component of the composite web to the second web component of the composite web.

* * * * *